(12) United States Patent
Garvey et al.

(10) Patent No.: US 7,160,920 B2
(45) Date of Patent: *Jan. 9, 2007

(54) NITROSATED AND NITROSYLATED COMPOUNDS AND COMPOSITIONS AND THEIR USE FOR TREATING RESPIRATORY DISORDERS

(75) Inventors: David S. Garvey, Waltham, MA (US); L. Gordon Letts, Dover, MA (US); H. Burt Renfroe, Wellesley, MA (US); Stewart K. Richardson, Ashford, CT (US)

(73) Assignee: NitroMed, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/428,936

(22) Filed: May 5, 2003

(65) Prior Publication Data

US 2003/0199529 A1 Oct. 23, 2003

Related U.S. Application Data

(60) Division of application No. 09/689,851, filed on Oct. 13, 2000, now Pat. No. 6,579,863, which is a division of application No. 09/157,242, filed on Sep. 18, 1998, now Pat. No. 6,197,762, which is a division of application No. 08/620,882, filed on Mar. 22, 1996, now Pat. No. 5,824,669, and a continuation of application No. PCT/US97/04319, filed on Mar. 19, 1997.

(51) Int. Cl.
*A61K 31/21* (2006.01)
*C07C 203/00* (2006.01)
*C07D 401/00* (2006.01)

(52) U.S. Cl. .................. 514/506; 514/509; 546/273.1; 546/334; 558/483; 558/488

(58) Field of Classification Search ................ 514/506, 514/509; 558/483, 488; 546/273.1, 334
See application file for complete search history.

(56) References Cited

U.S. PATENT DOCUMENTS

| 3,316,152 | A | | 4/1967 | Heider et al. | |
|---|---|---|---|---|---|
| 3,639,434 | A | | 2/1972 | Oxley et al. | |
| 3,743,741 | A | | 7/1973 | Laurent et al. | |
| 3,839,369 | A | | 10/1974 | Hofmeister et al. | |
| 5,274,002 | A | | 12/1993 | Hawkins | |
| 5,475,003 | A | | 12/1995 | Wilhelm et al. | |
| 5,703,073 | A | * | 12/1997 | Garvey et al. | .................. 514/2 |
| 5,707,984 | A | | 1/1998 | Tjoeng et al. | |
| 5,792,758 | A | | 8/1998 | Tjoeng et al. | |
| 5,824,669 | A | * | 10/1998 | Garvey et al. | ............... 514/174 |
| 5,837,698 | A | | 11/1998 | Tjoeng et al. | |
| 5,932,538 | A | * | 8/1999 | Garvey et al. | .................. 514/2 |
| 6,051,588 | A | * | 4/2000 | Garvey et al. | ............... 514/364 |
| 6,197,762 | B1 | * | 3/2001 | Garvey et al. | ............... 514/174 |
| 6,410,791 | B1 | | 6/2002 | Soldato | |
| 6,579,863 | B1 | * | 6/2003 | Garvey et al. | ............... 514/171 |
| 6,930,113 | B1 | * | 8/2005 | Garvey et al. | ............ 514/262.1 |
| 2005/0059665 | A1 | * | 3/2005 | Khanapure et al. | ..... 514/252.03 |

FOREIGN PATENT DOCUMENTS

| CA | 969 927 | 6/1975 |
|---|---|---|
| CA | 975 755 | 10/1975 |
| DE | 1643034 | 5/1971 |
| EP | 0 722 944 | 7/1996 |
| GB | 1082573 | 9/1967 |
| GB | 1082574 | 9/1967 |
| WO | WO 92/17445 | 10/1992 |
| WO | WO 93/09806 | 5/1993 |
| WO | WO 93/12068 | 6/1993 |
| WO | WO 95/09636 | 4/1995 |
| WO | WO 95/26768 | 10/1995 |
| WO | WO 97/21721 | 6/1997 |
| WO | WO 97/21724 | 6/1997 |
| WO | WO 97/40836 | 11/1997 |
| WO | WO 97/41144 | 11/1997 |
| WO | WO 98/15568 | 4/1998 |
| WO | WO00/06531 | 2/2000 |
| WO | WO00/61541 | 10/2000 |
| WO | WO01/12584 | 2/2001 |

OTHER PUBLICATIONS

Gaston et al, Proc. Natl. Acad. Sci. USA, 90:10957-10961 (1993).
Derwent Abstract Accession No. NL 7801838 (Aug. 21, 1979).

* cited by examiner

*Primary Examiner*—Barbara P. Badio
(74) *Attorney, Agent, or Firm*—Wilmer Cutler Pickering Hale and Dorr LLP

(57) ABSTRACT

Disclosed are (i) compounds of a steroid, a β-agonist, an anticholinergic, a mast cell stabilizer and a phosphodiesterase (PDE) inhibitor directly or indirectly linked to a NO or $NO_2$ group or a group which stimulates endogenous production of NO or EDRF in vivo; (ii) compositions of steroids, β-agonists, anticholinergics, mast cell stabilizers and PDE inhibitors, which can optionally be substituted with at least one NO or $NO_2$ moiety or a group which stimulates endogenous production of NO or EDRF in vivo, and a compound that donates, transfers or releases nitric oxide as a charged species, i.e., nitrosonium ($NO^+$) or nitroxyl ($NO^-$), or as the neutral species, nitric oxide (NO.) or that stimulates endogenous production of NO or EDRF in vivo; and (iii) uses for them in preventing and/or treating respiratory disorders.

58 Claims, 29 Drawing Sheets

IVC

19

VC

23

VIIC

↑

36

NITROSATED AND NITROSYLATED COMPOUNDS AND COMPOSITIONS AND THEIR USE FOR TREATING RESPIRATORY DISORDERS

RELATED APPLICATIONS

This application is a divisional of U.S. application Ser. No. 09/689,851, filed Oct. 13, 2000, issued as U.S. Pat. No. 6,579,863, which is a divisional of U.S. application Ser. No. 09/157,242, filed Sep. 18, 1998, issued as U.S. Pat. No. 6,197,762, which is a divisional of U.S. application Ser. No. 08/620,882 filed Mar. 22, 1996, issued as U.S. Pat. No. 5,824,669, and RE 037611; and is a continuation of PCT Application No. PCT/US 97/04319 filed Mar. 19, 1997.

BACKGROUND OF THE INVENTION

The present invention relates to the field of compounds, compositions and uses therefore, in oral and/or nasal administration prophylaxis and/or treatment of respiratory disorders. More particularly the invention relates to nitrosated and nitrosylated compounds, compositions comprising such compounds, which can optionally be unsubstituted or substituted with at least one NO or $NO_2$ moiety, and a compound that donates, transfers or releases nitric oxide as a charged species, i.e., nitrosonium (NO+) or nitroxyl (NO), or as the neutral species, nitric oxide (NO.); and uses for each of them.

A broad spectrum of respiratory diseases and disorders have been recognized, many of which have overlapping and interacting etiologies. One of the most widespread and prevalent of these diseases in western populations is the chronic disease referred to as "asthma". Other such disorders are also characterized by acute pulmonary vasoconstriction such as may result from pneumonia, traumatic injury, aspiration or inhalation injury, fat embolism in the lung, acidosis inflammation of the lung, adult respiratory distress syndrome, acute pulmonary edema, acute mountain sickness, post-cardiac surgery, acute pulmonary hypertension, persistent pulmonary hypertension of the newborn, perinatal aspiration syndrome, hyaline membrane disease, acute pulmonary thromboembolism, herapin-protamine reactions, sepsis, status asthmaticus or hypoxia (including iatrogenic hypoxia) and other forms of reversible pulmonary vasoconstriction. Such pulmonary disorders also are also characterized by inflammation of the lung including those associated with the migration into the lung of nonresident cell types including the various leucocyte subclasses. Also included in the respiratory disorders contemplated are cystic fibrosis and other diseases which are characterized by excess mucosal secretion. Other physiological events which are contemplated to be controlled include platelet activation in the lung.

Asthma is a major and disabling obstructive respiratory disease associated with significant morbidity and mortality. The term "asthma" has been used to describe a condition which is characterized by widespread fluctuations in the diameter or caliber of bronchial airways over short periods of time resulting in changes in lung function. The resulting increased resistance to air flow produces symptoms including breathlessness (dyspnea), chest constriction or "tightness" and wheeze. The term as used is not currently limited to a disorder or disease resulting from any specific cause or causes, rather it is characterized by its clinical manifestation. A true immunological mechanism may or may not be a factor in the etiology of an individual asthmatic condition. Further, characteristic wheezing may not be present in particularly severe attacks where transport of air is completely obstructed. Regardless of the cause, asthma in all sufferers is characterized by reversible hyperresponsiveness of tracheal bronchial smooth muscle resulting in its contraction and interference with normal respiration. The lungs of patients who die of asthma are usually pale pink, hyperinflated, and fail to collapse after their removal from the chest. Many of the airways throughout the bronchial tree are occluded by thick mucus plugs which are infiltrated with various types of leukocytes, including mast cells. The smooth muscle of the airways is hypertrophied. The bronchoconstriction or bronchospasm characterized by asthmatic attacks causes obstruction to air flow which necessitates a forced exhalation and maintenance of artificially elevated functional air reserve capacity to keep the airways open. The resultant lung hyperinflation places a significant stress on the cardiovascular system (particularly the right ventricle) which can lead to a consequent cardiovascular event. One possible result is a progressive decrease in cardiac output referred to as "cardiopulmonary tamponade". Most deaths resulting from asthma are caused by a condition referred to as "status asthmaticus," which is essentially an intensely severe and bronchospasm that is unresponsive to treatment.

Various categories of drugs are known to be useful in the inhalation of treatment of asthma. These include $\beta_2$ agonists (such as salmeterol, albuterol, metaproternol, terbutaline, pirbuterol, rimiterol, clenbuterol, bitolterol and repreterol, adrenalin, isoproterenol, ephedrine, orciprenlaine, fenoterol and isoetharine); anticholinergic agents (such as atropine, ipratropium, flutropium, tiotropium and rispenzepine) and mast cell stabilizers (chromolyn and nedocromil). Selective $\beta$ agonists have recently been developed with fewer cardiotonic side effects than those previously employed and are now considered suitable therapeutics for management of bronchitis and, particularly, emphysema, for which there previously had not been a suitable effective form of therapy.

Although corticosteroids are not generally indicated for routine use in the treatment of asthma, whether acute or chronic, they are used in large doses in the treatment of status asthmaticus. Nonetheless, the use of inhaled corticosteroids for the treatment of bronchial asthma has increased in recent years. Most frequently beclomethasone dipropionate, triamcinolone acetonide or flunisolide can be used to reduce or replace oral corticosteroid therapy, particularly in the treatment of children. This avoids or reduces bronchial reactivity and behavioral toxicity. See Cott and Cherniack, *Steroids and "Steroid-sparing Agents in Asthma"*, New Engl. J. Med., 318:634–636, 1988.

Cystic fibrosis is a multi-organ disorder of the exocrine glands which is congenital, lethal and affects all populations, particularly European and North American populations. Primary effects of cystic fibrosis are in the secretory glands, particularly mucous secretion. One of the organ systems most effected by cystic fibrosis is the lungs and respiratory tract. Therapy is as yet only symptomatic as the underlying genetic defect has yet to be characterized.

SUMMARY OF THE INVENTION

The present invention is based on the discovery by the inventors that it is possible to directly or indirectly link an NO or $NO_2$ group or a group which stimulates the endogenous production of NO or endothelium-derived relaxing factor (EDRF) in vivo, to a steroid, a $\beta$-agonist, an anticholinergic, a mast cell stabilizer or a phosphodiesterase (PDE) inhibitor and that the resulting compound has beneficial therapeutic effects of both a steroid, a β-agonist, an anticholinergic, a mast cell stablizer, or PDE inhibitor and an NO donor or stimulator.

Therefore, one aspect of the invention provides a compound comprising a steroid, a β-agonist, an anticholinergic, a mast cell stabilizer or a PDE inhibitor to which is directly or indirectly linked at least one NO or $NO_2$ group or a group which stimulates the endogenous production of NO or EDRF in vivo. The groups can be linked through sites such as oxygen (hydroxyl condensation), sulfur (sulfhydryl condensation), carbon and nitrogen.

The invention is further based on the discovery by the inventors that it is possible to co-administer a steroid, a β-agonist, an anticholinergic, a mast cell stabilizer or a PDE inhibitor with a compound that donates, transfers or releases nitric oxide and/or a compound that stimulates endogenous production of NO or EDRF in vivo. A nitric oxide donor is a compound that contains a nitric oxide moiety and which releases or chemically transfers nitric oxide to another molecule. Nitric oxide donors include but are not limited to S-nitrosothiols, nitrites, 2-hydroxy-2-nitrosohydrazines, and substrates of various forms of nitric oxide synthase. Compounds that stimulate endogenous production of nitric oxide or EDRF in vivo include L-arginine, the substrate for nitric oxide synthase, cytokines, adenosine, bradykinin, calreticulin, bisacodyl, phenolphthalein, and endothelein.

Therefore, another aspect of the invention provides a composition comprising (i) a therapeutically effective amount of a a steroid, a β-agonist, an anticholinergic, a mast cell stabilizer and/or a PDE inhibitor in combination with (ii) a compound that donates, transfers or releases nitric oxide and/or a compound that stimulates endogenous production of NO or EDRF in vivo.

In another aspect the invention provides a composition comprising (i) a therapeutically effective amount of a steroid, a β-agonist, an anticholinergic, a mast cell stabilizer or a PDE inhibitor to which is directly or indirectly linked at least one NO or $NO_2$ group or a group that stimulates endogenous production of NO or EDRF in vivo, and (ii) a compound that donates, transfers or releases nitric oxide and/or a compound that stimulates endogenous production of NO or EDRF in vivo. The invention also provides such compositions in a pharmaceutically acceptable carrier.

In another aspect the invention provides a method for treating respiratory disorders, such as asthma, in an individual in need thereof which comprises administering to the individual a therapeutically effective amount of a steroid, a β-agonist, an anticholinergic, a mast cell stabilizer or a PDE inhibitor to which is directly or indirectly linked at least one NO or $NO_2$ group and/or a group that stimulates endogenous production of NO or EDRF in vivo.

In another aspect the invention provides a method of treating respiratory disorders, such as asthma, in an individual in need thereof which comprises administering to the individual (i) a therapeutically effective amount of a steroid, a β-agonist, an anticholinergic, a mast cell stabilizer or a PDE inhibitor, which optionally may be substituted with at least one NO or $NO_2$ group or a group that stimulates endogenous production of NO or EDRF in vivo, and (ii) a compound that donates, transfers or releases nitric oxide, and/or a group that stimulates production of NO or EDRF in vivo.

The steroid, β-agonist, anticholinergic, mast cell stabilizer or PDE inhibitor and the compound that donates, transfers or releases nitric oxide and/or stimulates endogenous production of NO or EDRF in vivo can be administered separately or as components of the same composition in one or more pharmaceutically acceptable carriers.

BRIEF DESCRIPTION OF THE FIGURES

The following drawings are illustrative of embodiments of the invention and do not limit the scope of the invention as defined by the claims.

DETAILED DESCRIPTION OF THE INVENTION

Figure 1:
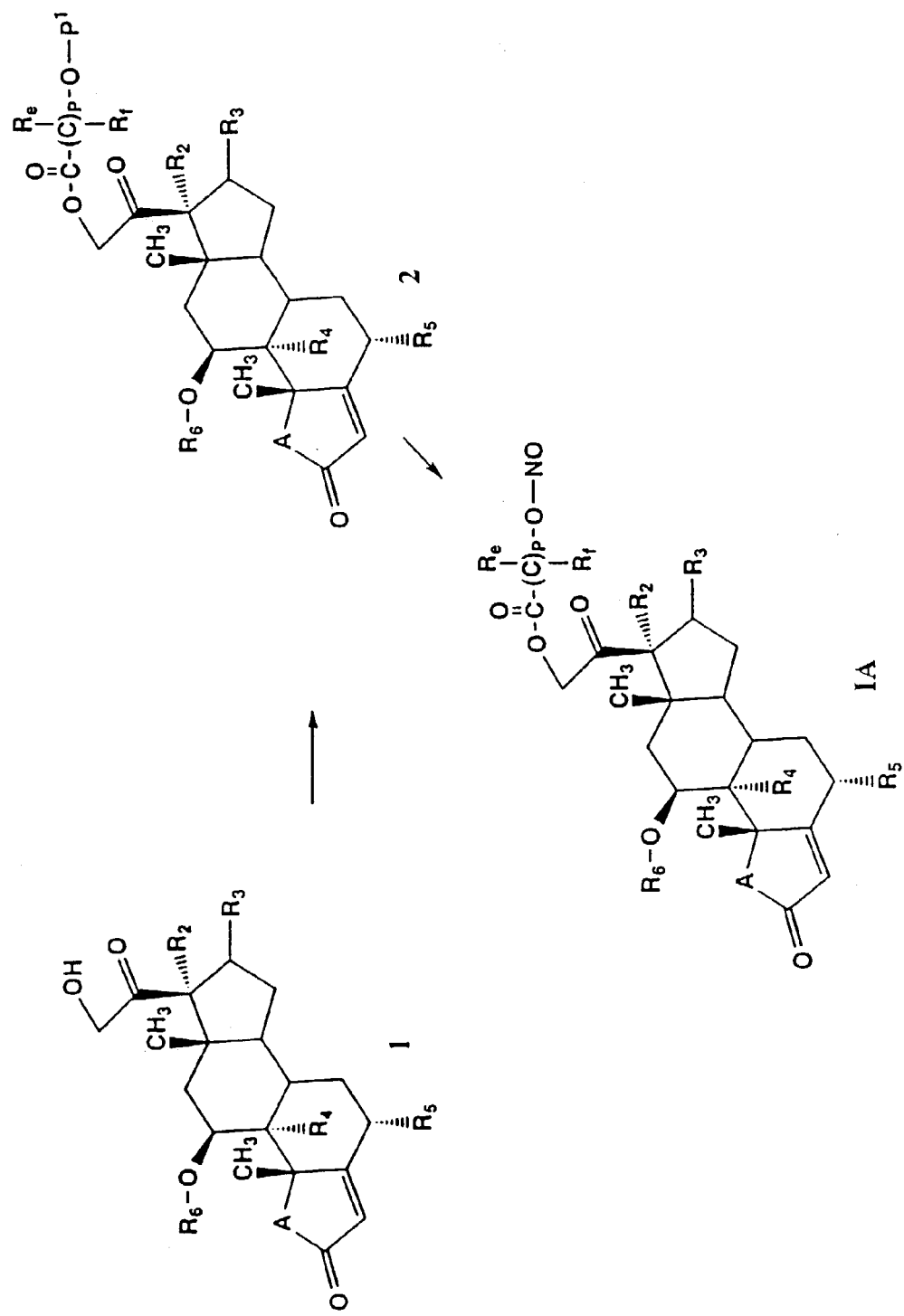
FIG. 1 illustrates a synthetic pathway for the preparation of nitrite containing steriod derivatives.

The following illustrative elucidations are provided to facilitate understanding of certain terms used frequently herein, particularly in the examples. The elucidations are provided as a convenience and are not limitative of the invention.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to $R_{50}$O-wherein $R_{50}$ is lower alkyl as defined above. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "hydroxy" as used herein refers to —OH.

The term "hydroxyalkyl" as used herein refers to a hydroxy group as previously defined appended to a lower alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —NH$_2$.

The term "carboxy" as used herein refers to —C(O)O—

The term "nitrate" as used herein refers to —O—NO$_2$.

The term "alkylamino" as used herein refers to $R_{51}$NH- wherein $R_{51}$ is a lower alkyl group as defined above, for example, methylamino, ethylamino, butylamino, and the like.

The term "dialkylamino" as used herein refers to $R_{52}R_{53}$N-wherein $R_{52}$ and $R_{53}$ are independently selected from lower alkyl groups as defined above, for example dimethylamino, diethylamino, methyl propylamino and the like.

The term "nitro" as used herein refers to the group —NO$_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from loweralkyl, haloalkyl, alkoxy, amino, alkylamino, dialkylamino, hydroxy, halo, and nitro. In addition, substituted aryl groups include tetrafluorophenyl and pentafluorophenyl.

The term "arylalkyl" as used herein refers to a lower alkyl radical to which is appended an aryl group. Representative arylalkyl groups include benzyl, phenylethyl, hydroxybenzyl, fluorobenzyl, fluorophenylethyl and the like.

The term "arylalkoxy" as used herein refers to an alkoxy radical to which is appended an aryl group. Representative arylalkoxy groups include benzyloxy, phenylethoxy, chlorophenylethoxy and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "bridged cycloalkyl" herein refers to two or more cycloalkyl radicals fused via adjacent or non-adjacent carbon atoms, including but not limited to adamantyl and decahydronapthyl.

The term "cycloalkoxy" as used herin refers to $R_{54}$O— wherein $R_{54}$ is cycloalkyl as defined above. Representative examples of alkoxy groups include cyclopropoxy, cyclopentyloxy, and cyclohexyloxy and the like.

The term "arylthio" herein refers to $R_{55}$S— wherein $R_{55}$ is an aryl group.

The term "alkylsulfinyl" herein refers to $R_{55}$—S(O)$_2$— wherein $R_{55}$ is as previously defined.

The term "carboxamido" herein refers to —C(O)NH$_2$.

The term "carbamoyl" herein refers to —O—C(O)NH$_2$.

The term "carboxyl" herein refers to —CO$_2$H.

The term "halogen" or "halo" as used herein refers to I, Br, Cl, or F. The term "haloalkyl" as used herein refers to a lower alkyl radical, as defined above, bearing at least one halogen substituent, for example, chloromethyl, fluoroethyl or trifluoromethyl and the like.

The term "haloalkyl" as used herein refers to a lower alkyl radical to which is appended one or more halogens. Representative examples of a haloalkyl group include trifluoromethyl, chloromethyl, 2-bromobutyl, 1-bromo-2-chloro-pentyl and the like.

The term "haloalkoxy" as used herin refers to a haloalkyl radical to which is appended an alkoxy group. Representative examples of haloalkoxy groups incluse fluoromethoxy, 1,1,1-trichloroethoxy, 2-bromobutoxy and the like.

The term "heteroaryl" as used herein refers to a mono- or bi-cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole and isoxazole.

The term "heterocyclic ring" refers to any 3-, 4-, 5-, 6-, or 7-membered nonaromatic ring containing at least one nitrogen atom, oxygen, or sulfur.

The term "arylheterocyclic ring" as used herein refers to a bi- or tricyclic ring comprised of an aryl ring as previously defined appended via two adjacent carbons of the aryl group to a heterocyclic ring as previously defined.

The term "heterocyclic compounds" herein refers to mono and polycyclic compounds containing at least one heteroaryl or heterocyclic ring.

Examples of contemplated steroids include beclamethasone, fluticasone, flunisolide, triamcinolone, butixocort, dexamethasone, fluocortin, budesonide, tixocortal, tipredane and mometasone. Examples of contemplated β-agonists include salmeterol, albuterol, metaproterenol, terbutaline, pirbuterol, rimiterol, clenbuterol, bitoterol and reproterol. Examples of contemplated anticholinergics include ipratropium, flutropium, tiotropium and rispenzepine. Examples of contemplated mast cell stabilizers include cromalyn and nedocromil. Examples of contemplated PDE inhibitors include filaminast, denbufyllene piclamilast, zardaverine, and rolipram.

Sources of information for the above include Goodman and Gilman, The Pharmacological Basis of Therapeutics (8th Ed.), McGraw-Hill, Inc., 1993; the Physician's Desk Reference (49th Ed.), Medical Economics (1995); Drug Facts and Comparisons (1993 Ed), Facts and Comparisons (1993); and The Merck Index (11th Ed.), Merck & Co., Inc. (1989), all of which are incorporated herein by reference in their entirety.

A principal aspect of the invention relates to novel nitrosated and/or nitrosylated compounds.

One embodiment of this aspect provides compounds having the structure:

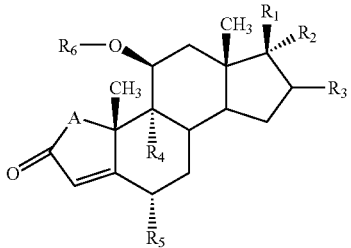

I wherein
A is selected from —CH═CH— or —CH$_2$—CH$_2$—;
$R_1$ is selected from
(1) —C(O)CH$_2$-B-D wherein B is oxygen or sulfur; D is selected from (i) —NO; (ii) —NO$_2$; (iii) —C($R_d$)—O—C(O)—Y—(C($R_e$)($R_f$))$_p$-T-Q in which $R_d$ is hydrogen, lower alkyl, cycloalkyl, aryl, alkylaryl, aryl or heteroaryl, Y is oxygen, sulfur, or NR$_i$ in which R$_i$ is hydrogen, lower alkyl, lower haloalkyl, or heteroaryl, $R_e$ and $R_f$ are independently selected from hydrogen, lower alkyl, cycloalkyl, aryl, heteroaryl, arylalkyl, alkylamino, dialkylamino, carboxy, or taken together are carbonyl, cycloalkyl or bridged cycloalkyl, p is an integer from 1 to 6, T is a covalent bond, oxygen, sulfur or nitrogen and Q is selected from —NO or —NO$_2$; (iv) —C(O)-T$^1$(C($R_e$)($R_f$))$_p$-T$^2$-Q wherein T$^1$ and T$^2$ are independently selected from T and $R_e$, $R_f$, p, Q, and T are as defined above; (v) —C(O)-T(C($R_y$)($R_z$))$_p$ wherein $R_y$ and $R_z$ are independently selected from -T$^1$-(C($R_e$)($R_f$))$_p$-G-(C($R_e$)($R_f$))$_p$-T$^2$-Q wherein G is (i) a covalent bond; (ii) -T-C(O)—; (iii) —C(O)-T, or (iv) Y, and wherein $R_d$, $R_e$, $R_f$, p, Q, T, and Y are as defined above;
(2) —C(O)—C(O)—O—R$_i$ wherein R$_i$ is as defined above;
(3) —C(O)—B—R$_i$ wherein B and R$_i$ are as defined above;
(4) —C(O)—CH$_2$—B—C(O)—R$_i$ wherein B and R$_i$ are as defined above;
(5) —C(O)—CH$_2$—X wherein X is halogen;
(6) —S—R$_i$ wherein R$_i$ is as defined above;

(7) —C(O)CH$_2$—B-M wherein M is selected from —C(O)T-(C($R_e$)($R_f$))$_p$-G-(C($R_e$)($R_f$))$_p$—N(N—(O$^-$)N═O)—R$_i$ or —C($R_d$)—O—C(O)T-(C($R_e$)($R_f$))$_p$-G-(C($R_e$)($R_f$))$_p$—N(N—(O$^-$)N═O)—R$_i$, wherein $R_e$, $R_f$, $R_i$, p, G and T are as defined above;

$R_2$ and $R_3$ are independently selected from hydrogen, hydroxyl, lower alkyl, —O(O)C—R$_i$, or —S—R$_i$ wherein R$_i$ is as defined above or $R_2$ and $R_3$ when taken together are

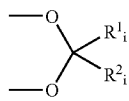

wherein R$^1_i$ and R$^2_i$ are independently selected from R$_i$ wherein R$_i$ is as defined above;
$R_4$ and $R_5$ are independently selected from hydrogen or halogen;
$R_6$ is selected from hydrogen, D, or M wherein D and M are as defined above with the provision that $R_6$ must be D or M if the selection for $R_1$ does not include D or M;

Another embodiment of this aspect provides compounds having the structure:

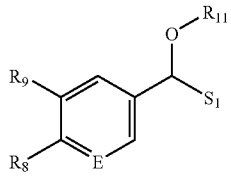

wherein,
E is nitrogen or C—R$_7$ wherein R$_7$ is hydrogen, halogen, —CH$_2$O—R$_j$, or —O—R$_j$ wherein R$_j$ is hydrogen, D or M wherein D and M are defined as above;
$R_8$ and $R_9$ are independently selected from amino, hydrogen, —CH$_2$O—R$_j$, or —O—R$_k$ wherein R$_k$ is —C(O)—R$_d$ or R$_j$ and R$_d$ and R$_j$ are as defined above; S$_1$ is (1) —CH$_2$—N(Z)-R$_{10}$ wherein Z is hydrogen, —(N(O)N═O), or M wherein M is as defined above and R$_{10}$ is selected from
(i) lower alkyl
(ii) —(CH$_2$)$_p$—O—(CH$_2$)$_a$—C$_6$H$_5$ wherein a is an integer from 1 to 4 and p is as defined above;

(III)

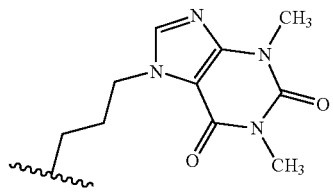

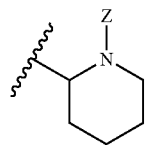

(2)

wherein Z is as defined above; and $R_{11}$ is selected from hydrogen, D, or M with the provision that $R_{11}$ must be D or M if neither $R_8$ or $R_9$ include D or M and Z is hydrogen;

Another embodiment of this aspect provides compounds having the structure: K is a a monovalent charged anion selected from halide, nitrate, or nitrite;

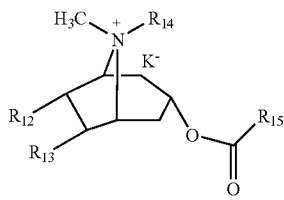

III wherein,

K is a a monovalent charged anion selected from halide, nitrate, or nitrite;

$R_{12}$ and $R_{13}$ are hydrogen or, when taken together are oxygen;

$R_{14}$ is lower alkyl or haloalkyl;

$R_{15}$ is selected from:

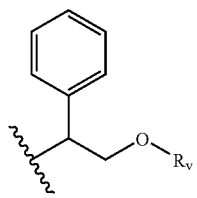

(i)

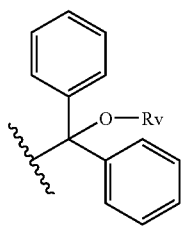

(ii)

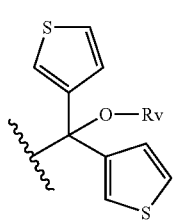

(iii)

wherein $R_v$ is selected from D or M and D and M are as defined above;

Another embodiment of this aspect provides compounds having the structure:

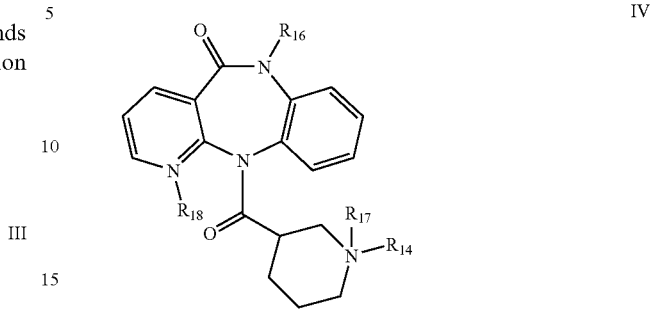

IV wherein $R_{14}$ is as defined above;

$R_{16}$ is selected from hydrogen, —C($R_d$)—O—C(O)—Y—(C($R_e$)($R_f$))$_p$-T-Q, —C(O)-T$^1$-(C($R_e$)($R_f$))$_p$-T$^2$-Q, or M; and wherein $R_d$, $R_e$, $R_f$, M, p, T, T$^1$, T$^2$, Q, and Y are defined as above; and $R_{17}$ and $R_{18}$ are independently selected from a lone pair of electrons, —C($R_d$)—O—C(O)—Y—(C($R_e$)($R_f$))$_p$-T-Q, or M wherein $R_d$, $R_e$, $R_f$, M, p, T, Q, and Y are defined as above with the provision that $R_{17}$ and/or $R_{18}$ must be —C($R_d$)—O—C(O)—Y—(C($R_e$)($R_f$))$_p$-T-Q or M when $R_{16}$ is hydrogen;

Another embodiment of this aspect provides compounds having the structure:

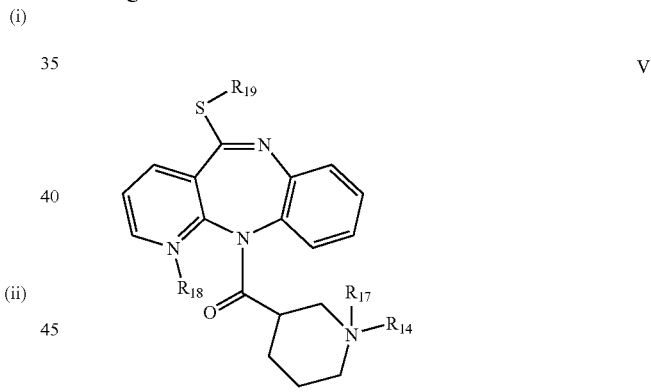

V wherein $R_{19}$ is selected from —(C($R_e$)($R_f$))$_p$-G-(C($R_e$)($R_f$))$_p$-T-Q or —S(O$_2$)—(C($R_e$)($R_f$))$_p$-G-(C($R_e$)($R_f$))$_p$—N(N—(O—)N=O)—$R_i$ wherein $R_e$, $R_f$, $R_i$, p, G, Q and T are as defined above; and wherein $R_{14}$, $R_{17}$, and $R_{18}$ are as defined above;

Another embodiment of this aspect provides compounds having the structure:

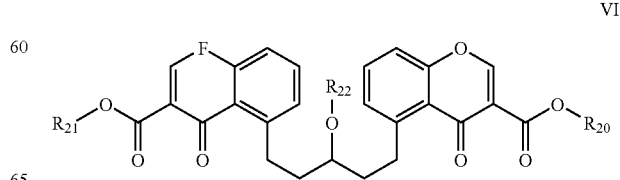

VI wherein,

F is selected from oxygen or $NR_i$ wherein $R_i$ is as defined above;

$R_{20}$ and $R_{21}$ are independently selected from (1) —Y—$(C(R_e)(R_f))_p$—H—$(C(R_e)(R_f))_p$-T-Q; wherein H is (i) a covalent bond; (ii) -T—C(O)—; (iii) —C(O)-T; (iv) —C(Y—C(O)—$R_m$)— wherein $R_m$ is heteroaryl or heterocyclic ring; and wherin Y, $R_d$, $R_e$, $R_f$, p, Q and T are as defined above; (2) T-$(C(R_e)(R_f))_p$—H—$(C(R_e)(R_f))_p$—N(N—(O—)N=O)—$R_i$ wherin $R_d$, $R_e$, $R_f$, $R_i$, p, H and T are as defined above; (3)

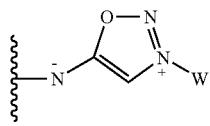

in which W is a heterocyclic ring or $NR_sR'_s$ wherein $R_s$ and $R'_s$ are independently selected from lower alkyl, aryl or alkenyl; (4) sodium or (5) hydrogen;

$R_{22}$ is hydrogen, M, or D with the provision that $R_{22}$ must be M or D when $R_{20}$ and $R_{21}$ are selected as sodium or hydrogen;

Another embodiment of this aspect provides compounds having the structure:

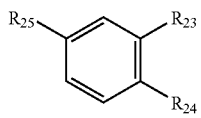

VII wherein, $R_{23}$ is alkoxy, cycloalkoxy, or halogen;
$R_{24}$ is hydrogen, alkoxy, or haloalkoxy; and
$R_{25}$ is selected from:

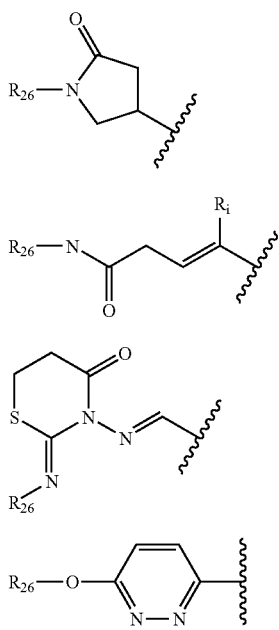

(i)

(ii)

(iii)

(iv)

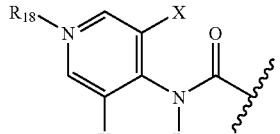

(v)

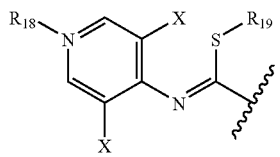

(vi)

wherein $R_{26}$ is selected from D or M and wherein $R_{16}$, $R_{18}$, and $R_{19}$ are defined as above.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the invention provides processes for making the novel compounds of the invention and to the intermediates useful in such processes.

Some of the compounds of the invention are synthesized as shown in FIGS. 1 through 29 presented below, in which A, E, F, W, $R_2$, $R_3$, $R_4$, $R_5$, $R_6$, $R_9$, $R_{10}$, $R_{12}$, $R_{13}$, $R_{14}$, $R_{17}$, $R_{18}$, $R_{21}$, $R_{22}$, $R_{23}$, $R_{24}$, $R_e$, $R_f$, p, and Z are as defined above or as depicted in the reaction schemes for structures I–VII; $P^1$ is an oxygen protecting group, $P^2$ is a sulfur protecting group and $P^3$ is a nitrogen protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur, oxygen, and nitrogen protecting groups is well known in the art for protecting thiol, alcohol, and amino groups against undesirable reactions during a synthetic procedure and many such protecting groups are known, c.f., T. H. Greene and P. G. M. Wuts, *Protective Groups in Organic Synthesis*, John Wiley & Sons, New York (1991).

One embodiment of this aspect provides processes for making compounds having structures I and to the intermediates useful in such processes as follows.

Nitroso compounds of formula (I) wherein A, $R_2$, $R_3$, $R_4$, $R_5$, $R_6$, $R_e$, $R_f$, and p are defined as above and an O-nitrosylated ester is representative of the $R_1$ group as defined above may be prepared as outlined in FIG. 1. The alcohol group of formula 1 is converted to the ester of formula 2 wherein p, $R_e$ and $R_f$ are defined as above by reaction with an appropriate protected alcohol containing activated acylating agent wherein $P^1$ is as defined above. Preferred methods for the formation of esters are reacting the alcohol with the preformed acid chloride or symmetrical anhydride of the protected alcohol containing acid or condensing the alcohol and protected alcohol containing acid in the presence of a dehydrating agent such as dicyclohexylcarbodiimide (DCC) or 1-ethyl-3(3-dimethylaminopropyl)carbodiimide hydrochloride (EDAC.HCl) with or without a catalyst such as dimethylaminopyridine (DMAP) or 1-hydroxybenzotriazole (HOBt). Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IA.

Figure 2:
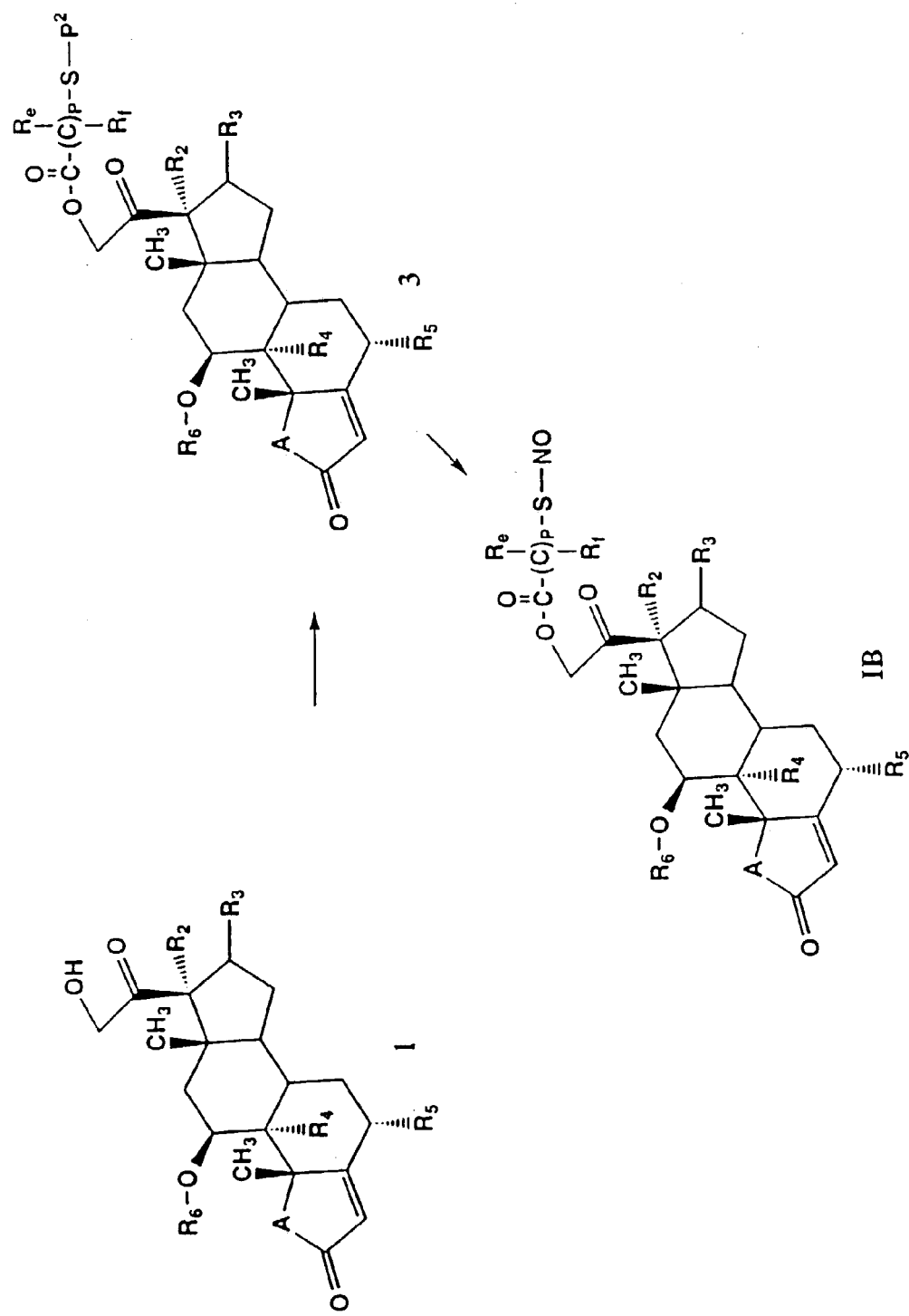
FIG. 2 illustrates a synthetic pathway for the preparation of nitrosothiol containing steriod derivatives.

Nitroso compounds of formula (I) wherein A, $R_2$, $R_3$, $R_4$, $R_5$, $R_6$, $R_e$, $R_f$, and p are defined as above and an S-nitrosylated ester is representative of the $R_1$ group as defined above may be prepared as outlined in FIG. 2. The alcohol group of the formula 1 is converted to the ester of the formula 3 wherein p, $R_e$ and $R_f$ are defined as above by reaction with an appropriate protected thiol containing activated acylating agent wherein $P^2$ is as defined above. Preferred methods for the formation of esters are reacting the alcohol with the preformed acid chloride or symmetrical anhydride of the protected thiol containing acid or condensing the alcohol and protected thiol containing acid in the presence of a dehydrating agent such as DCC or EDAC.HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IB. Alternatively, treatment of compound 3 with a stoichiometric quantity of sodium nitrite in an acidic aqueous or alcoholic solution affords the compound of the formula IB.

Figure 3:
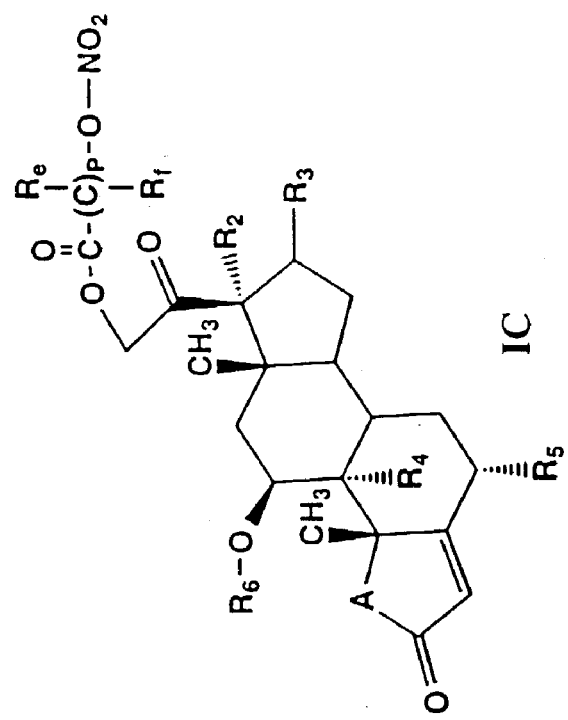
FIG. 3 illustrates a synthetic pathway for the preparation of nitrate containing steriod derivatives.
Figure 3:
Figure 3:
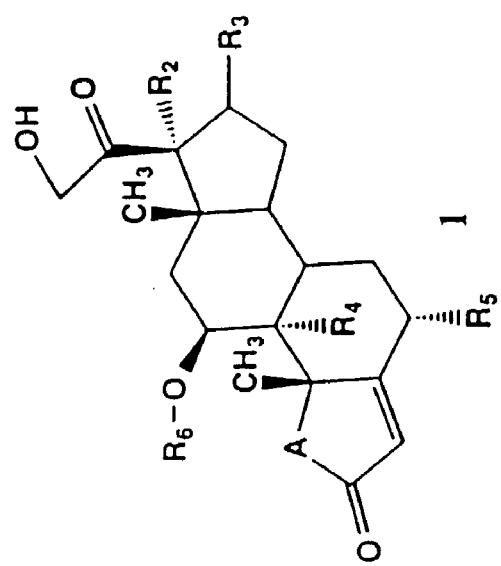

Nitro compounds of formula (I) wherein A, $R_2$, $R_3$, $R_4$, $R_5$, $R_6$, $R_e$, $R_f$, and p are defined as above and an O-nitrosated ester is representative of the $R_1$ group as defined above may be prepared as outlined in FIG. 3. The alcohol group of the formula 1 is converted to the ester of the formula IC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent such as DCC or EDAC.HCl with or without a catalyst such as DMAP or HOBt to afford a compound of the formula IC.

Figure 4:
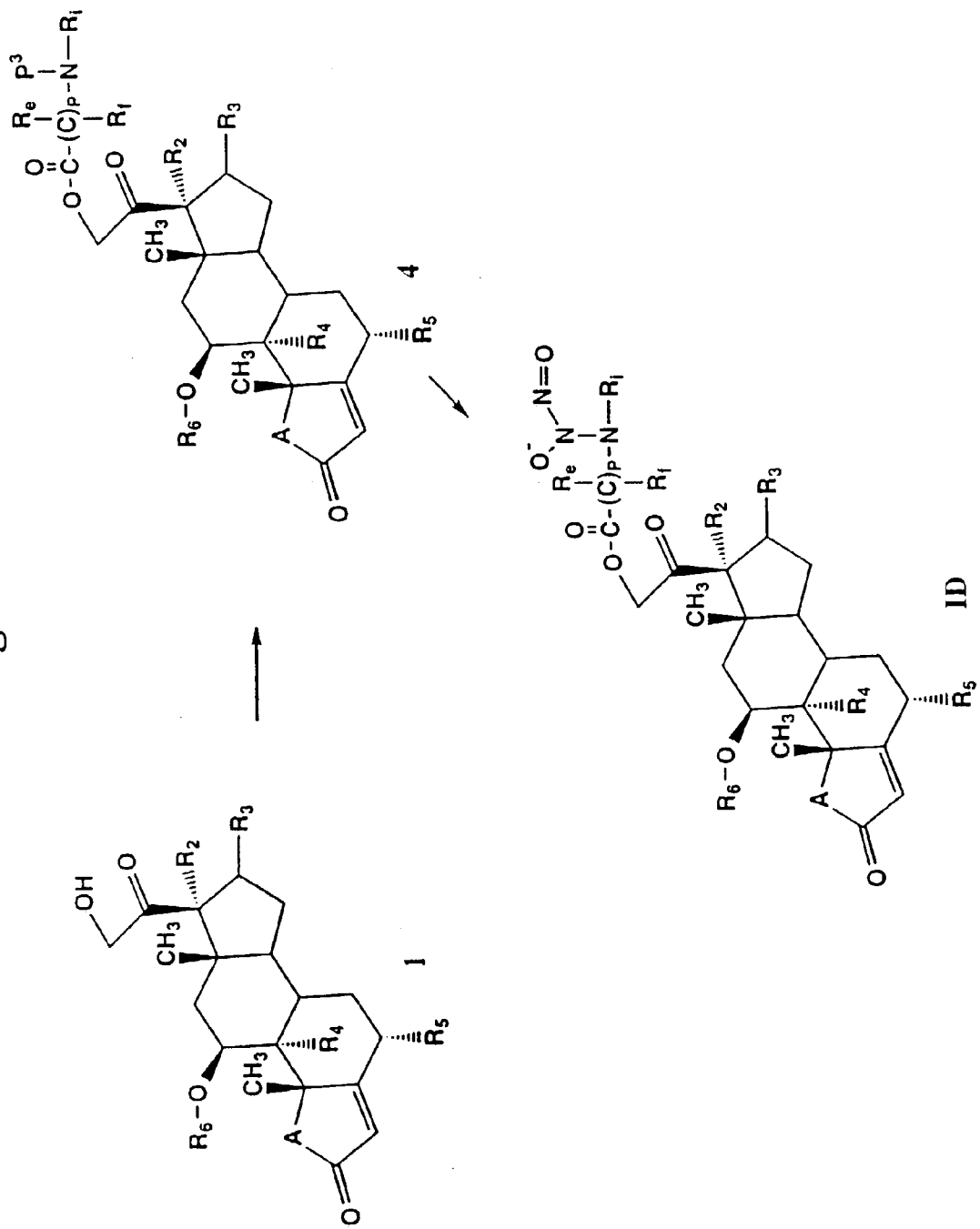
FIG. 4 illustrates a synthetic pathway for the preparation of 2-hydroxy-2-nitrosohydrazine containing steriod derivatives.

2-Hydroxy-2-nitrosohydrazine compounds of formula (I) wherein A, $R_2$, $R_3$, $R_4$, $R_5$, $R_6$, $R_e$, $R_f$ $R_i$ and p are defined as above and a 2-hydroxy-2-nitrosohydrazine ester is representative of the $R_1$ group as defined above may be prepared as outlined in FIG. 4. The alcohol group of the formula 1 is converted to the ester of the formula 4 wherein p, $R_e$, $R_f$, and $R_i$ are defined as above by reaction with an appropriate protected amino containing activated acylating agent wherein $P^3$ is as defined above. Preferred methods for the formation of esters are reacting the alcohol with the preformed acid chloride or symmetrical anhydride of the protected amino containing acid or condensing the alcohol and protected amine containing acid in the presence of a dehydrating agent such as DCC or EDAC.HCl with or without a catalyst such as DMAP or HOBt. Preferred protecting groups for the amine are as a carbamate such as a t-butyl carbamate or a 9-fluorenylmethyl carbamate or an amide such as a trifluoroacetamide. Deprotection of the amino moiety (strong acid such as HCl in dioxane or trifluoroacetic acid is used to remove a t-butyl carbamate while piperidine is used to remove 9-fluorenylmethyl carbamate while mild aqueous or alcoholic base may be used to cleave a trifluoroacetamide group) followed by treatment of the amine with nitric oxide (1–5 atmospheres) in a dry inert solvent such as ether or tetrahydrofuran affords the compound of the formula ID.

Another embodiment of this aspect provides processes for making compounds having structures II and to the intermediates useful in such processes as follows.

Figure 5:
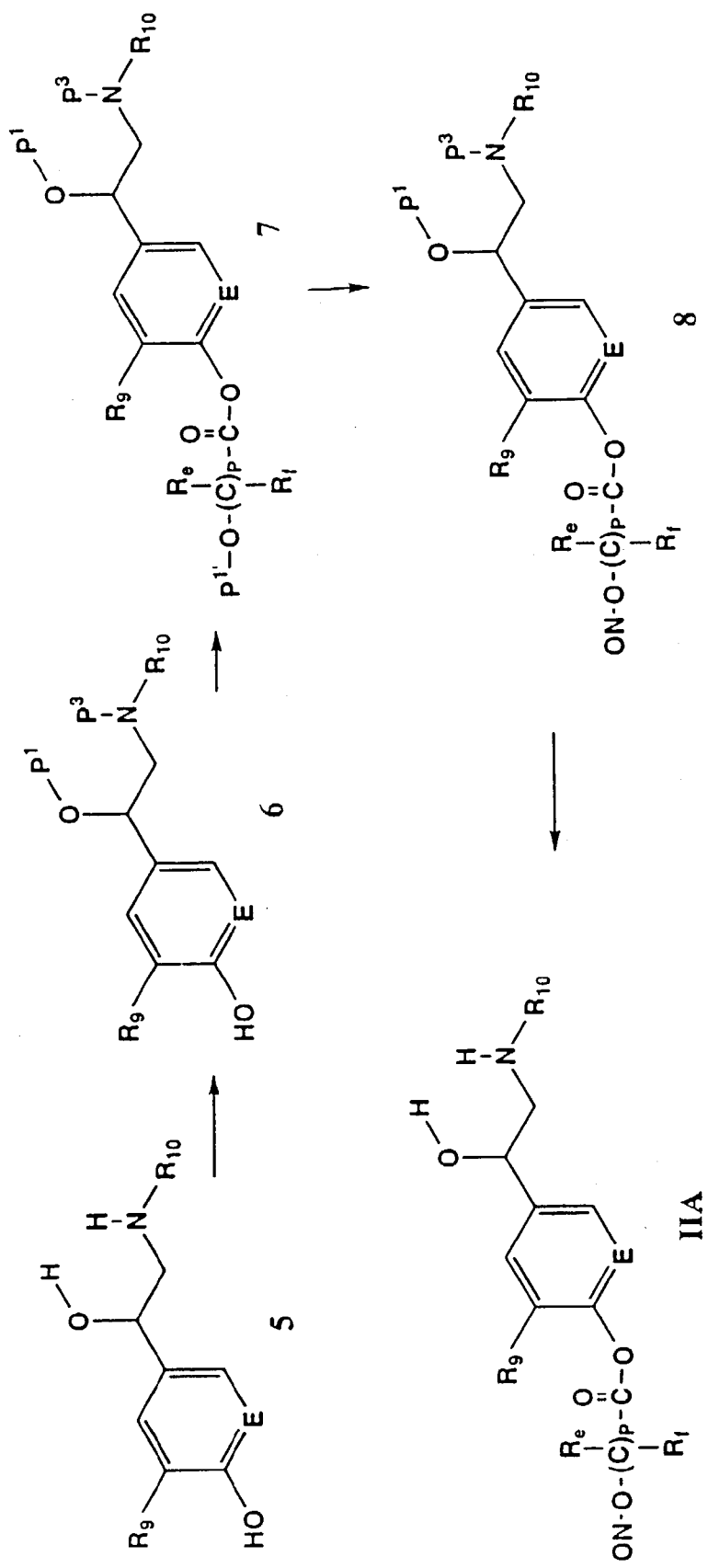
FIG. 5 illustrates a synthetic pathway for the preparation of nitrite containing β-agonist derivatives.

Nitroso compounds of formula (II) wherein E, $R_9$, $R_{10}$, $R_e$, $R_f$, and p are defined as above, Z and $R_{11}$ are hydrogen, and an O-nitrosylated ester is representative of the $R_8$ group as defined above may be prepared as outlined in FIG. 5. The amine, 1°, and 2° alcohol groups of formula 5 are protected to afford the compound of the formula 6. Preferred protecting groups for the amine are as a carbamate such as a benzyl carbamate or an amide such as a trifluoroacetamide while preferred protecting groups for 1° and 2° alcohol moieties are as benzyl ethers. The phenolic group(s) of formula 6 is converted to the ester(s) of formula 7 wherein p, $R_e$ and $R_f$ are defined as above by reaction with an appropriate protected alcohol containing activated acylating agent wherein $P^1$ is as defined above. Preferred methods for the formation of esters are reacting the alcohol with the preformed acid chloride or symmetrical anhydride of the protected alcohol containing acid or condensing the alcohol and protected alcohol containing acid in the presence of a dehydrating agent such as DCC or EDAC.HCl with or without a catalyst such as DMAP or HOBt. Preferred protecting groups for the alcohol moiety are silyl ethers such as a trimethylsilyl or tert-butyldimethylsilyl ether. Deprotection of the hydroxyl moieties (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula 8. The compound of the formula 8 is then converted to the compound of the formula IIA by deprotecting the amine and remaining hydroxyl groups. Hydrogen in the presence of a transition metal catalyst such as palladium or platinum is a preferred method for removing benzyl ether and benzyl carbamate protecting groups.

Figure 6:
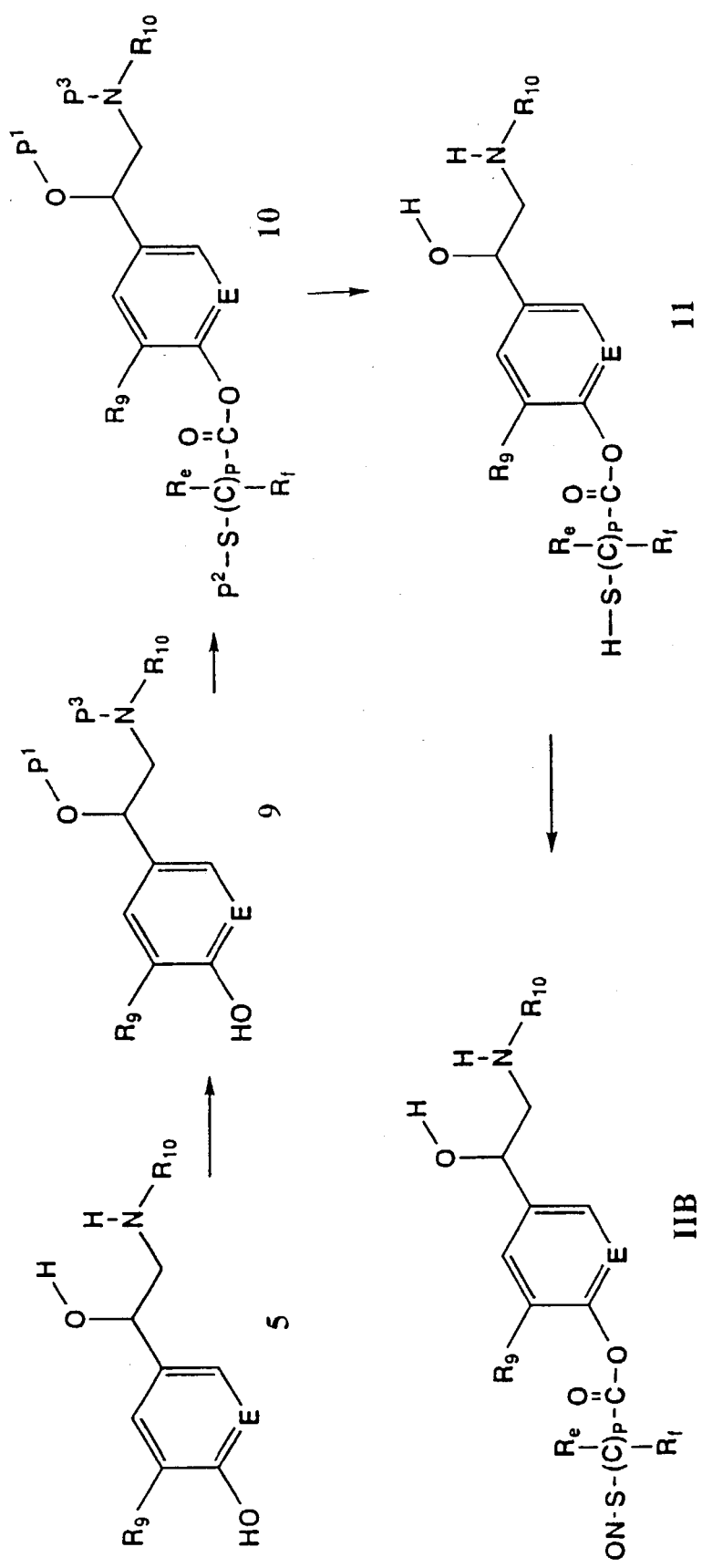
FIG. 6 illustrates a synthetic pathway for the preparation of nitrosothiol containing β-agonist derivatives.

Nitroso compounds of formula (II) wherein E, $R_9$, $R_{10}$, $R_e$, $R_f$, and p are defined as above, Z and $R_{11}$ are hydrogen, and a S-nitrosylated ester is representative of the $R_8$ group as defined above may be prepared as outlined in FIG. 6. The amine, 1°, and 2° alcohol groups of formula 5 are protected to afford the compound of the formula 9. Preferred protecting groups for the amine are as a carbamate such as a t-butyl carbamate or an amide such as a trifluoroacetamide while preferred protecting groups for 1° and 2° alcohol moieties are as silyl ethers such as trimethylsilyl or t-butyldimethylsilyl ethers. The phenolic group(s) of the formula 9 is converted to the ester(s) of the formula 10 wherein p, $R_e$ and $R_f$ are defined as above by reaction with an appropriate protected thiol containing activated acylating agent wherein $P^2$ is as defined above. Preferred methods for the formation of esters are reacting the alcohol with the preformed acid chloride or symmetrical anhydride of the protected thiol containing acid or condensing the alcohol and protected thiol containing acid in the presence of a dehydrating agent such as DCC or EDAC.HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4, 6-trimethoxybenzyl thioether. Deprotection of the amine (strong acid such as HCl in dioxane or trifluoroacetic acid is used to remove a t-butyl carbamate while mild aqueous or alcoholic base is used to cleave trifluoroacetamide groups) and hydroxyl moieties (fluoride ion is the preferred method for removing silyl ether protecting groups) followed by deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a 2,4,6-trimethoxybenzyl thioether group) affords a compound of the formula 11. Reaction of the compound of the formula 11 with a an eqimolar equivalent based upon thiol of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIB. Alternatively, treatment of compound 11 with a stoichiometric quantity of sodium nitrite in an acidic aqueous or alcoholic solution affords the compound of the formula IIB.

Figure 7:
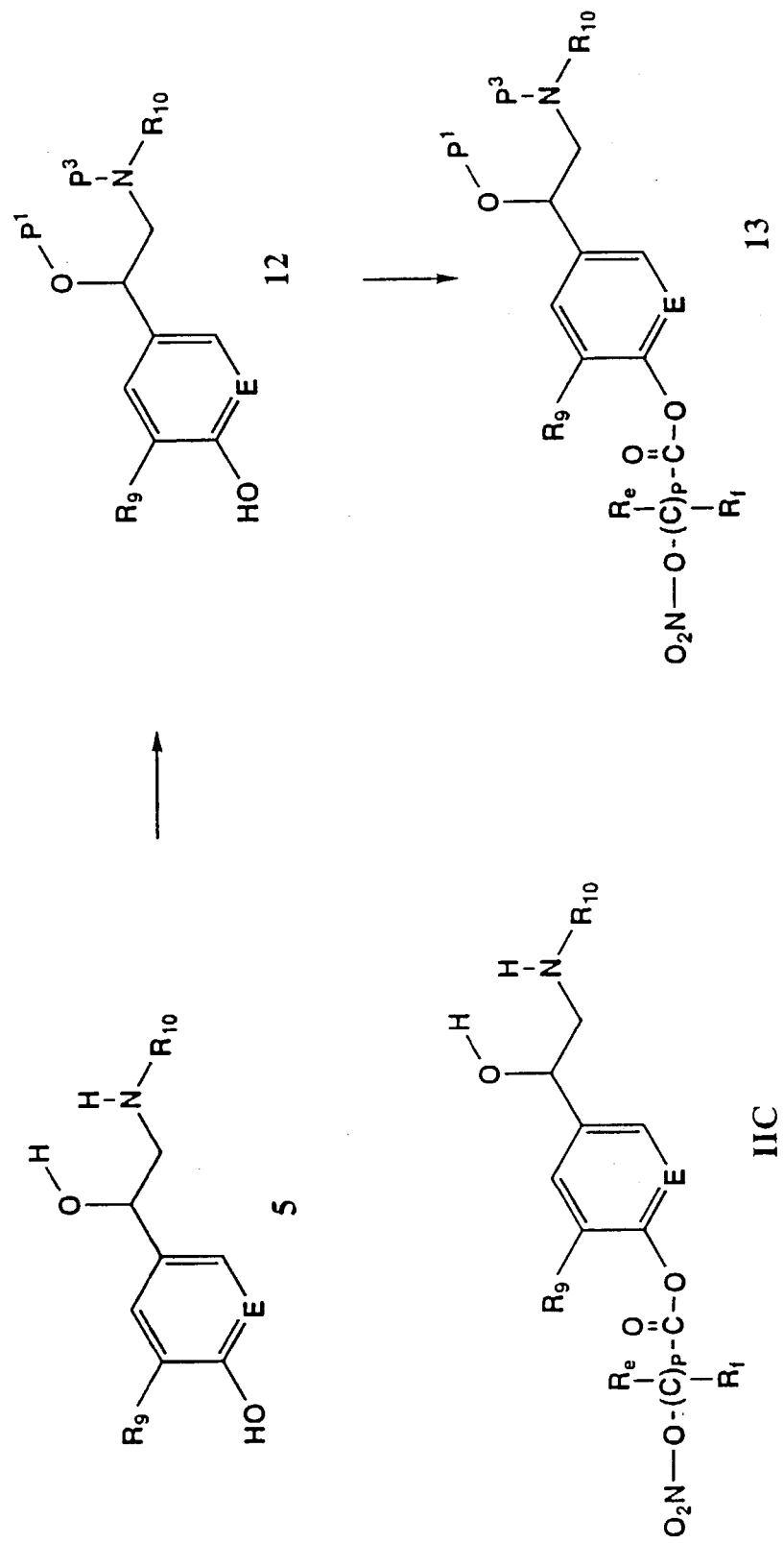
FIG. 7 illustrates a synthetic pathway for the preparation of nitrate containing β-agonist derivatives.

Nitro compounds of formula (II) wherein E, $R_9$, $R_{10}$, $R_e$, $R_f$, and p are defined as above, Z and $R_{11}$ are hydrogen, and a O-nitrosated ester is representative of the $R_8$ group as defined above may be prepared as outlined in FIG. 7. The amine, 1°, and 2° alcohol groups of formula 5 are protected to afford the compound of the formula 12. Preferred protecting groups for the amine are as a carbamate such as a t-butyl carbamate or an amide such as a trifluoroacetamide while preferred protecting groups for 1° and 2° alcohol moieties are as silyl ethers such as trimethylsilyl or t-butyldimethylsilyl ethers. The phenolic group(s) of the formula 12 is converted to the ester(s) of the formula 13 wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the protected thiol containing acid or condensing the alcohol and protected thiol containing acid in the presence of a dehydrating agent such as DCC or EDAC.HCl with or without a catalyst such as DMAP or HOBt. Deprotection of the amine (strong acid such as HCl in dioxane or trifluoroacetic acid is used to remove a t-butyl carbamate) and hydroxyl moieties (fluoride ion is the preferred method for removing silyl ether protecting groups) affords a compound of the formula IIC.

Figure 8:
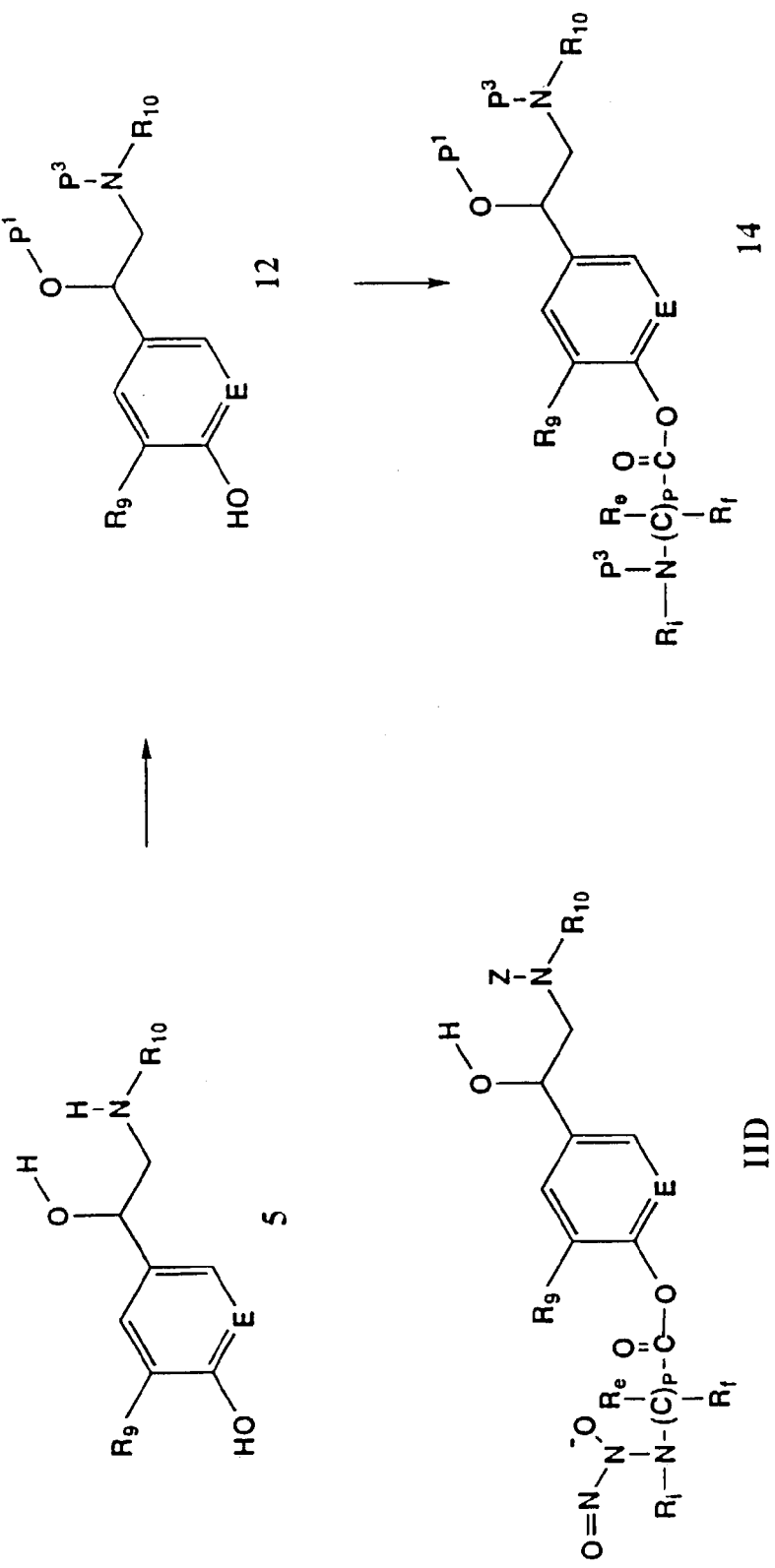
FIG. 8 illustrates a synthetic pathway for the preparation of 2-hydroxy-2-nitrosohydrazine containing β-agonist derivatives.

2-Hydroxy-2-nitrosohydrazine compounds of formula (II) wherein E, Z, $R_9$, $R_{10}$, $R_e$, $R_f$, $R_i$, and p are defined as above and a 2-hydroxy-2-nitrosohydrazine ester is representative of the $R_8$ group as defined above may be prepared as outlined in FIG. 8. The amine, 1°, and 2° alcohol groups of formula 5 are protected to afford the compound of the formula 12. Preferred protecting groups for the amine are as a carbamate such as a t-butyl carbamate or an amide such as a trifluoroacetamide while preferred protecting groups for 1° and 2° alcohol moieties are as silyl ethers such as trimethylsilyl or t-butyldimethylsilyl ethers. The phenolic group(s) of the formula 12 is converted to the ester of the formula 14 wherein p, $R_e$ and $R_f$ are defined as above by reaction with an appropriate protected amino containing activated acylating agent wherein $P^3$ is as defined above. Preferred methods for the formation of esters are reacting the alcohol with the preformed acid chloride or symmetrical anhydride of the protected amino containing acid or condensing the alcohol and protected amine containing acid in the presence of a dehydrating agent such as DCC or EDAC.HCl with or without a catalyst such as DMAP or HOBt. Preferred protecting groups for the amine are as a carbamate such as a t-butyl carbamate or an amide such as a trifluoroacetamide. Deprotection of the amine(s) (strong acid such as HCl in dioxane or trifluoroacetic acid is used to remove a t-butyl carbamate while mild aqueous or alcoholic base is used to cleave trifluoroacetamide groups) and hydroxyl moieties (fluoride ion is the preferred method for removing silyl ether protecting groups) followed by treatment of the amine(s) with nitric oxide (1–5 atmospheres) in a dry inert solvent such as ether or tetrahydrofuran affords the compound of the formula IID.

Another embodiment of this aspect provides processes for making compounds having structures III and to the intermediates useful in such processes as follows.

Figure 9:
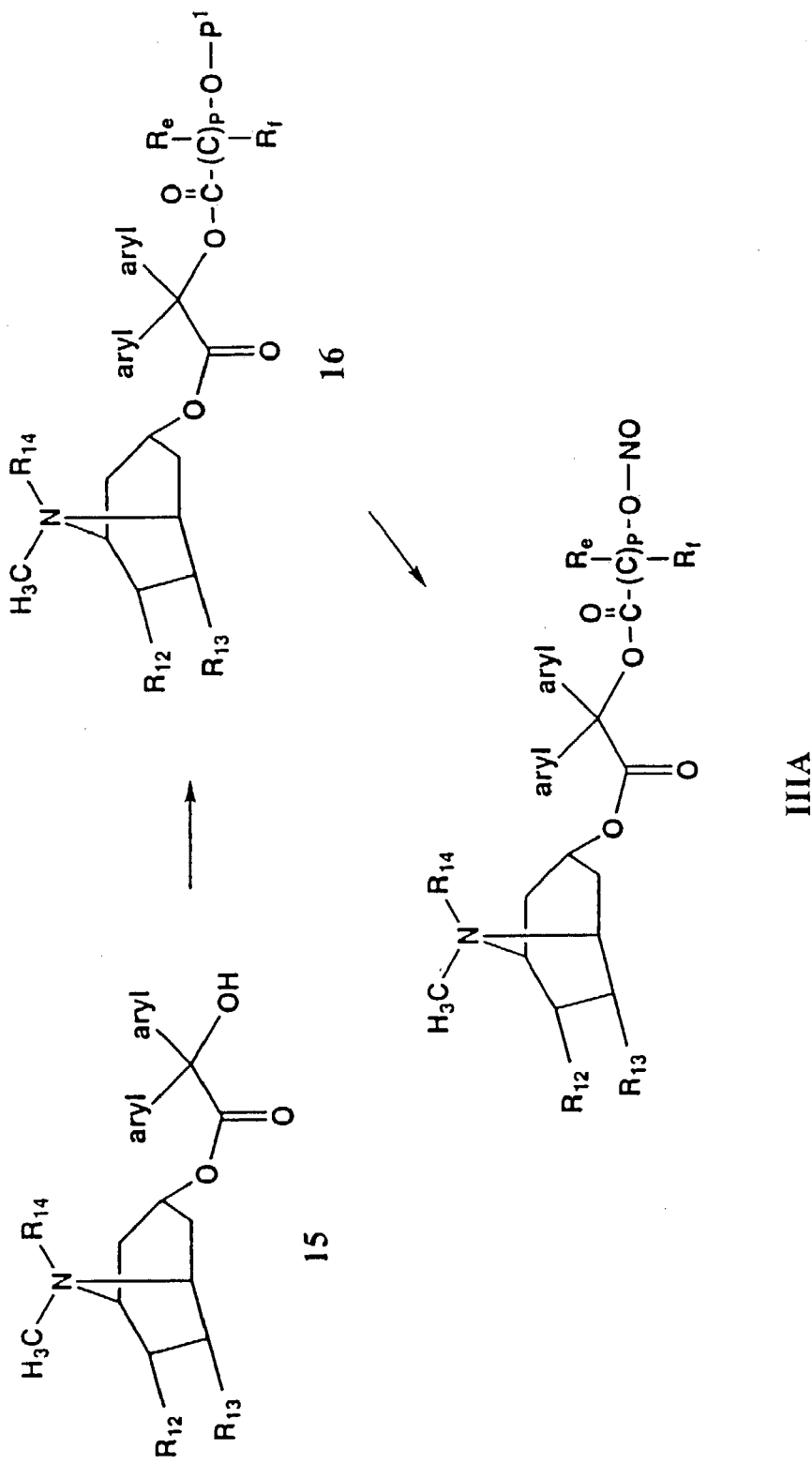
FIG. 9 illustrates a synthetic pathway for the preparation of nitrite containing anticholinergic derivatives.

Nitroso compounds of formula (III) wherein aryl, heteroaryl, $R_{12}$, $R_{13}$, $R_{14}$, $R_e$, $R_f$ and p are defined as above and an O-nitrosylated ester is representative of the $R_{15}$ group as defined above may be prepared as outlined in FIG. 9. The alcohol group of formula 15 is converted to the ester of formula 16 wherein p, $R_e$ and $R_f$ are defined as above by reaction with an appropriate protected alcohol containing activated acylating agent wherein $P^1$ is as defined above. Preferred methods for the formation of esters are reacting the alcohol with the preformed acid chloride or symmetrical anhydride of the protected alcohol containing acid or condensing the alcohol and protected alcohol containing acid in the presence of a dehydrating agent such as DCC or EDAC.HCl with or without a catalyst such as DMAP or HOBt. Preferred protecting groups for the alcohol moiety are silyl ethers such as a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IIIA.

Figure 10:
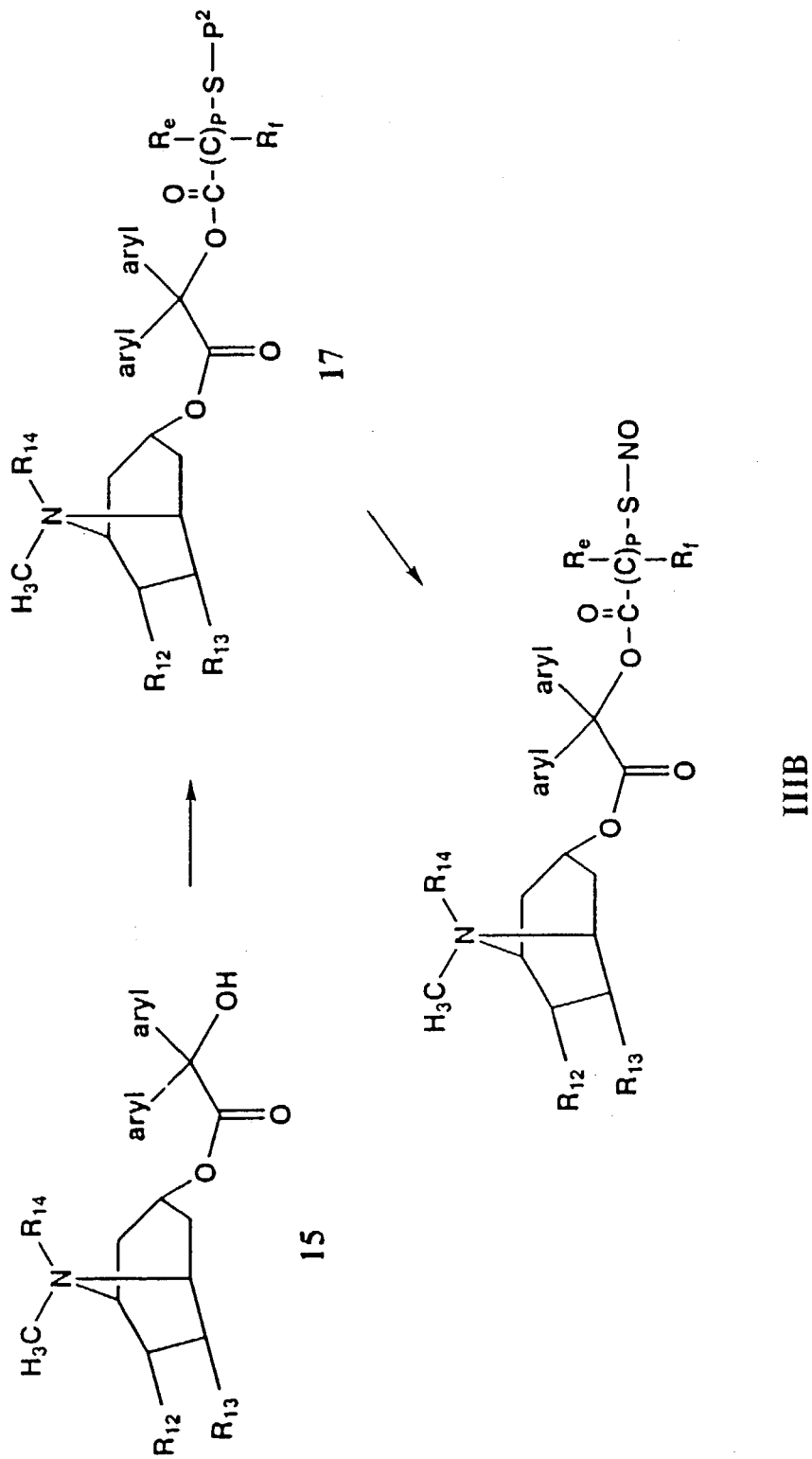
FIG. 10 illustrates a synthetic pathway for the preparation of nitrosothiol containing anticholinergic derivatives.

Nitroso compounds of formula (III) wherein aryl, heteroaryl, $R_{12}$, $R_{13}$, $R_{14}$, $R_e$, $R_f$, and p are defined as above and an S-nitrosylated ester is representative of the $R_{15}$ group as defined above may be prepared as outlined in FIG. 10. The alcohol group of the formula 15 is converted to the ester of the formula 17 wherein p, $R_e$ and $R_f$ are defined as above by reaction with an appropriate protected thiol containing activated acylating agent wherein $P^2$ is as defined above. Preferred methods for the formation of esters are reacting the alcohol with the preformed acid chloride or symmetrical anhydride of the protected thiol containing acid or condensing the alcohol and protected thiol containing acid in the presence of a dehydrating agent such as DCC or EDAC.HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IIIB. Alternatively, treatment of compound 17 with a stoichiometric quantity of sodium nitrite in an acidic aqueous or alcoholic solution affords the compound of the formula IIIB.

Figure 11:
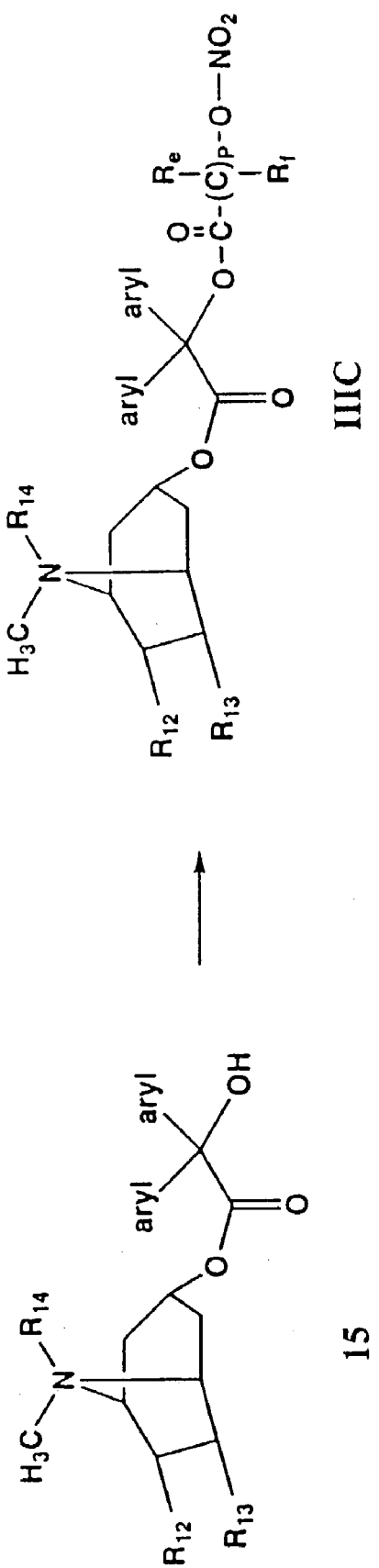
FIG. 11 illustrates a synthetic pathway for the preparation of nitrate containing anticholinergic derivatives.

Nitro compounds defined ester of formula (III) wherein aryl, heteroaryl, $R_{12}$, $R_{13}$, $R_{14}$, $R_e$, $R_f$, and p are defined as above and an O-nitrosated ester is representative of the $R_{15}$ group as defined above may be prepared as outlined in FIG. 11. The alcohol group of the formula 15 is converted to the ester of the formula IIIC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent such as DCC or EDAC.HCl with or without a catalyst such as DMAP or HOBt to afford a compound of the formula IIIC.

Figure 12:
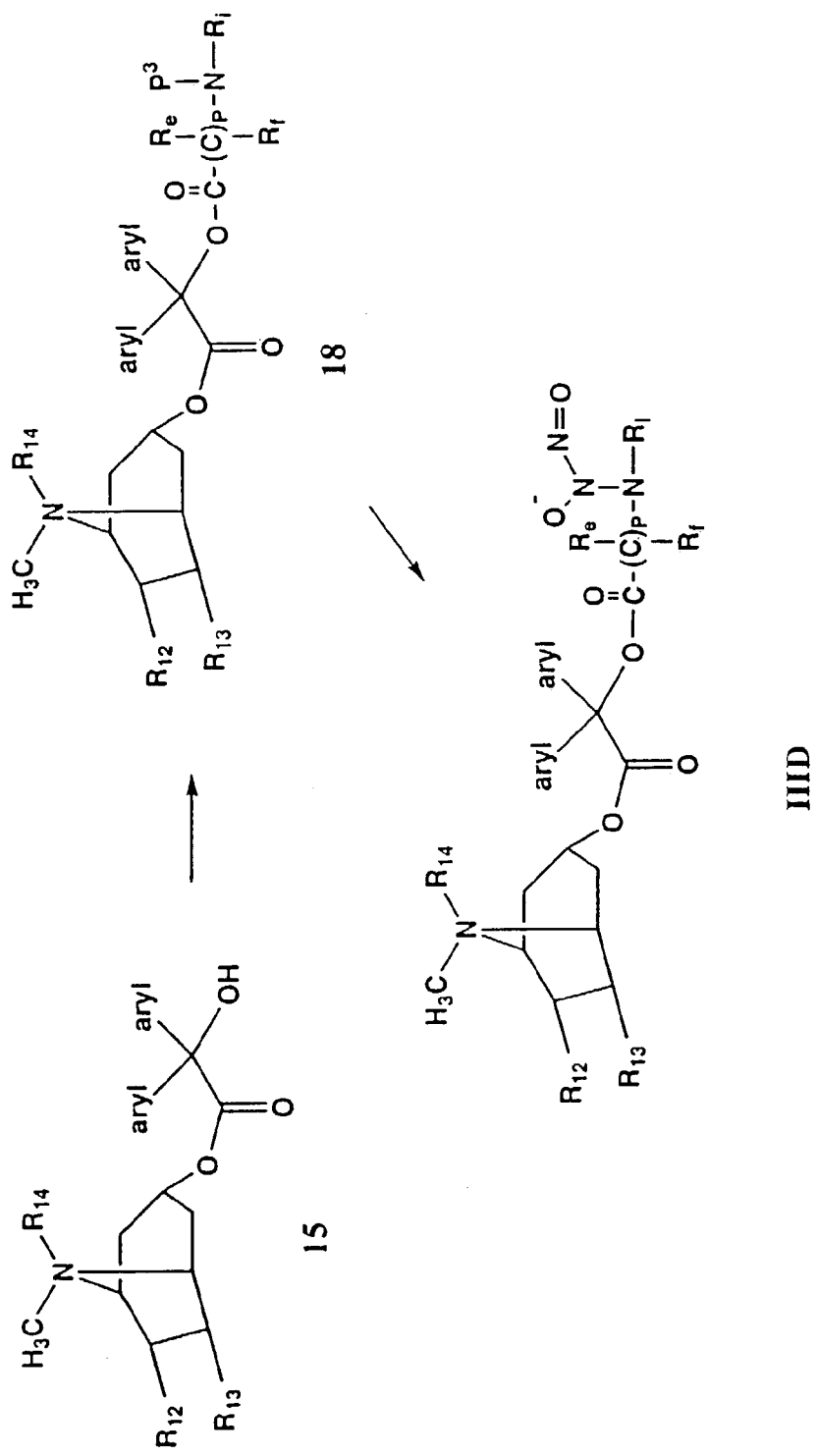
FIG. 12 illustrates a synthetic pathway for the preparation of 2-hydroxy-2-nitrosohydrazine containing anticholinergic derivatives.

2-Hydroxy-2-nitrosohydrazine compounds of formula (III) wherein aryl, heteroaryl, $R_{12}$, $R_{13}$, $R_{14}$, $R_e$, $R_f$, $R_i$, and p are defined as above and a 2-hydroxy-2-nitrosohydrazine ester is representative of the $R_{15}$ group as defined above may be prepared as outlined in FIG. 12. The alcohol group of the formula 15 is converted to the ester of the formula 18 wherein p, $R_e$, $R_f$, and $R_i$ are defined as above by reaction with an appropriate protected amino containing activated acylating agent wherein $P^3$ is as defined above. Preferred methods for the formation of esters are reacting the alcohol with the preformed acid chloride or symmetrical anhydride of the protected amino containing acid or condensing the alcohol and protected amine containing acid in the presence of a dehydrating agent such as DCC or EDAC.HCl with or without a catalyst such as DMAP or HOBt. Preferred protecting groups for the amine are as a carbamate such as a t-butyl carbamate or a 9-fluorenylmethyl carbamate or an amide such as a trifluoroacetamide. Deprotection of the amino moiety (strong acid such as HCl in dioxane or trifluoroacetic acid is used to remove a t-butyl carbamate while piperidine is used to remove 9-fluorenylmethyl carbamate while mild aqueous or alcoholic base may be used to cleave a trifluoroacetamide group) followed by treatment of the amine with nitric oxide (1–5 atmospheres) in a dry inert solvent such as ether or tetrahydrofuran affords the compound of the formula IIID.

Another embodiment of this aspect provides processes for making compounds having structures IV and to the intermediates useful in such processes as follows.

Figure 13:
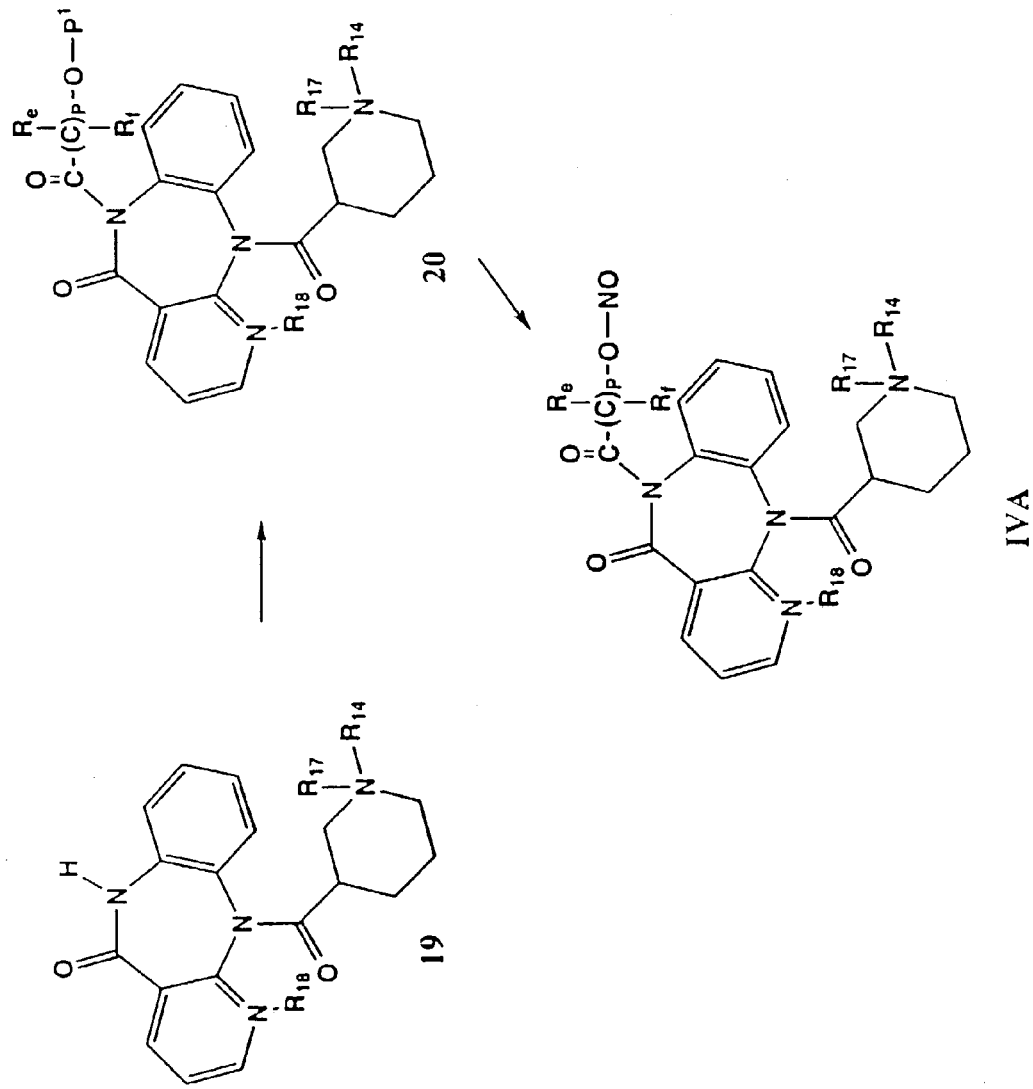
FIG. 13 illustrates a synthetic pathway for the preparation of nitrite containing rispenzepine derivatives.

Nitroso compounds of formula (IV) wherein $R_{14}$, $R_{17}$, $R_{18}$, $R_e$, $R_f$, and p are defined as above and an O-nitrosylated imide is representative of the $R_{16}$ group as defined above may be prepared as outlined in FIG. 13. The amide nitrogen of formula 19 is converted to the imide of formula 20 wherein p, $R_e$ and $R_f$ are defined as above by reaction with an appropriate protected alcohol containing activated acylating agent wherein $P^1$ is as defined above. Preferred methods for the formation of imides are reacting the alcohol with the preformed acid chloride or symmetrical anhydride of the protected thiol containing acid or condensing the alcohol and protected thiol containing acid in the presence of a dehydrating agent such as DCC or EDAC.HCl with a catalyst such as DMAP. Preferred protecting groups for the alcohol moiety are silyl ethers such as a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula IVA.

Figure 14:
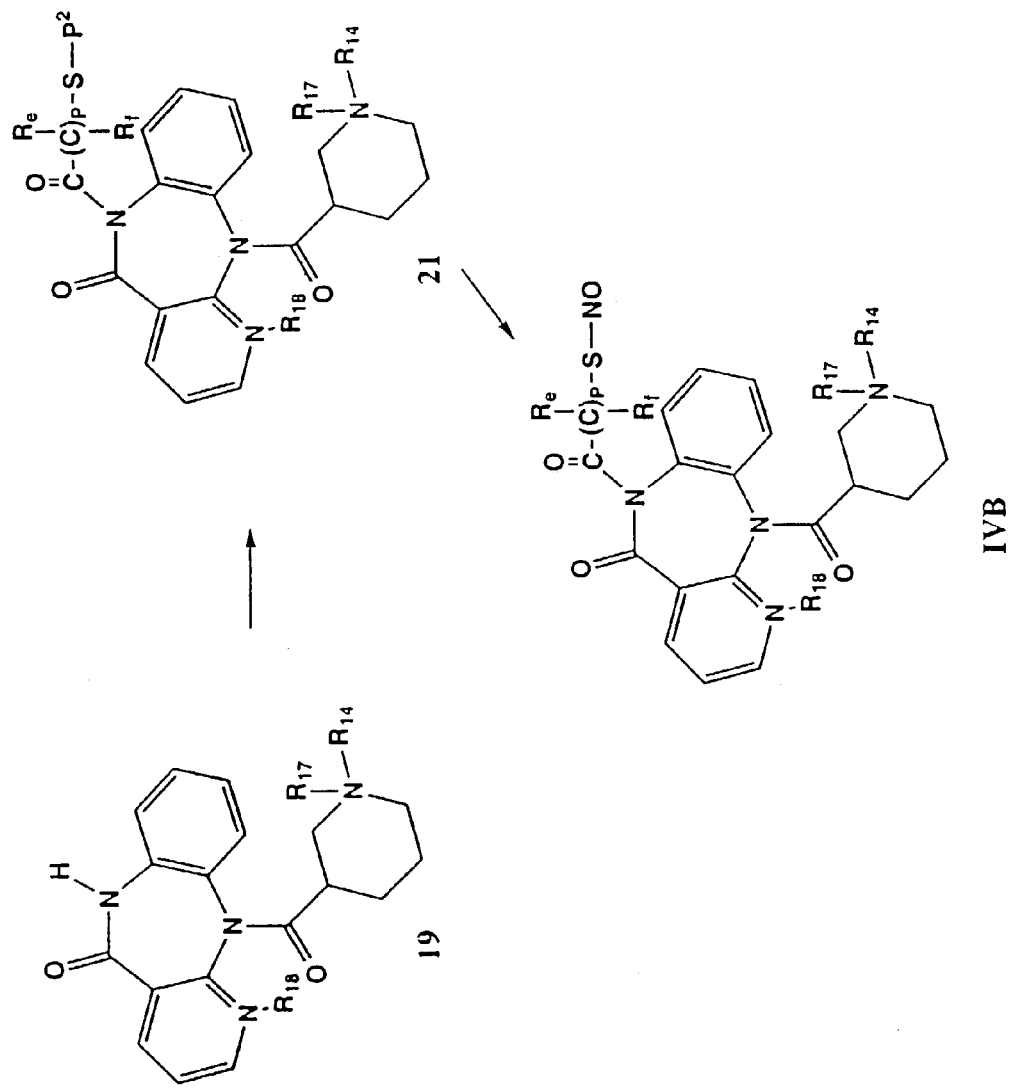
FIG. 14 illustrates a synthetic pathway for the preparation of nitrosothiol containing rispenzepine derivatives.

Nitroso compounds of formula (IV) wherein $R_{14}$, $R_{17}$, $R_{18}$, $R_e$, $R_f$, and p are defined as above and an S-nitrosylated imide is representative of the $R_{16}$ group as defined above may be prepared as outlined in FIG. 14. The amide nitrogen of formula 19 is converted to the imide of the formula 21 wherein p, $R_e$ and $R_f$ are defined as above by reaction with an appropriate protected thiol containing activated acylating agent wherein $P^2$ is as defined above. Preferred methods for the formation of imides are reacting the alcohol with the preformed acid chloride or symmetrical anhydride of the protected thiol containing acid or condensing the alcohol and protected thiol containing acid in the presence of a dehydrating agent such as DCC or EDAC.HCl with a catalyst such as DMAP. Preferred protecting groups for the thiol moiety are as a thioester such as a thioacetate or thiobenzoate, as a disulfide, or as a thioether such as a paramethoxybenzyl thioether, a tetrahydropyranyl thioether or a 2,4,6-trimethoxybenzyl thioether. Deprotect ion of the thiol moiety (zinc in dilute aqueous acid, triphenylphosphine in water and sodium borohydride are preferred methods for reducing disulfide groups while mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula IVB. Alternatively, treatment of compound 21 with a stoichiometric quantity of sodium nitrite in an acidic aqueous or alcoholic solution affords the compound of the formula IVB.

Figure 15:
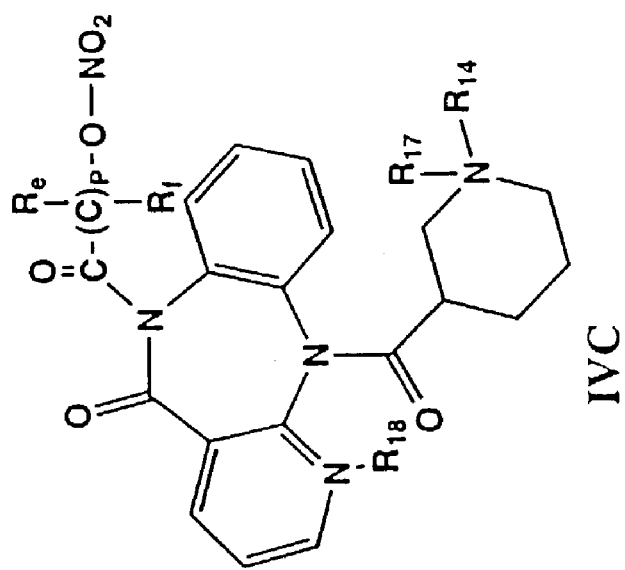
FIG. 15 illustrates a synthetic pathway for the preparation of nitrate containing rispenzepine derivatives.
Figure 15:
Figure 15:
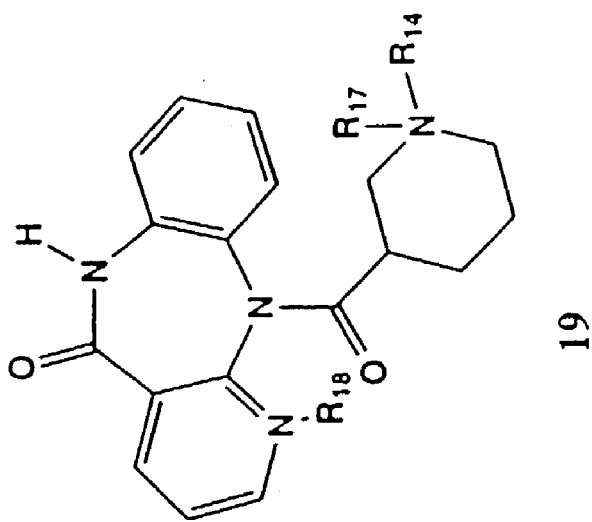

Nitro compounds of formula (IV) wherein $R_{14}$, $R_{17}$, $R_{18}$, $R_e$, $R_f$ and p are defined as above and an O-nitrosated imide is representative of the $R_{16}$ group as defined above may be prepared as outlined in FIG. 15. The amide of the formula 19 is converted to the imide of the formula IVC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent such as DCC or EDAC HCl with a catalyst such as DMAP to afford a compound of the formula IVC.

Figure 16:
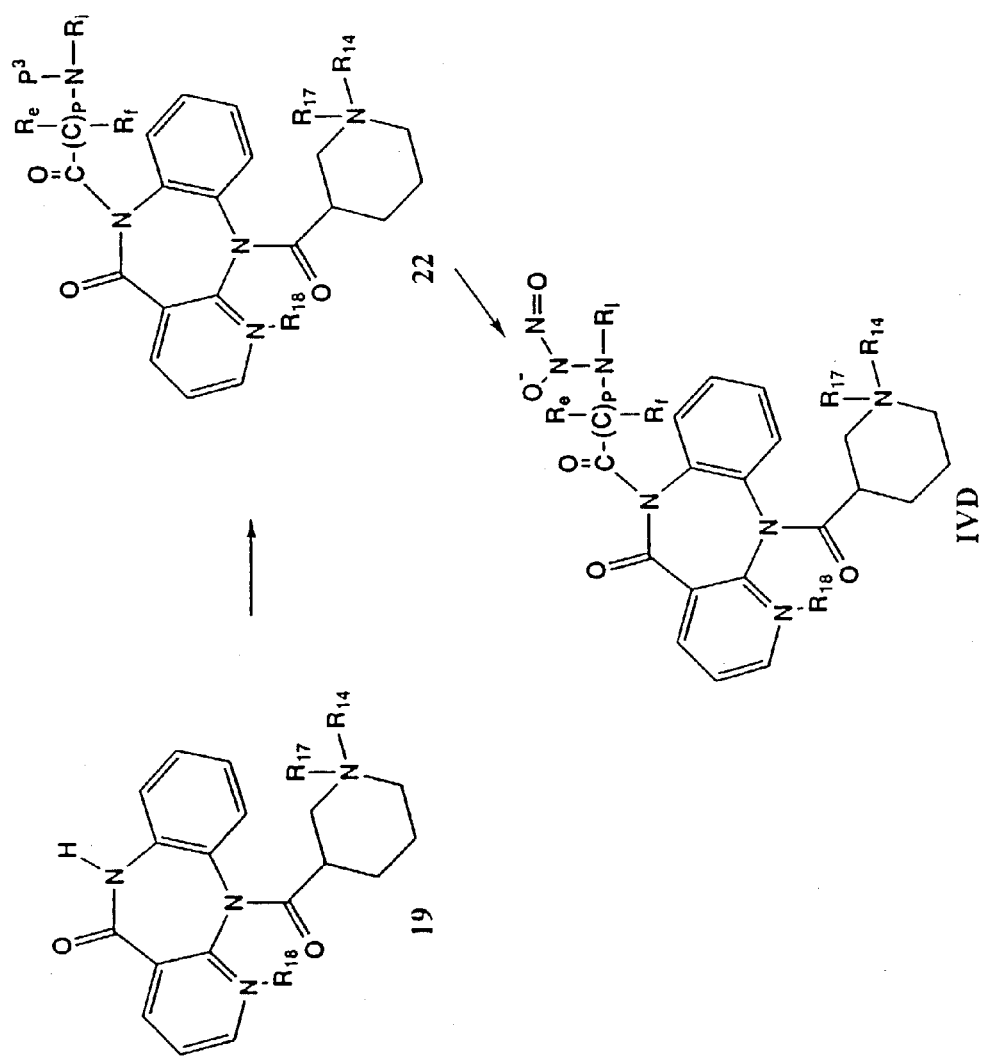
FIG. 16 illustrates a synthetic pathway for the preparation of 2-hydroxy-2-nitrosohydrazine containing rispenzepine derivatives.

2-Hydroxy-2-nitrosohydrazine compounds of formula (IV) wherein $R_{14}$, $R_{17}$, $R_{18}$, $R_e$, $R_f$, $R_i$, and p are defined as above and a 2-hydroxy-2-nitrosohydrazine imide is representative of the $R_{16}$ group as defined above may be prepared as outlined in FIG. 16. The amide nitrogen of the formula 19 is converted to the imide of the formula 22 wherein p, $R_e$, $R_f$, and $R_i$ are defined as above by reaction with an appropriate protected amino containing activated acylating agent wherein $P^3$ is as defined above. Preferred methods for the formation of imides are reacting the amide with the preformed acid chloride or symmetrical anhydride of the protected amino containing acid or condensing the alcohol and protected amine containing acid in the presence of a dehydrating agent such as DCC or EDAC.HCl with a catalyst such as DMAP. Preferred protecting groups for the amine are as a carbamate such as a t-butyl carbamate or a 9-fluorenylmethyl carbamate. Deprotection of the amino moiety (strong acid such as HCl in dioxane or trifluoroacetic acid is used to remove a t-butyl carbamate while piperidine is used to remove 9-fluorenylmethyl carbamate) followed by treatment of the amine with nitric oxide (1–5 atmospheres) in a dry inert solvent such as ether or tetrahydrofuran affords the compound of the formula IVD.

Another embodiment of this aspect provides processes for making compounds having structures V and to the intermediates useful in such processes as follows.

Figure 17:
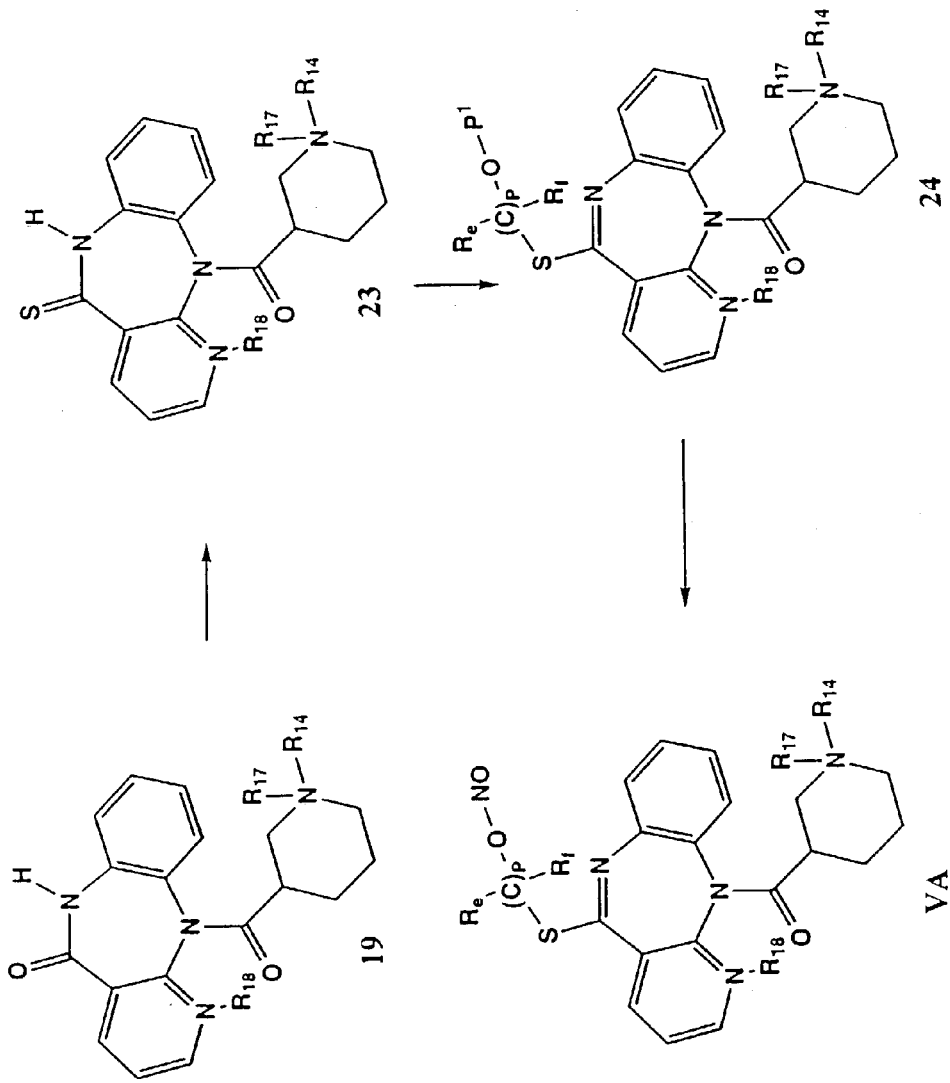
FIG. 17 illustrates a synthetic pathway for the preparation of nitrite containing rispenzepine derivatives.

Nitroso compounds of formula (V) wherein $R_{14}$, $R_{17}$, $R_{18}$, $R_e$, $R_f$, and p are defined as above and an O-nitrosylated isothioamide is representative of the $R_{19}$ group as defined above may be prepared as outlined in FIG. 17. The amide of formula 19 is converted to the thioamide of formula 23 wherein by reaction with a thiation reagent such as 2, 4-bis(4-methoxyphenyl)-2,4-dithioxo-1,2,3,4-dithiadiphosphetane or phosphorus pentasulfide. Alkylation of compound of the formula 23 with an appropriate protected alcohol containing alkylating agent affords a compound of the formula 24 wherein p, $R_e$, $R_f$ and $P^1$ are defined as above. Preferred alkylating agents are alkyl halides or sulfonates while preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VA.

Figure 18:
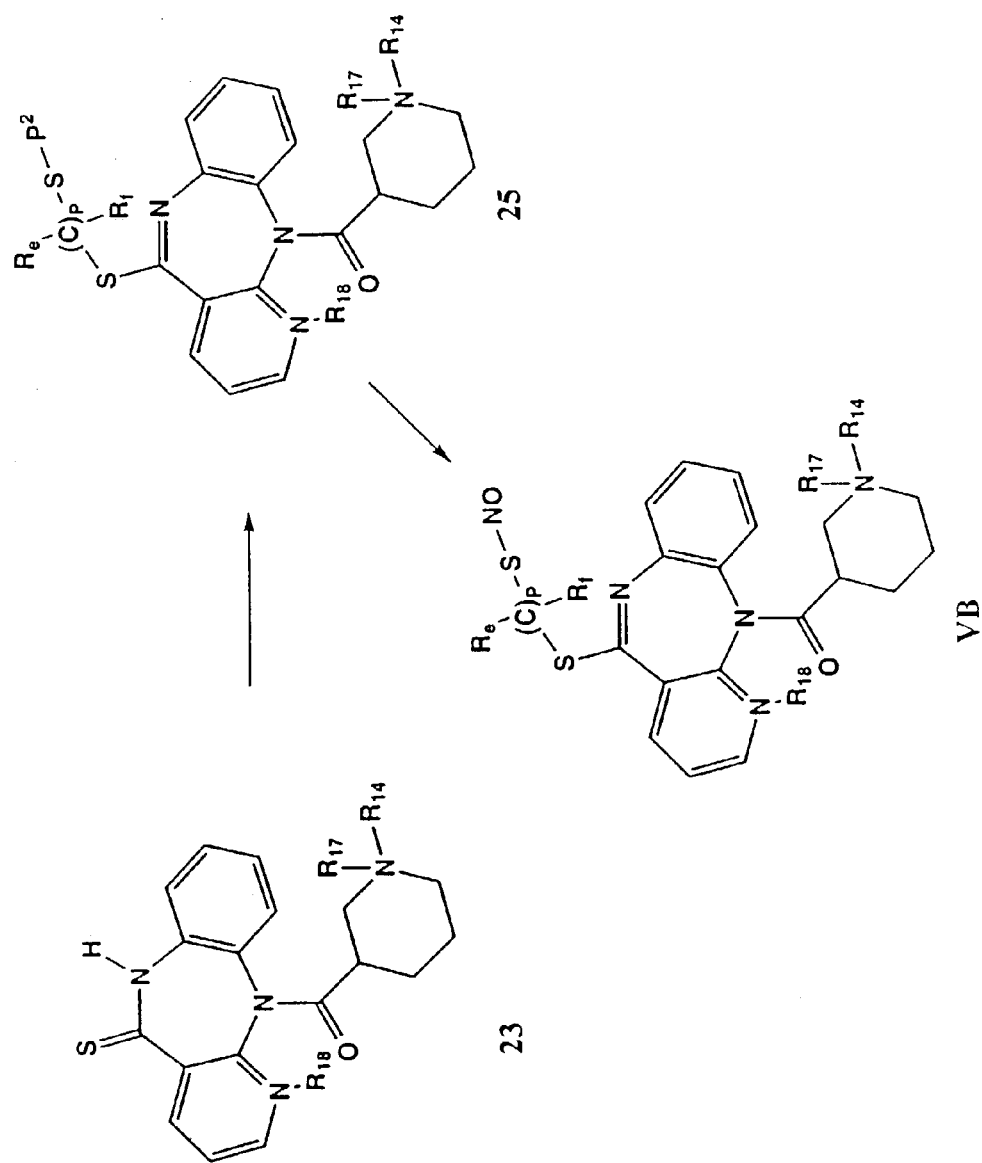
FIG. 18 illustrates a synthetic pathway for the preparation of nitrosothiol containing rispenzepine derivatives.

Nitroso compounds of formula (V) wherein $R_{14}$, $R_{17}$, $R_{18}$, $R_e$, $R_f$, and p are defined as above and an S-nitrosylated isothioamide is representative of the $R_{19}$ group as defined above may be prepared as outlined in FIG. 18. Alkylation of compound of the formula 23 with an appropriate protected thiol containing alkylating agent affords a compound of the formula 25 wherein p, $R_e$, $R_f$, and $P^2$ are defined as above. Preferred alkylating agents are alkyl halides or sulfonates while preferred protecting groups for the thiol moiety are as a thioester such as a thioacetate or thiobenzoate, as a disulfide, or as a thioether such as a 2,4,6-trimethoxybenzyl thioether. Deprotection of the thiol moiety (zinc in dilute aqueous acid, triphenylphosphine in water and sodium borohydride are preferred methods for reducing disulfide groups, mild aqueous or alcoholic base is used to cleave thioesters strong acids such as trifluoroacetic or hydrochloric acid are used to remove a 2,4,6-trimethoxybenzyl thioether group) followed by reaction with a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VB. Alternatively, treatment of compound 25 with a stoichiometric quantity of sodium nitrite in an acidic aqueous or alcoholic solution affords the compound of the formula VB.

Figure 19:
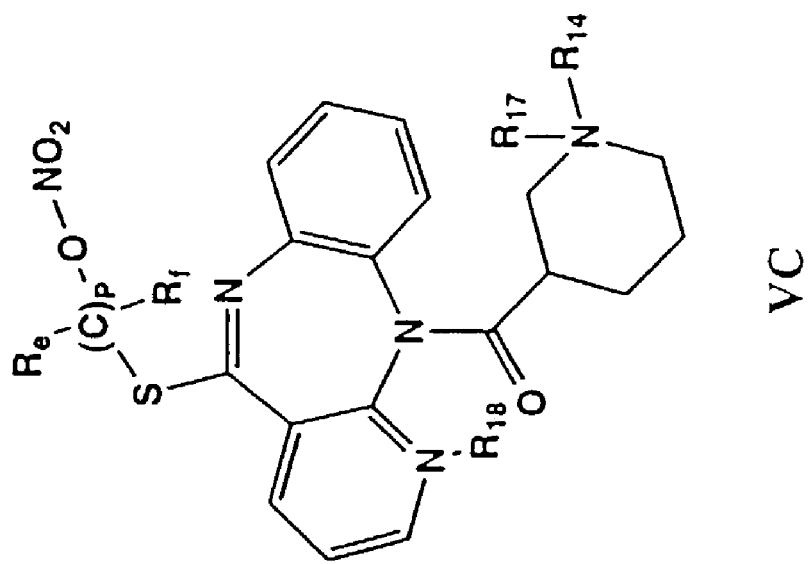
FIG. 19 illustrates a synthetic pathway for the preparation of nitrate containing rispenzepine derivatives.
Figure 19:
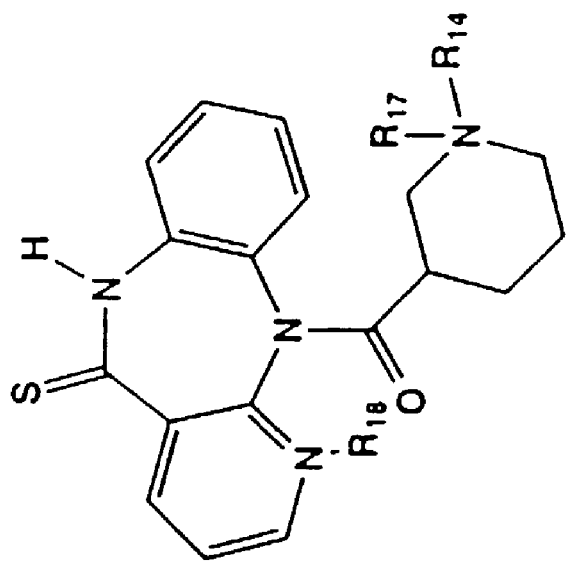

Nitro compounds of formula (V) wherein $R_{14}$, $R_{17}$, $R_{18}$, $R_e$, $R_f$, and p are defined as above and an O-nitrosated isothioamide is representative of the $R_{19}$ group as defined above may be prepared as outlined in FIG. 19. The thioamide of the formula 23 is converted to the compound of the formula VC wherein p, $R_e$ and $R_f$ are defined as above by reaction with an appropriate nitrate containing alkylating agent. Preferred alkylating agents are alkyl halides or sulfonates.

Figure 20:
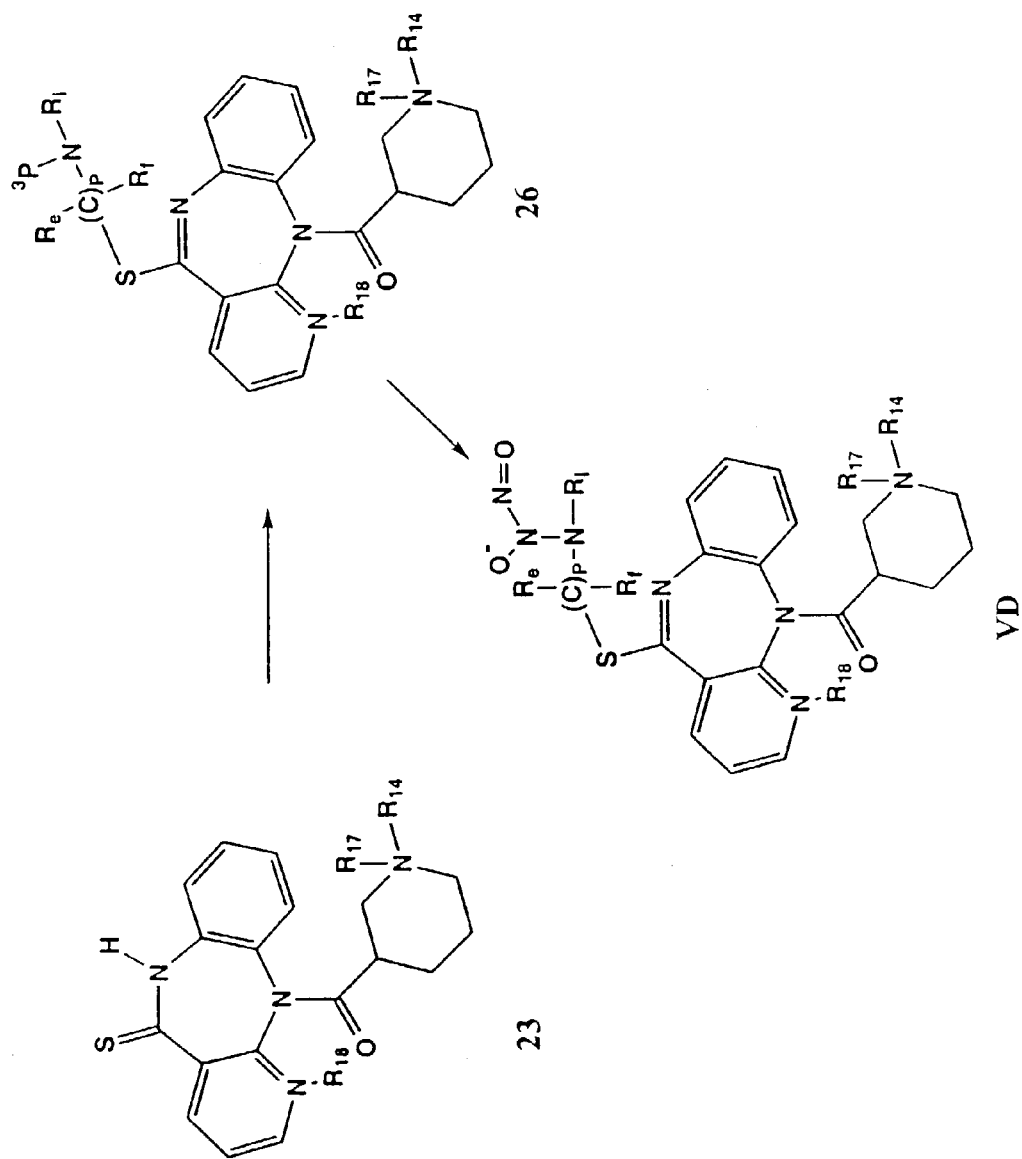
FIG. 20 illustrates a synthetic pathway for the preparation of 2-hydroxy-2-nitrosohydrazine containing rispenzepine derivatives.

2-Hydroxy-2-nitrosohydrazine compounds of formula (V) wherein $R_{14}$, $R_{17}$, $R_{18}$, $R_e$, $R_f$, $R_i$, and p are defined as above and a 2-hydroxy-2-nitrosohydrazine isothioamide is representative of the $R_{19}$ group as defined above may be prepared as outlined in FIG. 20. The thioamide of the formula 23 is converted to the compound of the formula 26 by reaction with an appropriate protected amino containing alkylating agent wherein $P^3$ is as defined above. Preferred alkylating agents are alkyl halides or sulfonates while preferred protecting groups for the amine are as a carbamate such as a t-butyl carbamate or a 9-fluorenylmethyl carbamate. Deprotection of the amino moiety (strong acid such as HCl in dioxane or trifluoroacetic acid is used to remove a t-butyl carbamate while piperidine is used to remove 9-fluorenylmethyl carbamate) followed by treatment of the amine with nitric oxide (1–5 atmospheres) in a dry inert solvent such as ether or tetrahydrofuran affords the compound of the formula VD.

Another embodiment of this aspect provides processes for making compounds having structures VI and to the intermediates useful in such processes as follows.

Figure 21:
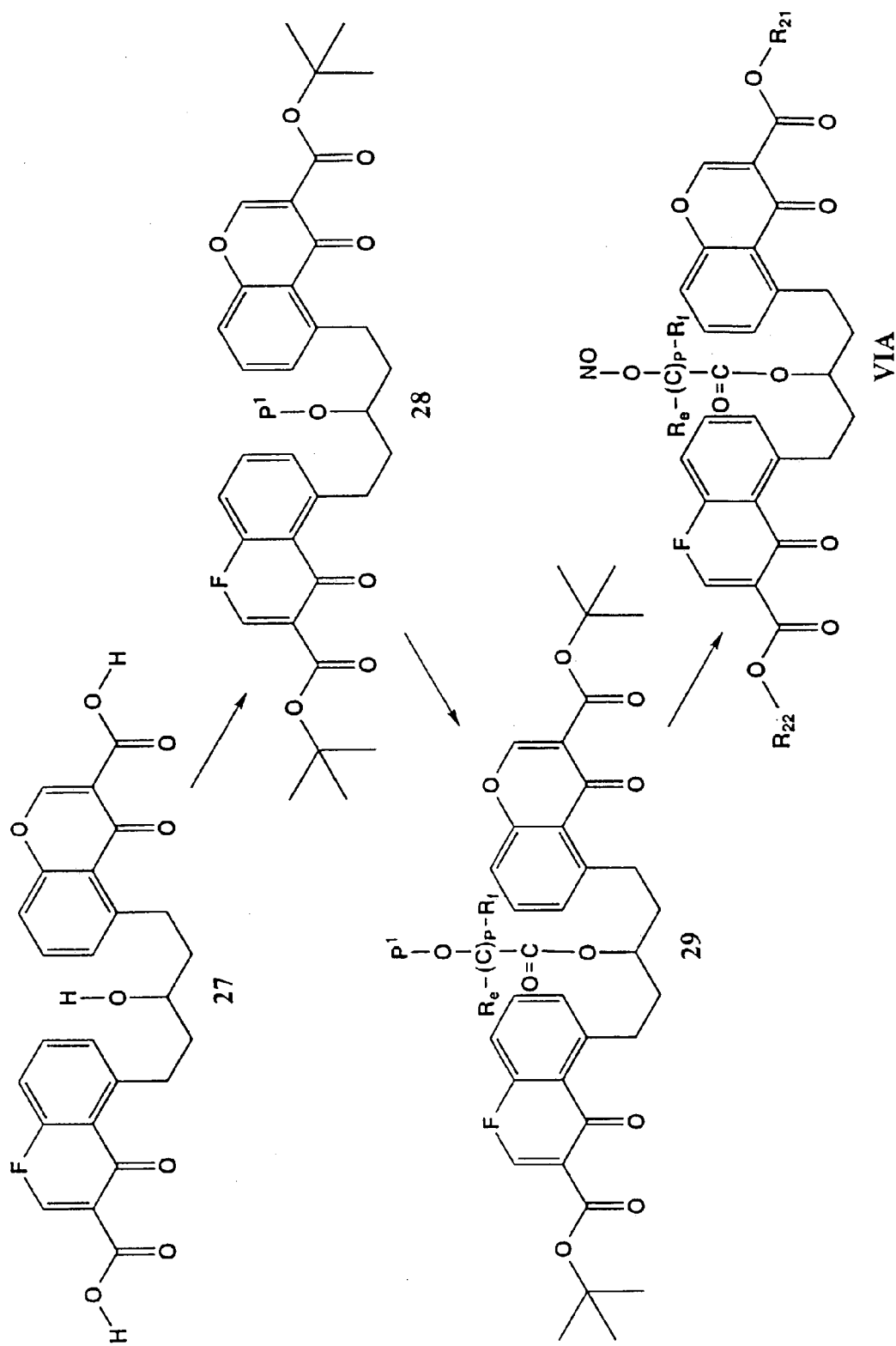
FIG. 21 illustrates a synthetic pathway for the preparation of nitrite containing mast cell stablizer derivatives.

Nitroso compounds of formula (VI) wherein F, $R_{21}$, $R_{22}$, $R_e$, $R_f$, and p are defined as above and an O-nitrosylated ester is representative of the $R_{23}$ group as defined above may be prepared as outlined in FIG. 21. The alcohol and acid groups of formula 27 are protected to afford the compound of the formula 28. Preferred protecting groups for the alcohol are as a carbamate such as a benzyl carbamate or a formate ester such as a benzoylformate ester while preferred protecting groups for the acids are as esters such as t-butyl esters. Deprotection of the hydroxyl moiety (catalytic hydrogenation is the preferred method for cleaving benzyl carbamates while mild aqueous base removes the benzoylformate ester group) followed by reaction of the alcohol group with an appropriate protected alcohol containing activated acylating agent wherein $R_e$, $R_f$, and p and $P^1$ is as defined above affords a compound of the formula 29. Preferred methods for the formation of esters are reacting the alcohol with the preformed acid chloride or symmetrical anhydride of the protected alcohol containing acid or condensing the alcohol and protected alcohol containing acid in the presence of a dehydrating agent such as DCC or EDAC.HCl with or without a catalyst such as DMAP or HOBt. Preferred protecting groups for the alcohol moiety are silyl ethers such as a tert-butyldimethylsilyl ether. Deprotection of the acid and hydroxyl moieties (strong acid such as HCl in dioxane or trifluoroacetic acid cleaves t-butyl esters while fluoride ion is the preferred method for removing silyl ether protecting: groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIA.

Figure 22:
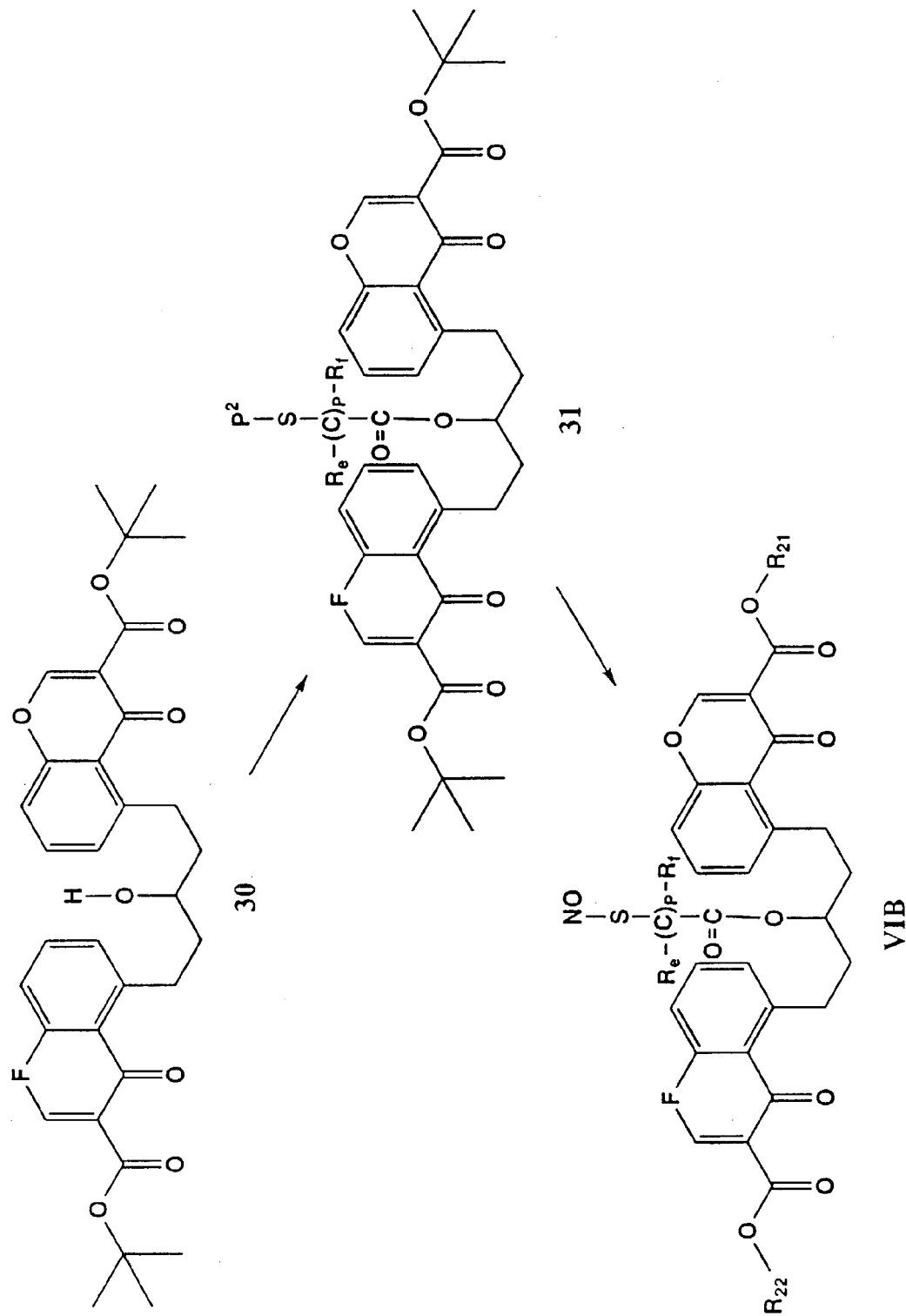
FIG. 22 illustrates a synthetic pathway for the preparation of nitrosothiol containing mast cell stablizer derivatives.

Nitroso compounds of formula (VI) wherein F, $R_{21}$, $R_{22}$, $R_e$, $R_f$, and p are defined as above and an S-nitrosylated ester is representative of the $R_{23}$ group as defined above may be prepared as outlined in FIG. 22. The compound of the formula 30 is converted to the compound of the formula 31 by reaction of the alcohol group with an appropriate protected thiol containing activated acylating agent wherein $R_e$, $R_f$, and p and $P^2$ is as defined above. Preferred methods for the formation of esters are reacting the alcohol with the preformed acid chloride or symmetrical anhydride of the protected thiol containing acid or condensing the alcohol and protected thiol containing acid in the presence of a dehydrating agent such as DCC or EDAC.HCl with or without a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol and acid moieties (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group as well as t-butyl esters) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIB. Alternatively, treatment of the deprotected compound with a stoichiometric quantity of sodium nitrite in an acidic aqueous or alcoholic solution affords the compound of the formula VIB.

Figure 23:
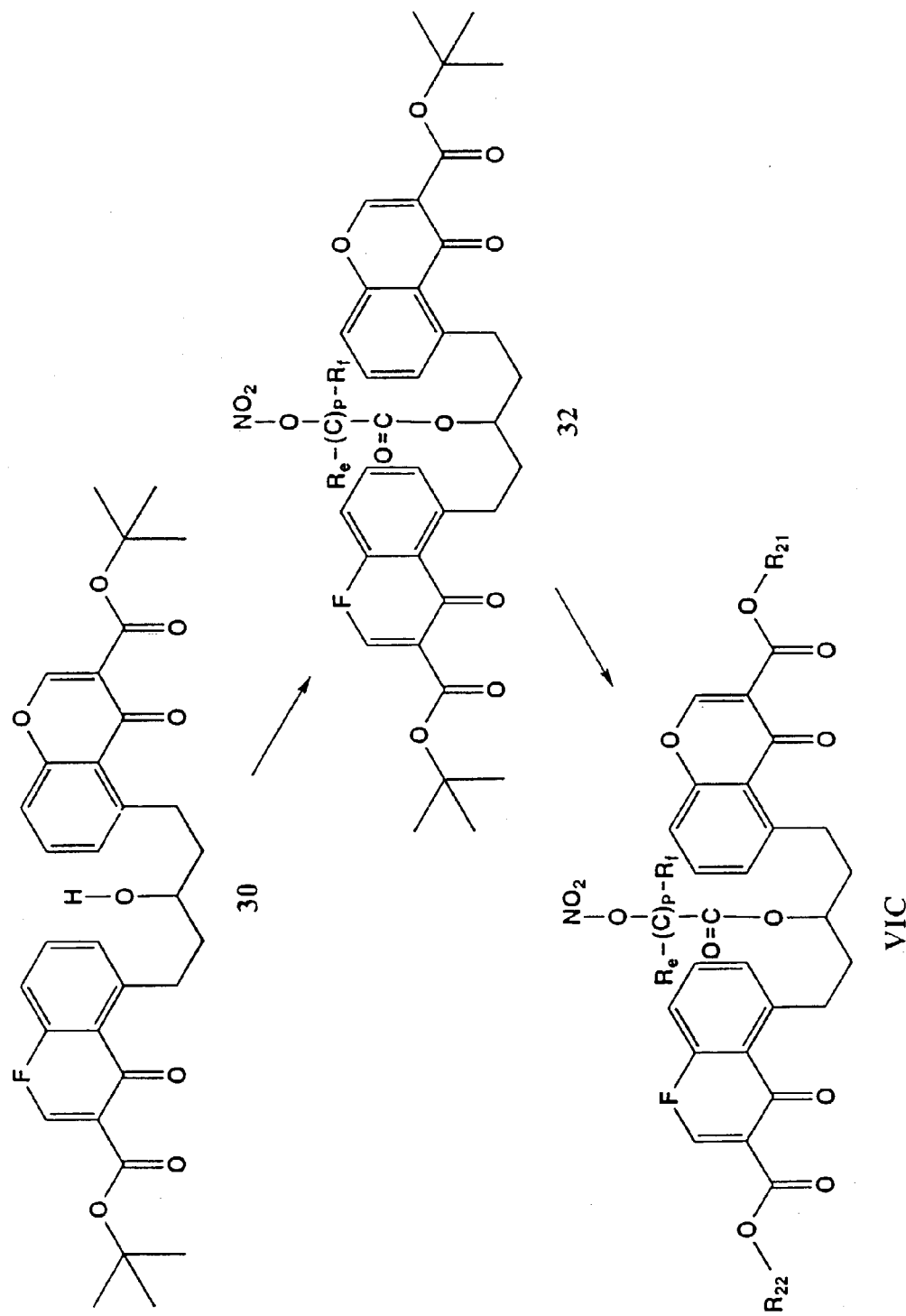
FIG. 23 illustrates a synthetic pathway for the preparation of nitrate containing mast cell stablizer derivatives.

Nitroso compounds of formula (VI) wherein F, $R_{21}$, $R_{22}$, $R_e$, $R_f$, and p are defined as above and an O-nitrosated ester is representative of the $R_{23}$ group as defined above may be prepared as outlined in FIG. 23. The alcohol group of the formula 30 is converted to the ester of the formula 32 wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent such as DCC or EDAC.HCl with or without a catalyst such as DMAP or HOBt. Deprotection of the acid moieties (strong acid such as HCl in dioxane or trifluoroacetic acid cleaves t-butyl esters) affords the compound of the formula VIC.

Figure 24:
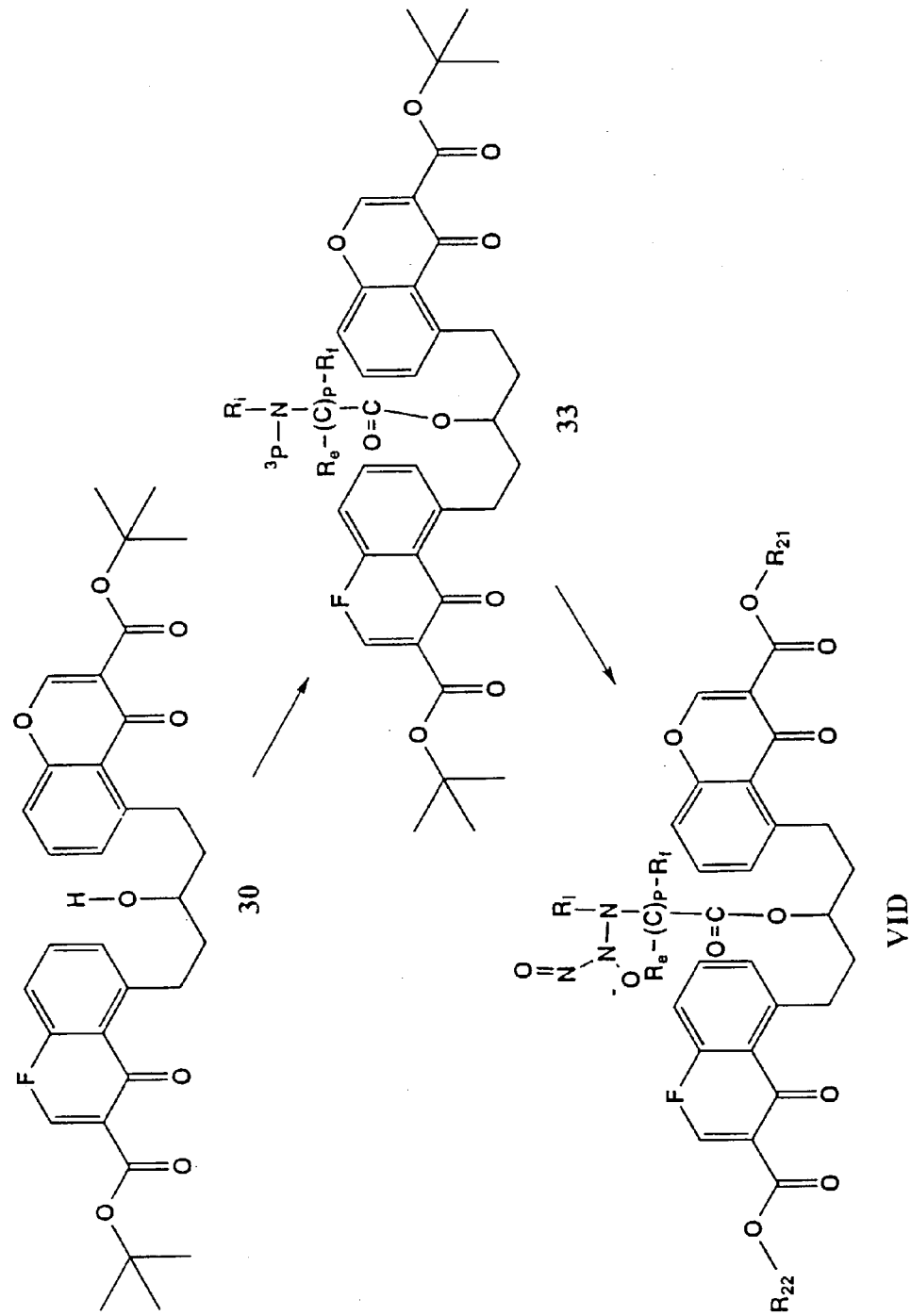
FIG. 24 illustrates a synthetic pathway for the preparation of 2-hydroxy-2-nitrosohydrazine containing mast cell stablizer derivatives.

2-Hydroxy-2-nitrosohydrazine compounds of formula (VI) wherein F, $R_{21}$, $R_{22}$, $R_e$, $R_f$, $R_i$, and p are defined as above and a 2-hydroxy-2-nitrosohydrazine ester is representative of the $R_{23}$ group as defined above may be prepared as outlined in FIG. 24. The alcohol group of the formula 30 is converted to the ester of the formula 33 wherein p, $R_e$ and $R_f$ and $P^3$ are defined as above by reaction with an appropriate protected amine containing activated acylating agent. Preferred methods for the formation of esters are reacting the alcohol with the preformed acid chloride or symmetrical anhydride of the protected amino containing acid or condensing the alcohol and protected amine containing acid in the presence of a dehydrating agent such as DCC or EDAC.HCl with or without a catalyst such as DMAP or HOBt. Preferred protecting groups for the amine are as a carbamate such as a t-butyl carbamate or a 9-fluorenylmethyl carbamate or an amide such ad such as a trifluoroacetamide. Deprotection of the amino and t-butyl ester moieties (strong acid such as HCl in dioxane or trifluoroacetic acid is used to remove a t-butyl carbamate while piperidine is used to remove 9-fluorenylmethyl carbamate while mild aqueous or alcoholic base may be used to cleave a trifluoroacetamide group and strong acid such as HCl in dioxane or trifluoroacetic acid is used to remove a t-butyl ester groups) followed by treatment of the amine with nitric oxide (1–5 atmospheres) in a dry inert solvent such as ether or tetrahydrofuran affords the compound of the formula VID.

Figure 25:
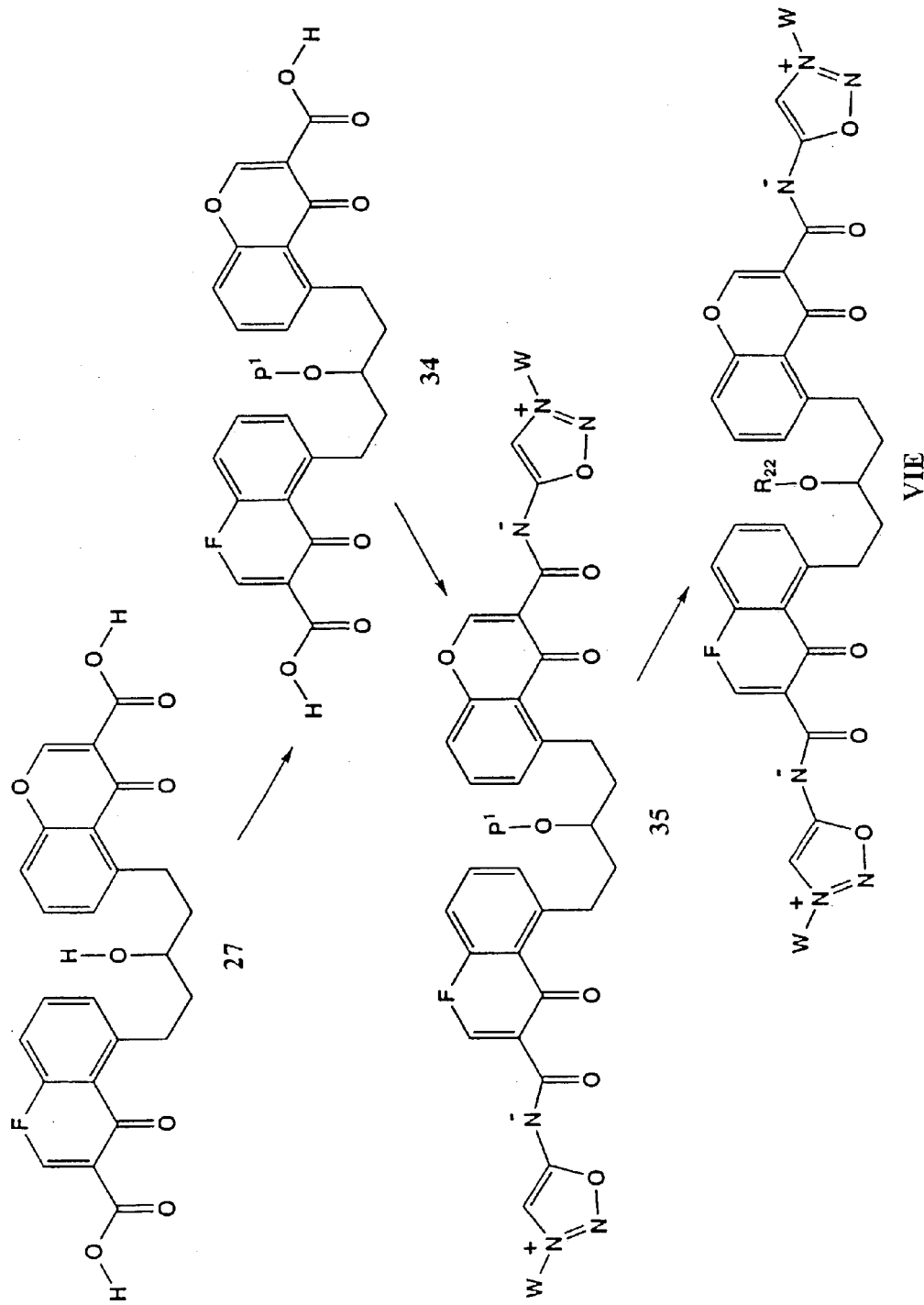
FIG. 25 illustrates a synthetic pathway for the preparation of sidnonimine containing mast cell stablizer derivatives.

Sidnonimine compounds of formula (VI) wherein F, $R_{22}$, $R_e$, $R_f$, and p are defined and a 6-W-substituted sydnonimine wherein W is as defined above is representative of the $R_{20}$ and $R_{21}$ groups as defined above may be prepared as outlined in FIG. 25. The alcohol of formula 27 is protected to afford the compound of the formula 34. Preferred protecting groups for the alcohol are as a carbamate such as a t-butyl carbonate or a silyl ether such as a trimethylsilyl ether. The diacid of the formula 34 is converted into the dicarboximide of the formula 35 by reaction with a 6-W-substituted sydnonimine. Preferred methods for the preparation of carboximides are initially forming the dimixed anhydride via reaction of 34 with a chloroformate such as isobutylchloroformate in the presence of a non nucleophilic base such as triethylamine in an anhydrous inert solvent such as diethylether or THF. The dimixed anhydride is then reacted with the 6-W-substituted sydnonimine to afford 35. Alternatively, the diacid 34 and may be coupled to the 6-W-substituted sydnonimine afford 35 by treatment with a dehydration agent such as DCC or EDAC with or without a catalyst such as DMAP or HOBt. Alternatively, the diacid 34 may be converted into an active ester by reaction with a suitably substituted phenol utilizing any of the conditions for ester formation described, followed by reaction with the a 6-W-substituted sydnonimine. Preferred 6-W-substituted sydnonimines are 1,2,6,4-oxatriazolium, 6-amino-6-morpholine and are 1,2,6,4-oxatriazolium, 6-amino-6-(6-chloro-2-methyl-benzene) and preferred active esters are para-nitrophenyl, 2,4,6-trichlorophenyl, and pentafluorophenyl. Deprotection of the hydroxyl moiety (strong acid such as HCl or trifluoroacetic acid is used to cleave t-butyl carbonates while fluoride is the preferrred method for removing silyl ethers) in the compound of the formula 35 affords the compound of the formula VIE.

Another embodiment of this aspect provides processes for making compounds having structures VII and to the intermediates useful in such processes as follows.

Figure 26:
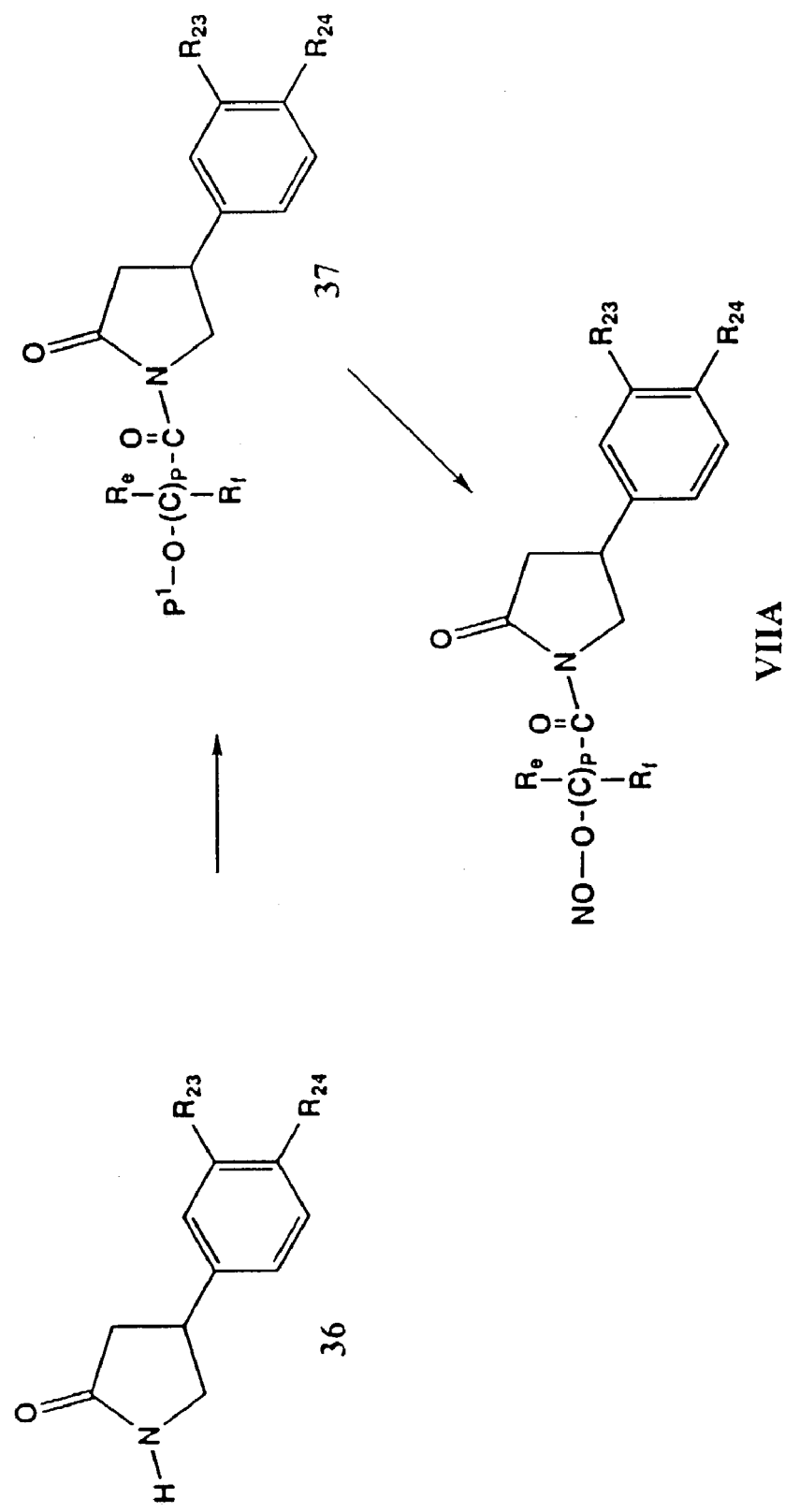
FIG. 26 illustrates a synthetic pathway for the preparation of nitrite containing phosphodiesterase inhibitor derivatives.

Nitroso compounds of formula (VII) wherein $R_{23}$, $R_{24}$, $R_e$, $R_f$, and p are defined as above and an O-nitrosylated imide is representative of the $R_{25}$ group as defined above may be prepared as outlined in FIG. 26. The amide nitrogen of formula 36 is converted to the imide of formula 37 wherein p, $R_e$ and $R_f$ are defined as above by reaction with an appropriate protected alcohol containing activated acylating agent wherein $P^1$ is as defined above. Preferred methods for the formation of imides are reacting the alcohol with the preformed acid chloride or symmetrical anhydride of the protected alcohol containing acid or condensing the alcohol and protected alcohol containing acid in the presence of a dehydrating agent such as DCC or EDAC.HCl with a catalyst such as DMAP. Preferred protecting groups for the alcohol moiety are silyl ethers such as a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of the formula VIIA.

Figure 27:
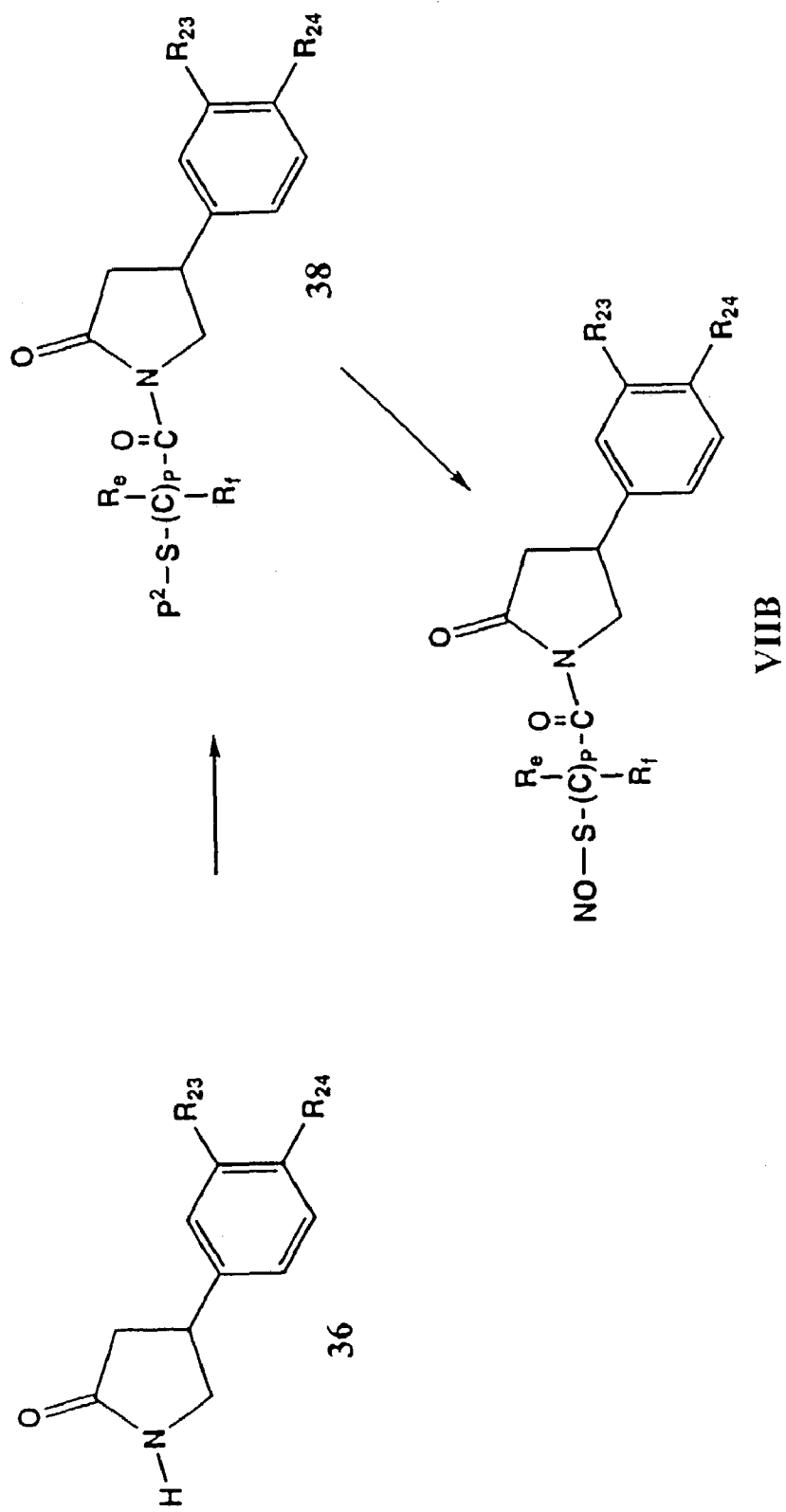
FIG. 27 illustrates a synthetic pathway for the preparation of nitrosothiol containing phosphodiesterase inhibitor derivatives.

Nitroso compounds of formula (VII) wherein $R_{23}$, $R_{24}$, $R_e$, $R_f$, and p are defined as above and an S-nitrosylated imide is representative of the $R_{25}$ group as defined above may be prepared as outlined in FIG. 27. The amide nitrogen of formula 36 is converted to the imide of formula 38 wherein p, $R_e$ and $R_f$ are defined as above by reaction with an appropriate protected thiol containing activated acylating agent wherein $P^2$ is as defined above. Preferred methods for the formation of imides are reacting the amide with the preformed acid chloride or symmetrical anhydride of the protected thiol containing acid or condensing the amide and protected thiol containing acid in the presence of a dehydrating agent such as DCC or EDAC.HCl with a catalyst such as DMAP. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of the formula VIIB. Alternatively, treatment of compound 38 with a stoichiometric quantity of sodium nitrite in an acidic aqueous or alcoholic solution affords the compound of the formula VIIB.

Figure 28:
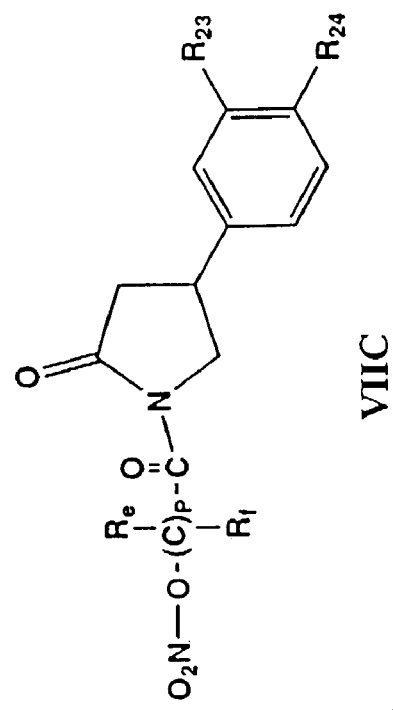
FIG. 28 illustrates a synthetic pathway for the preparation of nitrate containing phosphodiesterase inhibitor derivatives.
Figure 28:
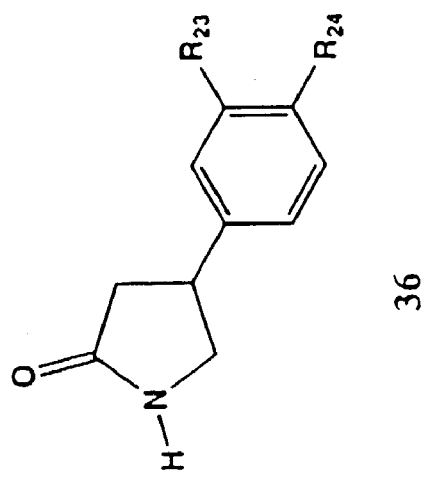

Nitro compounds of formula (VII) wherein $R_{23}$, $R_{24}$, $R_e$, $R_f$, and p are defined as above and an O-nitrosated imide is representative of the $R_{25}$ group as defined above may be prepared as outlined in FIG. 28. The amide of the formula 36 is converted to the imide of the formula VIIC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent such as DCC or EDAC. HCl with a catalyst such as DMAP.

Figure 29:
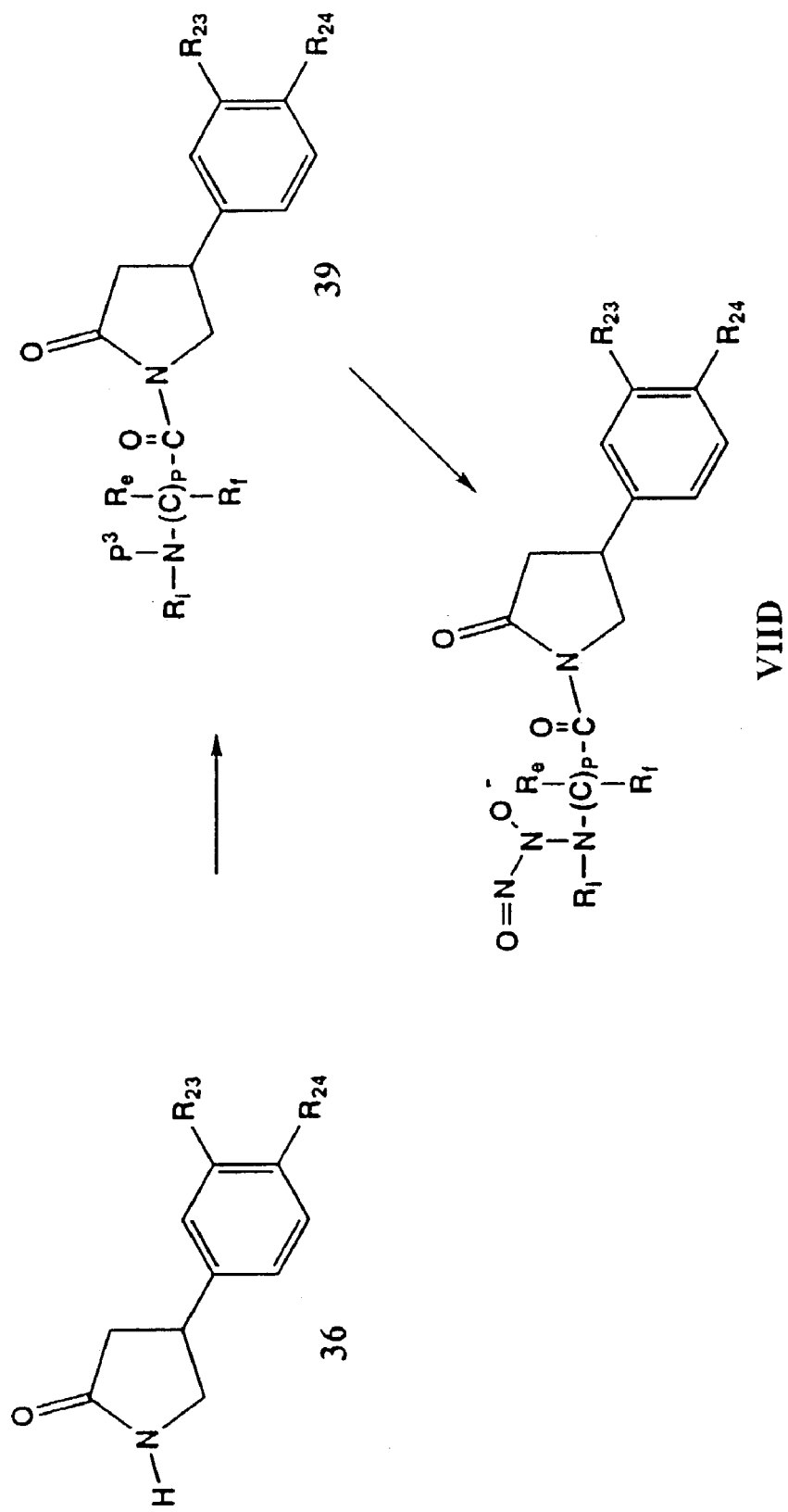
FIG. 29 illustrates a synthetic pathway for the preparation of 2-hydroxy-2-nitrosohydrazine containing phosphodiesterase inhibitor derivatives.

2-Hydroxy-2-nitrosohydrazine compounds of formula (VII) wherein $R_{23}$, $R_{24}$, $R_e$, $R_f$, $R_i$, and p are defined as above and a 2-hydroxy-2-nitrosohydrazine imide is representative of the $R_{25}$ group as defined above may be prepared as outlined in FIG. 29. The amide of the formula 36 is converted to the imide of the formula 39 wherein p, $R_e$, $R_f$, and $R_i$ are defined as above by reaction with an appropriate protected amino containing activated acylating agent wherein $P^3$ is as defined above. Preferred methods for the formation of imides are reacting the amide with the preformed acid chloride or symmetrical anhydride of the protected amino containing acid or condensing the alcohol and protected amine containing acid in the presence of a dehydrating agent such as DCC or EDAC:HCl with a catalyst such as DMAP. Preferred protecting groups for the amine are as a carbamate such as a t-butyl carbamate or a 9-fluorenylmethyl carbamate. Deprotection of the amino moiety (strong acid such as HCl in dioxane or trifluoroacetic acid is used to remove a t-butyl carbamate while piperidine is used to remove 9-fluorenylmethyl carbamate) followed by treatment of the amine with nitric oxide (1–5 atmospheres) in a dry inert solvent such as ether or tetrahydrofuran affords the compound of the formula VIID.

As noted above, another aspect the invention provides a composition comprising (i) a therapeutically effective amount of a steroid, a β-agonist, an anticholinergic, a mast cell stabilizer or a PDE inhibitor, which optionally can be substituted with at least one NO or $NO_2$ group or a group that stimulates endogenous production of NO or EDRF in vivo, and (ii) a compound that donates, transfers or releases nitric oxide as a charged species, i.e., nitrosonium ($NO^+$) or nitroxyl ($NO^-$), or as the neutral species, nitric oxide (NO.) and/or a compound that stimulates endogenous production of NO or EDRF in vivo.

The compounds that donate, transfer or release nitric oxide can be any of those known to the art, including those mentioned and/or exemplified below.

Nitrogen monoxide can exist in three forms: $NO^-$ (nitroxyl), NO. (nitric oxide) and $NO^+$ (nitrosonium). NO. is a highly reactive short-lived species that is potentially toxic to cells. This is critical, because the pharmacological efficacy of NO depends upon the form in which it is delivered. In contrast to NO., nitrosonium and nitroxyl do not react with $O_2^-$ species, and are also resistant to decomposition in the presence of redox metals. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO.) and charged nitric oxide species, particularly including nitrosonium ion (NO⁺) and nitroxyl ion (NO⁻). The reactive form of nitric oxide can be provided by gaseous nitric oxide. The nitric oxide releasing, delivering or transferring compounds, having the structure K—NO wherein K is a nitric oxide releasing, delivering or transferring moiety, include any and all such compounds which provide nitric oxide to its intended site of action in a form active for their intended purpose. As used here, the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-((E)-hydroxyimino)-5-nitro-3-hexene arines or amides, nitrosoamines, furoxans, as well a subtstates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated-modified and unmodified oligonucleotides (preferably of at least 5, and more particularly 5–200, nucleotides); and an S-nitrosylated hydrocarbons where the hydrocarbon can be a branched or unbranched, and saturated or unsaturated aliphatic hydrocarbon, or an aromatic hydrocarbon; S-nitrosylated hydrocarbons having one or more substituent groups in addition to the S-nitroso group; and heterocyclic compounds. S-nitrosothiols and the methods for preparing them are described in U.S. Pat. No. 5,380,758; Oae et al., *Org. Prep. Proc. Int.*, 15(3):165–198 (1983); Loscalzo et al., *J. Pharmacol. Exp. Ther.*, 249(3):726729 (1989) and Kowaluk et al., *J. Pharmacol. Exp. Ther.*, 256:1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof) from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

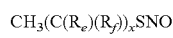        (i)

wherein x equals 2 to 20 and R_e and R_f are as defined above;

        (ii)

wherein x equals 2 to 20; and R_e and R_f are as defined above;

        (iii)

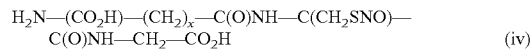        (iv)

wherein x equals 2 to 20; R_e and R_f are as defined above; and B is selected from the group consisting of fluoro, $C_1$–$C_6$ alkoxy, cyano, carboxamido, cycloalkyl, arylalkoxy, alkylsulfinyl, arylthio, alkylamino, dialkylamino, hydroxy, carbamoyl, N-alkylcarbamoyl, N,N-dialkylcarbamoyl, amino, hydroxyl, carboxyl, hydrogen, nitro and aryl.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric, acetic and hydrochloric acids. Alternatively, the precursor thiol may be nitrosylated by treatment with an alkyl nitrite such as tert-butyl nitrite.

Another group of such NO adducts are those wherein the compounds donate, transfer or release nitric oxide and are selected from the group consisting of compounds that include at least one ON—N— or ON—C— group. The compound that includes at least one ON—N— or ON—C— group is preferably selected from the group consisting of ON—N— or ON—C-polypeptides (the term "polypeptide" includes proteins and also polyamino acids that do not possess an ascertained biological function, and derivatives thereof); ON—N— or ON—C-amino acids (including natural and synthetic amino acids and their stereoisomers and racemic mixtures); ON—N— or ON—C-sugars; ON—N— or ON—C-modified and unmodified oligonucleotides (preferably of at least 5, and more particularly 5–200, nucleotides), ON—O—, ON—N— or ON—C-hydrocarbons which can be branched or unbranched, saturated or unsaturated aliphatic hydrocarbons or aromatic hydrocarbons; ON—N— or ON—C-hydrocarbons having one or more substituent groups in addition to the ON—N— or ON—C-group; and ON—N— or ON—C-heterocyclic compounds.

Another group of such NO adducts is the nitrites which have an —O—NO group wherein the organic template to which the nitrite group is appended is a protein, polypeptide, amino acid, carbohydrate, branched or unbranched and saturated or unsaturated alkyl, aryl or a heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and are selected from the group consisting of compounds that include at least one at least one $O_2N$—O—, $O_2N$—N—, $O_2N$—S— or $O_2N$—C— group. Preferred among these are those selected from the group consisting of $O_2N$—O—, $O_2N$—N—, $O_2N$—S— or $O_2N$—C-polypeptides; $O_2N$—O—, $O_2N$—N—, $O_2N$—S— or $O_2N$—C-amino acids; $O_2N$—O—, $O_2N$—N—, $O_2N$—S— or $O_2N$—C-modified and unmodified oligonucleotides; $O_2N$—O—, $O_2N$—N—, $O_2N$—S— or $O_2N$—C-hydrocarbons which can be branched or unbranched, saturated or unsaturated aliphatic hydrocarbons or aromatic hydrocarbons; $O_2N—O—$, $O_2N—N—$, $O_2N—S—$ or $O_2N—C$-hydrocarbons having one or more substituent groups in addition to the $O_2N—O—$, $O_2N—N—$, $O_2N—S—$ or $O_2N—C$-group; and $O_2N—O—$, $O_2N—N—$, $O_2N—S—$ or $O_2N—C$-heterocyclic compounds. Preferred examples are isosorbide dinitrate and isosorbide mononitrate.

Another group of such NO adducts is the nitroso-metal compounds which have the structure $(L)_u$-M-$(NO)_v$-$A_z$. M is a metal, preferably a transition metal; L includes any appropriate organic or inorganic ligand directly attached to the metal; u, v, z are each integers independently selected from 1 to 5; and A is an appropriate organic or inorganic counterion to yield a neutral species. Preferred metals include iron, copper, manganese, cobalt, selenium and luthidium. A preferred example is sodium nitroprusside.

Another group of such adducts are 2-hydroxy-2-nitrosohydrazines which donate, transfer or release nitric oxide and have a $R_{61}R_{62}N—N(O—M^+)—NO$ group wherein $R_{61}$ and $R_{62}$ include polypeptides, amino acids, sugars, modified and unmodified oligonucleotides, hydrocarbons where the hydrocarbon can be a branched or unbranched, and saturated or unsaturated aliphatic hydrocarbon or an aromatic hydrocarbon, hydrocarbons having one or more substituent groups and heterocyclic compounds. $M^+$ is a metal cation, such as, for example, a Group I metal cation.

Another group of such adducts are thionitrates which donate, transfer or release nitric oxide and have the structure $R_{61}—S—NO_2$ wherein $R_{61}$ is as described above.

Compounds that stimulate endogenous synthesis of NO or EDRF in vivo include L-arginine, the substrate for nitric oxide synthase, cytokines, adenosine, bradykinin, calreticulin, bisacodyl, phenolphthalein, and endothelein.

The compounds and compositions of the invention are useful in the treatment of a large number of disorders, particularly those related to or characterized by pulmonary dysfunction. Examples of such indications include preventing (if given prior to the onset of symptoms) or reversing the following: acute pulmonary vasoconstriction, such as may result from pneumonia, traumatic injury, aspiration of inhalation injury, fat embolism in the lung, acidosis, inflammation of the lung, adult respiratory distress syndrome, acute pulmonary edema, acute mountain sickness, asthma, post cardiac surgery acute pulmonary hypertension, persistent pulmonary hypertension of the newborn, perinatal aspiration syndrome, hyaline membrane disease, acute pulmonary thromboembolism, heparin-protamine reactions, sepsis, asthma, status asthmaticus, or hypoxia (including that which may occur during one-lung anesthesia), as well as those cases of chronic pulmonary vasoconstriction which have a reversible component, such as may result from chronic pulmonary hypertension, bronchopulmonary dysplasia, chronic pulmonary thromboembolism, idiopathic or primary pulmonary hypertension, or chronic hypoxia.

When administered in vivo, the nitric oxide adduct may be administered in combination with pharmaceutical carriers and in dosages described herein.

The instant disclosure, particularly in combination with the significant body of literature, commercially available pharmaceutically acceptable liquid, solid and gaseous carriers and vehicles, volume expanders, tabletting and encapsulation materials, enteric and other coatings, and inhalant and intranasal delivery devices and the ordinary skill of those practicing in the field, amply teaches the reader how to use the compounds and compositions of the invention in the methods of the invention and particularly for oral and nasal inhalation and intranasal therapy. The following is supplementary to and exemplary thereof.

The pharmaceutical compositions utilized in this invention can be administered preferably by inhalation (oral and/or nasal), and also by intranasal mucosal administration, oral, enteral, topical, vaginal, sublingual, rectal, intramuscular, intravenous, or subcutaneous means.

The compounds of this invention can be employed in combination with conventional excipients; i.e., pharmaceutically acceptable organic or inorganic carrier substances suitable for parenteral, enteral or intranasal application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

Many therapeutically active ingredients have been administered or applied to the body by means of inhalation, such as in aerosol dosage form. One of the main reasons for the rapid and widespread acceptance of the inhalation dosage forms for the administration of therapeutically active agents is that it affords many and dinstinct advantages to the user. These advantages have been described by various investigators and, for aerosol and metered-dose inhalers, include rapid onset of action; circumvention of the first-pass effect; avoidance of degradation in the gastrointestinal tract; lower dosage which will minimize adverse reactions; dose titration to individual needs and ideal for as-needed medication. It is an ideal alternate route when the chosen therapeutic agent may interact chemically or physically with other medicinals needed concurrently, or when the drug entity exhibits erratic pharmacokinetics upon oral or parenteral administration.

The term "aerosol" is used to denote various systems ranging from those of a colloidal nature to systems consisting of "pressurized packages." The present definition refers to those products which depend upon the power of a liquefied or compressed gas to dispense the active ingredient(s) in a finely dispersed mist, foam or semisolid. Pump systems which also dispense the active ingredient(s) in the form of a finaly dispersed mist (although of greater particle size) often are classified as aerosols.

The pressure package is convenient and easy to use. Medication is dispensed in a ready-to-use form at the push of a buttom. Since the medication is sealed in a tamper-proof pressure container, there is no danger of contamination and the contents can be protected from air and moisture. Easily decomposed drugs especially lend themselves to this type of administration. For those products requiring regulation of dosage, a metering valve can be used. An accurately measured dose of therapeutically active drug can be administered quickly and in the proper particle-size range. In addition, when used with expensive products, such as some steroids, savings can be achieved by the user as compared to the use of other preparations such as ointments, creams or lotions. The aerosol dosage form allows for the dispensing of the product in the most desirable form; spray, foam or semisolid. Depending on the nature of the product, the characteristics of the spray or foam can be changed to insure the proper and most efficient use of the medication.

For parenteral application, particularly suitable vehicles consist of solutions, preferably oily or aqueous solutions, as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or com starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

The nitrosated or nitrosylated compounds of the invention are used at dose ranges and over a course of dose regimen and are administered in the same or substantially equivalent vehicles/carrier by the same or substantially equivalent oral or nasal inhalant devices as their non-nitrosated or non-nitrosylated counterparts. The nitrosated or nitrosylated compounds of the invention can also be used in lower doses and in less extensive regimens of treatment. The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

While the compounds of the invention can be administered as the sole active pharmaceutical agent, they can also be used in combination with one or more compounds which are known to be effective against the specific disease state targeted for treatment. The compositions of the invention can also be administered as described above or can be made to include one or more additional active compounds which are known to be effective against the specific disease state is targeted for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

These and other aspects of the present invention will be apparent to those skilled in the art from the teachings herein.

EXAMPLES

Example 1

6α-Fluoro-11β-hydroxy-16α,17-((1-methylethylidene)bis(oxy))pregna-1,4-diene-3,20-dione-21-(3-methyl-3-nitrosothio)-butanoate 1a. 3-Methyl-3(2,4,6-trimethoxyphenylmethylthio)butyric Acid To a solution of 3-mercapto-3-methylbutyric acid (B. J. Sweetman et al. *J. Med Chem.*, 14, 868 (1971)) (4.6 g, 34 mmol) in methylene chloride (250 mL) under nitrogen and cooled over ice/salt to 5° C. (internal temperature) was added trifluoroacetic acid (82 g, 0.72 mol). No significant temperature rise was noted during the addition. To this was then added dropwise a solution of 2,4,6-trimethoxybenzyl alcohol (M. C. Munson et al., *J. Org. Chem.*, 57, 3013 (1992)) (6.45 g, 32 mmol) in methylene chloride (150 mL) such that the reaction temperature does not rise above 5° C. After the addition was complete, the mixture was stirred for an additional 5 minutes at 5° C. and the volatiles were removed in vacuo (toluene or ethyl acetate can be used to assist in the removal of volatile material). The residue was partitioned between diethyl ether and water and the organic phase dried over anhydrous sodium sulfate, filtered and the volatile material removed in vacuo. The residue was treated with activated charcoal and recrystalised from diethyl ether/hexane. The product was isolated as an white solid in 70% yield (7 g) mp 103–105° C. $^1$H NMR (CDCl$_3$) δ 6.12 (s, 2H), 3.80–3.85 (m, 11H), 2.74 (s,2H), 1.47 (s, 6H). $^{13}$C NMR (CDCl$_3$) δ173.9, 160.6, 158.6, 105.6, 90.5, 55.7, 55.3, 45.9, 43.6, 28.4, 21.0.

1b. 6α-Fluoro-11β-hydroxy-16α,17-((1-methylethylidene)bis(oxy))pregna-1,4-dien-3,20-dione-21-(3-methyl-3-(2,4,6-trimethoxyphenyl methylthio))-butanoate A solution 6α-Fluoro-11β, 21-dihydroxy-16α,17-((1-methylethylidene)bis(oxy))pregna-1,4-diene—3,20-dione (357 mg, 0.8 mmol), the compound of Example 1a (251 mg, 0.8 mmol) and 4-dimethylaminopyridine (20 mg, 0.16 mmol) in anhydrous DMF (5 mL) was treated with 1-ethyl-3-(3-dimethylaminopropyl)carbodiimide (157 mg, 0.8 mmol). The resultant solution was stirred at room temperature for 2 hours when the solvent was removed in vacuo and the residue poured into water and extracted with ethyl acetate. The organic phase was dried over anhydrous sodium sulfate, filtered and the solvent removed in vacuo. The residue was chromatographed on silica gel using ethyl acetate:hexane (1:1) The product was isolated as a solid in 41% yield (240 mg), mp 195–197° C. $^1$H NMR (CDCl$_3$) δ 7.22 (d, J=10 Hz, 1H), 6.36 (s, 1H), 6.34 (d, J=10 Hz, 1H), 6.14 (s, 2H), 5.35 (ddd, J=50 Hz, 11 Hz, 6 Hz), 4.95–5.05 (m, 1H), 4.97 (d, J=18 Hz, 1H), 4.82 (d, J=18 Hz, 1H), 2H), 4.47–4.55 (m, 1H), 3.81–3.89 (m, 11H), 2.86 (s, 2H), 2.46–2.54 (m, 1H), 2.17–2.30 (m,1H), 2.03–2.09 (m, 1H), 1.60–1.88 (m, 5H), 1.56 (s, 3H), 1.54 (s, 3H), 1.45 (s, 6H), 1.1–1.5 (m, 5H), 1.24 (s, 3H), 0.96 (s, 3H). $^{13}$C NMR (CDCl$_3$) δ 205.03, 186.82, 171.77, 166.52, 166.34, 161.65, 160.03, 155.93, 129.67, 119.89, 119.72, 112.72, 108.78, 98.85, 92.03, 89.87, 83.05, 71.02, 68.77, 57.12, 56.74, 56.11, 51.03, 47.80, 47.26, 45.25, 45.02, 41.94, 41.31, 35.25, 30.01, 29.86, 29.46, 29.35, 27.95, 27.05, 22.69, 22.21, 18.17. Anal ysis for $C_{39}H_{51}FO_{10}S$: 0.5$H_2O$: Calculated: C: 63.32; H: 7.03. Found: C: 63.39; H: 7.00.

1c. 6α-Fluoro-11β-hydroxy-16α,17-((1-methylethylidene)bis(oxy))pregna-1,4-dien-3,20-dione-21-(3-methyl-3-mercapto)-butanoate A stirred solution of the compound of Example 1b (220 mg, 27 μmol), anisole (200 μL, 1.8 mmol), phenol (200 mg, 2.1 mmol) and water (200 μL, 11 mmol) in methylene chloride (0.2 mL) was treated with trifluoroacetic acid (1.5 mL). The resultant solution was stirred at room temperature for 1 hour. Toluene was added and the volatile material removed in vacuo. The residue was chromatographed on silica gel using ethyl acetate:hexane (1:3 then 1:1). The product was obtained as a solid in 42% yield (70 mg) mp 205–208° C. $^1$H NMR (CDCl$_3$) δ 7.22 (d, J=9.8 Hz, 1H), 6.36 (s, 1H) 6.34 (d, J=10 Hz, 1H), 5.35 (ddd, J=50 Hz, 11 Hz, 6 Hz), 5.01 (d, J=4.2 Hz, 1H), 4.95 (d, J=6.2 Hz, 1H), 4.03–4.07 (m, 1H). 2.80 (d, J=3 Hz, 2H), 2.46–2.54 (m, 1H), 2.43 (s, 1H), 2.17–2.30 (m, 1H), 2.07–2.13 (m, 1H), 1.6–1.89 (m, 7H), 1.57 (s, 6H), 1.45 (s, 6H), 1.3–1.4 (m, 2H), 1.24 (s, 3H), 1.16 (dd, J=11 Hz, 3.3 Hz, 1H), 0.96 (s, 3H).

1d. 6α-Fluoro-11β-hydroxy-16α,17-((1-methylethylidene)bis(oxy))pregna-1,4-dien-3,20-dione-21-(3-methyl-3-nitrosothio)-butanoate A solution of the compound of Example 1c (60 mg, 0.11 mmol) in methylene chloride (1 mL) was treated with tert butyl nitrite (25 μL, 22.5 mg, 0.22 mmol) and the resultant solution stirred for 1 hr at room temperature. An additional 12 μL of tert butyl nitrite was added and the solution stirred for an additional 15 min at room temperature. The volatile material was evaporated in vacuo and the residue chromatographed on silica gel using methanol:methylene chloride (1:25). The product was isolated as a green solid 40 mg (65%). $^1$H NMR (CDCl$_3$) δ 7.12 (d, J=10 Hz, 1H), 6.26 (s, 1H), 6.25 (d, J=10 Hz, 1H), 5.30 (ddd, J=50 Hz, 10 Hz, 6 Hz)4.91–4.94 (m, 1H), 4.88 (d, J=18 Hz, 1H), 4.78 (d, J=18 Hz, 1H), 4.41–4.47 (m, 1H), 3.33 (s, 2H), 2.38–2.47 (m, 1H), 2.10–2.20 (m, 1H), 1.99 (s, 3H), 1.97 (s, 3H), 1.36 (s, 6H), 1.04–1.75 (m, 8H), 1.15 (s, 3H), 0.86 (s, 3H).

Example 2

(8r)-3α-hydroxy-8-isopropyl-1αH,5αH-tropanium nitrite (±)-tropate (8r)-3α-hydroxy-8-isopropyl-1αH,5αH-tropanium bromide (±)-tropate (0.2 g, 0.48 mmol) was dissolved in hot water (2 mL) and to it was added a solution of silver nitrite (75 mg, 0.48 mmol) in boiling water (2 mL). The solution was stirred for 5 min. while keeping the solution hot and then centrifuged at 1000 rpm for 5 min. The supernatant was decanted and the water was removed by lyophilisation. The residue was recrystalised from ethyl acetate/isopropanol to give the title compound as a white solid 124 mg (70%) mp 169–172° C. (dec). $^1$H NMR (DMSO-d$_6$) δ 7.15–7.30 (m, 5H), 4.90 (t, J=5.5 Hz, 1H), 3.97–4.04 (m, 1H), 3.65–3.82 (m, 4H), 3.55–3.62 (m, 1H), 2.56 (s, 3H), 2.28–2.5 (m, 2H), 1.75–2.1 (m, 4H), 1.57 (d, J=17 Hz, 1H), 1.40–1.50 (m, 1H), 1.06–1.14 (m, 6H). $^{13}$C NMR (DMSO-d$_6$) δ16.36, 24.46, 24.73, 31.25, 54.53, 55.18, 63.31, 65.20, 65.30, 127.82, 128.47, 129.00, 136.48, 171.64. Anal calcd for C$_{20}$H$_{30}$N$_2$O$_5$:C: 63.47; H: 7.99; N: 7.40. Found: C: 63.28; H: 7.92; N: 7.24.

Example 3

(8r)-3α-hydroxy-8-isopropyl-1αH,5αH-tropanium nitrate (±)-tropate (8r)-3α-hydroxy-8-isopropyl-1αH,5αH-tropanium nitrate (±)-tropate (0.2 g, 0.48 mmol) was dissolved in ethanol (2 mL) and to it added a solution of silver nitrate (82 mg, 0.48 mmol) in water (2 mL). The solution was stirred at room temperature for 1.5 hr. and centrifuged at 1000 rpm for 5 min. The supernatant was decanted and the volatile materials removed by lyophilisation. The product was recrystalised from isopropanol to give the title compound as a white solid 150 mg (76%) mp 180–182° C. $^1$H NMR (DMSO-d$_6$) δ 7.21–7.39 (m, 5H), 5.03 (t, J=5.7 Hz, 1H), 4.07–4.16 (m, 1H), 3.78–3.94 (m, 4H), 3.59–3.65 (m, 1H), 2.68 (s, 3H), 2.4–2.6 (m, 2H), 1.9 –2.22 (m, 3H), 1.91 (d, J=17.2 Hz, 1H), 1.69 (d, J=17.2 Hz, 1H), 1.49–1.59 (m, 1H), 1.06–1.14 (t, J=6 Hz, 6H). $^{13}$C NMR (DMSO-d$_6$) δ16.33, 24.45, 24.73, 31.25, 54.52, 55.19, 63.32, 65.20, 65.31, 127.83, 128.48, 129.00, 136.45, 171.62. Anal calcd for C$_{20}$H$_{30}$N$_2$O$_6$: C: 60.89; H: 7.66; N: 7.10. Found: C: 60.71; H: 7.68; N: 6.90.

Example 4

9-Fluoro-11β-hydroxy-16α,17α-((1-methylethylidene)bis(oxy))prena-1,4-diene-3,20-dione-21-(4-nitrooxy)-butanoate 4a. 9-Fluoro-11β-hydroxy-16α,17α-((1-methylethylidene)bis(oxy))pregna-1,4-diene-3,20-dione-21-(4-bromo)-butanoate and 9-Fluoro-11β-hydroxy-16α,17α-((1-methylethylidene)bis(oxy))pregna-1,4-diene-3,20-dione-21-(4-iodo)-butanoate A solution of 9-Fluoro-11β, 21-dihydroxy-16α,17α-((1-methylethylidene)bis(oxy))pregna-1,4-diene-3,20-dione (1.6 g, 3.7 mmol) and 4-bromobutyric acid (0.61 g, 3.7 mmol) in dry DMF (15 mL) at room temperature under nitrogen was treated with 4-DMAP (90 mg, 0.74 mmol) and 1-ethyl-3-(3-dimethylaminopropyl)carbodiimide methiodide (1.28 g, 4.4 mmol) and the resultant solution stirred overnight at room temperature. The solvent was removed in vacuo and the residue chromatographed on silica gel using ethyl acetate:hexane (1:1 then 2:1) to give the product 0.8 g (an inseperable mixture of bromide and iodide) as a white solid together with 1.2 g of recovered 9-fluoro-11β, 21-dihydroxy-16α,17α-((1-methylethylidene)bis(oxy))pregna-1, 4-diene-3,20-dione. $^1$H NMR (CDCl$_3$) δ 7.23 (d, J=10 Hz, 1H), 6.37 (dd, J=10 Hz, 1.7 Hz, 1H), 6.15 (s, 1H), 4.95 (dd, J=50 Hz, 18 Hz, 2H), 5.00 (s, 1H), 4.45 (br d, J=3.5 Hz), 3.53 (2t, J=6.4 and 6.7 Hz, 2H), 3.30 (2t, J=6.4 and 6.7 Hz, 2H), 2.00–2.7 (m, 10H), 1.85–1.95 (m, 1H), 1.6–1.75 (m, 3H), 1.57 (s, 3H), 1.45 (s, 3H), 1.24 (s, 3H), 0.96 (s, 3H).

4b. 9-Fluoro-11β-hydroxy-16α,17α-((1-methylethylidene)bis(oxy))pregna-1,4-diene-3,20-dione-21-(4-nitrooxy)-butanoate To the products of Example 4a (0.45 g) in acetonitrile (5 mL) and DMF (1 mL) was added silver nitrate (1.95 g 1.5 equivalents based on bromide as exclusive starting material) and the resultant solution stirred overnight at room temperature. Then, further silver nitrate (100 mg) was added and the resultant solution stirred an additional 24 hrs at room temperature. The solution was filtered and the filtercake washed with methanol. The filtrate was reduced in vacuo and the residue chromatographed on silica gel using ethyl acetate:hexane (1:1) to give the product as a white solid. mp. 211–213° C. $^1$H NMR (CDCl$_3$) δ 7.26 (d, J=10 Hz, 1H), 6.35 (d, J=10 Hz, 1H), 6.14 (s, 1H), 4.95 (dd, J=50 Hz, 17 Hz), 4.99 (d, J=4.6 Hz, 1H), 4.56 (t, J=6.2 Hz, 2H), 4.43 (d, J=8.5 Hz, 1H), 2.33–2.75 (m, 7H), 2.04–2.18 (m, 3H), 1.84–1.95 (m, 1H), 1.55–1.75 (m, 3H), 1.56 (s, 3H), 1.44 (s, 3H), 1.22 (s, 3H), 0.94 (s, 3H). Anal calcd for C$_{28}$H$_{36}$FNO$_{10}$: C, 59.46; H, 6.42. Found: C, 59.26; H, 6.34.

Example 5

9-Fluoro-11β-hydroxy-16α,17α-((1-methylethylidene)bis(oxy))pregna-1,4-diene-3,20-dione-21-(12-nitrosooxy)-dodecanoate 5a. 9-Fluoro-11β-hydroxy-16α,17α-((1-methylethylidene)bis(oxy))pregna-1,4-diene-3,20-dione-21-(12-tert-butyldimethylsilyloxy)-dodecanoate A solution of 9-Fluoro-11β, 21-dihydroxy-16α,17α-((1-methylethylidene)bis(oxy))pregna-1,4-diene-3,20-dione (1 g, 2.3 mmol) and 12-tert-butyldimethylsilyloxydodecanoic acid (760 mg, 2.3 mmol) (*J. Org. Chem.*, 50, 1616 (1985)) in dry DMF (10 mL) was stirred at room temperature under nitrogen and 4-DMAP (56 mg, 0.46 mmol) added followed by 1-ethyl-3-(3-dimethylaminopropyl)carbodiimide hydrochloride (528 mg, 2.8 mmol). The resultant solution was stirred overnight at room temperature and the solvent removed in vacuo. The residue was chromatographed on silica gel using ethyl acetate:hexane (1:3 then 1:1) to give the product as a white solid 1.1 g (70% based on recovered starting material). mp. 146–148° C. $^1$H NMR (CDCl$_3$) δ 7.16 (d, J=10 Hz, 1H), 6.30 (d, J=10 Hz, 1H), 6.09 (s, 1H), 4.94 (d, J=4.9 Hz, 1H), 4.86 (d, J=6.9 Hz), 4.37 (d, J=8.6 Hz, 1H), 3.55 (t, J=6.5 Hz, 2H), 2.59 (m, 1H), 2.32–2.45 (m, 6H), 2.04–2.15 (m, 1H), 1.68–1.78 (m, 1H), 1.2–1.7 (21 H), 1.50 (s, 3H), 1.38 (s, 3H), 1.17 (s, 3H), 0.89 (s, 3H), 0.84 (s, 9H), 0.00 (s, 6H).

5b. 9-Fluoro-11β-hydroxy-16α,17α-((1-methylethylidene)bis(oxy))pregna-1,4-diene-3,20-dione-21-(12-hydroxy)-dodecanoate The product of Example 5a (0.15 g, 0.2 mmol) was dissolved in THF (1.3 mL) and trifluoroacetic acid (160 μL) added followed by water (40 μL). The resultant solution was stirred at room temperature for 1 hr, the volatile material removed in vacuo and the residue chromatographed on silica gel using ethyl acetate:hexane (2:1) to give the product as a white solid 100 mg (79%) mp 172–175° C. $^1$H NMR (CDCl$_3$) δ 7.21 (d, J=10 Hz, 1H), 6.35 (dd, J=10 Hz, 1.7 Hz, 1H), 6.14 (s, 1H), 4.99 (d, J=4.7 Hz, 1H), 4.91 (d, J=2.4 Hz, 2H), 4.41 (d, J=8.1 Hz, 1H), 3.65 (t, J=6.6 Hz, 2H), 2.57–2.7 (m, 1H), 2.35–2.52 (m, 4H), 2.07–2.17 (m, 1H), 1.83–1.94 (m, 1H), 1.44 (s, 3H), 1.57 (s, 3 H), 1.55–1.77 (m, 7H), 1.25–1.40 (m, 16H), 1.22 (s, 3H), 0.94 (s, 3H). $^{13}$C NMR (CDCl$_3$) δ203.82, 186.47, 173.69, 165.91, 152.04, 129.76, 125.13, 111.51, 101.24, 98.91, 97.60, 81.88, 72.08, 71.57, 67.57, 62.92, 48.32, 48.02, 45.55, 43.03, 36.91, 33.73, 33.68, 33.33, 33.08, 32.62, 30.88, 29.30, 29.21, 29.18, 29.14, 28.99, 28.84, 27.55, 26.48, 25.80, 25.59, 24.75, 22.98, 22.91, 16.29. Anal calcd for C$_{36}$H$_{53}$FO$_8$: C, 68.33; H, 8.44. Found: C, 68.11; H, 8.37.

5c. 9-Fluoro-11β-hydroxy-16α,17α-((1-methylethylidene)bis(oxy))pregna-1,4-diene-3,20-dione-21-(12-nitrosooxy)-dodecanoate The alcohol prepared above (90 mg, 142 μmol) was dissolved in the solvent in a dry flask under N$_2$ and cooled over dry ice. After stirring for 10 min pyridine (57.5 μL, 712 μmol) was added followed by nitresonium tetrafluoroborate (33 mg, 285 μmol). The resultant solution was stirred at −78° C. for 3 hr, washed with water, dried over sodium sulfate, filtered and the solvent removed in vacuo. The residue was chromatographed on silica gel using ethyl acetate:hexane: triethylamine (50:48:2) to give the product 45 mg (47%). $^1$H. NMR (CDCl$_3$) δ 7.22 (d, J=10 Hz, 1H), 6.34 (dd, J=10 Hz, 1.3 Hz, 1H), 6.13 (m, 1H), 4.90 (dd, J=40 Hz, 18 Hz, 2H), 4.69 (br s, 2H), 4.41 (d, J=8 Hz, 1H), 2.28–2.71 (m, 7H), 2.04–2.15 (in, 1H), 1.82–1.92 (m, 1H), 1.54 (s, 3H), 1.42 (s, 3H), 1.21 (s, 3H), 1.2–1.8 (m, 22H), 0.94 (s, 3H). $^{13}$C NMR (CDCl$_3$)δ203.84, 186.43, 173.50, 165.81, 151.85, 129.86, 125.16, 111.51, 101.17, 98.00, 81.86, 72.16, 71.66, 67.48, 48.26, 47.96, 45.48, 42.98, 37.27, 33.77, 33.62, 33.27, 33.01, 30.86, 29.38, 29.32, 29.17, 29.12, 28.99, 27.52, 26.46, 25.81, 25.76, 243.82, 22.97, 22.89, 16.36

Example 6

2-(tert-Butylamino-1-(4-hydroxy-3-hydroxymethylphenyl)ethanol 2(R,S)-acetamido-3-methyl-3-nitrosothiol Propionic Acid Salt 6a. 2(R,S)-acetamido-3-methyl-3-nitrosothiol Propionic Acid 2(R,S)-acetamido-3-methyl-3-mercapto-propionic acid (0.2 g, 1.05 mmol) was dissolved in dry DMF (2 mL) and stirred at room temperature under nitrogen. tert-Butyl nitrite (248 μL, 215 mg, 2.09 mmol) was introduced and the resultant solution stirred at room temperature for 25 min when the solvent was removed in vacuo at room temperature. The green gum was stirred with ether collecting the resultant solid by filtration (225 mg, 97%). $^1$H NMR (DMSO-d6) δ 13.21 (br s, 1H), 8.54 (d, J=9.45 Hz, 1H), 5.18 (d, J=5.46 Hz, 1H), 1.98 (s, 3H), 1.95 (s, 3H), 1.88 (s, 3H).

6b. 2-(tert-Butylamino-1-(4-hydroxy-3-hydroxymethylphenyl)ethanol 2(R,S)-acetamido-3-methyl-3-nitrosothiol Propionic Acid Salt 2-(tert-Butylamino-1-(4-hydroxy-3-hydroxymethylphenyl)ethanol_25 mg, 0.1 mmol) and the product of Example 6a (23 mg, 0.1 mmol) were stirred in water to homogeneity then lyophilised to dryness to give the salt (48 mg, 100%) mp 180–182° C. $^1$H NMR (DMSO-d$_6$) δ 9.38 (br s, 1H), 7.81 (d, J=9.34 Hz, 1H), 7.33 (s, 1H), 7.08.(d, J=8.2 Hz, 1H), 6.75 (d, J=8.2 Hz, 1H), 4.98 (br s, 1H), 4.69 (d, J=9.2 Hz, 1H), 2.72–2.95 (m, 2H), 1.97 (s, 3H), 1.94 (s, 3H), 1.86 (s, 3H), 1.23 (s, 9H). $^{13}$C NMR (DMSO-d 6)δ172.52, 169.33, 154.07, 132.63, 128.60, 125.41, 125.29, 114.63, 69.16, 61.45, 60.77, 58.61, 55.54, 48.91, 27.36, 26.21, 25.63, 23.04. Anal calcd for C$_{20}$H$_{33}$N$_3$O$_7$S: C, 52.27; H, 7.23; N, 9.14. Found: C, 52.49; H, 7.33; N, 8.85.

Example 7

5,5'-((2-Hydroxy-1,3-propanediyl)bis-(oxy))bis(4-oxo-4H-1benzopyran-2(4-nitrooxybutyl)-carboxylic Acid Ester 7a. 5,5'-((2-Hydroxy-1,3-propanediyl)bis-(oxy))bis(4-oxo-4H-1 benzopyran-2(4-bromobutyl)-carboxylic Acid Ester 5,5'-((2-Hydroxy-1,3-propanediyl)bis-(oxy))bis(4-oxo-4H-1benzopyran-2-carboxylic acid disodium salt (2.6 g, 5.07 mmol) and 1,4-dibromobutane (8.7 g, 40.6 mmol) were stirred at room temperature in DMSO for 72 hr and then the solvent removed by vacuum distillation. The residue was diluted with $CH_2Cl_2$ and washed with water. The aqueous phase was extracted once with $CH_2Cl_2$ and the combined extracts washed with brine and dried over sodium sulfate. The solution was filtered, the solvent removed in vacuo and the residue chromatographed on silica gel using ethyl acetate:hexane (4:1) to give cromolyn bis(4-ester) as a solid 1.2 g (32%). mp 130–133° C. $^1$H NMR (DMSO-d6) δ7.74 (t, J=8.4 Hz, 2H), 7.16 (dd, J=18.6 Hz, 8.4 Hz, 4H), 6.73 (s, 2H), 5.37 (br. s, 1H), 4.29–4.40 (m, 9H), 3.63 (t, J=6.3 Hz, 4H), 1.83–2.03 (m, 8H). $^{13}$C NMR (DMSO-d6) δ 176.88, 160.35, 158.77, 157.48, 150.40, 135.76, 115.73, 114.96, 110.57, 109.38, 70.46, 67.34, 66.02, 35.08, 29.21, 26.93. Anal calcd for $C_{31}$, $H_{30}Br_2O_{11}$: 50.42; H, 4.10. Found: C, 50.05; H, 4.42.

7b. 5,5'-((2-Hydroxy-1,3-propanediyl)bis-(oxy))bis(4-oxo-4H-1 benzopyran-2(4-nitrooxybutyl)-carboxylic Acid Ester The product of Example 7a (0.5 g, 0.68 mmol) was dissolved in a mixture of acetonitrile (15 mL) and DMF (5 mL) and silver nitrate (0.92 g, 5.4 mmol) added. The solution was stirred overnight at room temperature and then additional silver nitrate (0.46 g, 2.7 mmol) added. After stirring an additional 24 hr at room temperature the solvent was removed in vacuo and the residue chromatographed directly on silica gel using ethyl acetate:hexane (4:1) to give the product as a white solid. mp. 211–213° C. $^1$H NMR (DMSO-d$_6$) δ 7.74 (t, J=8.4 Hz, 2H), 7.16 (dd, J=18.2 Hz, 8.4 Hz, 2H), 6.73 (s, 2H), 5.37 (d, J=3.9 Hz)4.57–4.63 (m, 4H), 4.28–4.40 (m, 8H), 4.71 (t, J=6 Hz, 1H), 1.75–1.88 (m, 8H). $^{13}$C NMR (CDCl$_3$) δ 178.03, 160.36, 158.75, 157.57, 150.25, 135.02, 116.32, 115.54, 111.05, 109.63, 72.31, 70.25, 67.68, 65.81, 24.84, 23.55. Anal calcd for $C_{31}H_{30}N_2O_{17}$: 52.99; H, 4.30; N, 3.99. Found: C, 52.67; H, 4.38; N, 3.66.

Example 8

5,5'-((2-Hydroxy-1,3-propanediyl)bis-(oxy))bis(4-oxo-4H-1benzopyran-2(4-(2(S)-acetamido-3-methyl-3-nitrosothiol) propionic acid butyl)-carboxylic Acid Ester 8a. 5,5'-((2-Hydroxy-1,3-propanediyl)bis-(oxy))bis(4-oxo-4H-1benzopyran-2(4-(2(S)-tert-butyloxycarboxamido-3-methyl-3-tert-butyloxythiocarbonato) propionic acid butyl)-carboxylic Acid Ester The product of Example 7a (0.7 g, 0.95 mmol) and 2(S)-terbutyloxycaboxamido-3-methyl-3-tert-butyloxythiocarbonato-propionic acid (U.S. Pat. No. 5,187,305) (974 mg, 2.86 mmol) were mixed in dry DMF (10 mL) together with sodium iodide (28 mg, 0.19 mmol) and potassium carbonate (394 mg, 2.86 mmol). The resultant solution was stirred at room temperature for 72 h, the solvent removed in vacuo and the residue chromatographed on silica gel using ethyl acetate:hexane (3:2) to give the product as a foam 620 mg (52%). $^1$H NMR (CDCl$_6$) δ 7.57 (t, J=8.4 Hz, 2H), 7.14 (d, J=8.4 Hz, 2H), 6.94 (d, J=8.4 Hz, 2H), 6.92 (s, 2H), 5.58 (d, J=9 Hz, 2H), 4.73 (d, J=7.4 Hz, 2H), 4.3–4.58 (m, 9H), 4.18–4.25 (m, 4H), 1.77–1.92 (m, 8H), 1.50 (s, 6H), 1.45 (s, 18H), 1.44 (s, 6H), 1.40 (s, 18H). $^{13}$C NMR (CDCl$_3$) δ 177.95, 170.52, 167.32, 160.32, 158.69, 157.53, 155.16, 150.35, 134.86, 116.17, 115.51, 111.03, 109.54, 85.08, 79.78, 70.22, 67.63, 66.08, 64.39, 59.88, 51.14, 28.17, 28.12, 27.80, 25.32, 25.05, 25.01

8b. 5,5'-((2-Hydroxy-1,3-propanediyl)bis-(oxy))bis(4-oxo-4H-1benzopyran-2(4-(2(S)-acetamido-3-methyl-3-mercapto) propionic acid butyl)-carboxylic Acid Ester The product of Example 8a (0.62 mg, 0.49 mmol) was dissolved in $CH_2Cl_2$ (9 mL) and anisole (450 mg) added followed by trifluoroacetic acid (10 mL). The resultant solution was stirred at room temperature for 2 hr when the volatiles were removed in vacuo. The residue was dissolved in more $CH_2Cl_2$ (9 mL) and stirred over ice under nitrogen. After 10 minutes triethylainine (286 μL, 206 mg, 2.04 mmol) was introduced followed by acetyl chloride (76 ?L, 84 mg, 1.07 mmol). The resultant solution was stirred overnight at room temperature, washed with 0.5N HCl, dried over $Na_2SO_4$, filtered and the solvent removed in vacuo. The residue was chromatographed on silica gel using ethyl acetate:hexane (9:1) then ethyl acetate:methanol (9:1) to give the product as a foam 120 mg (30%). $^1$H NMR (CDCl$_3$) δ 7.54 (t, J=8.4 Hz, 2H), 7.08 (d, J=8.4, 2H), 6.90 (d, J=8.3 Hz, 2H), 6.87 (s, 2H), 6.57 (d, J=9.2 Hz, 2H), 4.58 (d, J=9.2 Hz, 2H), 4.15–4.55 (m, 13H), 2.01 (s, 6H), 1.96 (s, 2H), 1.75–1.9 (s, 8H), 1.44 (s, 6H), 1.31 (s, 6H). $^{13}$C NMR (CDCl$_3$) δ 177.88, 170.30, 169.91, 160.18, 158.51, 157.37, 150.15, 134.84, 116.02, 115.25, 110.83, 109.29, 70.09, 67.46, 65.93, 64.44, 60.33, 46.10, 30.83, 29.29, 24.90, 24.88, 22.91.

8c. 5,5'-((2-Hydroxy-1,3-propanediyl)bis-(oxy))bis(4-oxo-4H-1benzopyran-2(4-(2(S)-acetamido-3-methyl-3-nitrosothiol) propionic acid butyl)-carboxylic Acid Ester The product of Example 8b (110 mg, 0.11 mmol) was dissolved in $CH_2Cl_2$ (3 mL). To this was added tert butylnitrite (81 μL, 70 mg, 0.69 mmol) and the resultant solution stirred at room temperature for 1 hr. The volatile material was removed in vacuo and the residue chromatographed on silica gel using ethyl acetate:acetone (4:1) to givethe product as a foam 50 mg (43%). $^1$H NMR (CDCl$_3$) δ 7.61 (t, J=8.4 Hz, 2H), 7.17 (d, J=8.4 Hz, 2H), 6.90–7.08 (m, 4H), 6.40 (d, J=9.2 Hz, 2H), 5.35 (d, J =9.3 Hz, 2H), 4.1–4.65 (m, 13H), 2.07 (s, 6H), 2.04 (s, 6H), 1.95 (s, 6H), 1.73–1.88 (m, 8H). $^{13}$C NMR (CDCl$_3$) δ 178.06, 169.95, 169.90, 160.38, 158.76, 157.60, 150.35, 134.95, 116.27, 115.58, 111.09, 109.63, 70.28, 67.70, 65.99, 65.04, 60.14, 57.87, 26.90, 26.54, 25.04, 24.93, 23.10.

Example 9

Comparitive In Vivo Airway Responsiveness Activities

The measurement of biological activity in a pulmonary model of allergic asthma and lung inflammation was undertaken in adult conscious sheep. The methodology was essentially as described by W. M. Abraham et al. (*Bull. Eur. Physiopathol. Respir.*, 22, 387 (1986)). Adult sheep with a natural cutaneous reaction to Ascaris Summ extract and who respond to inhalation challenge with Ascaris Summ with both an acute bronchoconstriction and a late bronchial obstruction were used in the study.

Unsedated sheep were intubated and measurement of airway mechanics were computed and recorded on a digital computer utilizing inputs of transpulmonary pressure and tracheal airflow recordings. Each animal was exposed to an aerosol of ascaris suum, diluted to produce an immediate and significant increase in mean lung resistance (sR1) of approximately 600–700% above baseline. This acute response peaked within 30 minutes and remained significantly above baseline for 2 hours. By approximately 6.5 hours after challenge sR1 again significantly increased over baseline (130–200%) and remained elevated until 8 hours post challenge. This second response is known as the late response. sR1 returned to baseline by 24 hours. Each animal was exposed to an aerosol of ascaris suum at a minimum of two week interval. Each animal was exposed to an aerosol of ascaris suum at a minimum of two week interval. Each animal did not enter into a study until it responded in a reproducible manner to three separate exposures of a designated dose of ascaris suum, each exposure separated by a 2 week interval.

Airway responsiveness was measured by calculation of a PC150 value. The PC150 is the dose of aerosolized carbachol which produces a 150% increase in sR1 above baseline. The doses of carbachol were administered in an ascending dose-response fashion with each dose being administered for a 10 breath duration. The PC150 value was determined for each animal 24 hours prior to exposure to ascaris suum and again 24 post exposure. The difference in PC150 values represented a change in airway responsiveness. The closer the post challenge to prechallenge ratio to unity the better the effect of the particular compound.

Each test drug was aerosolized to an animal 30 minutes prior to challenge with ascaris suum.

Results

Sheep were treated with 500 µg of either Example 1 or 6α-flouro-11β, 21-dihydroxy-16α, 17α-((1-methylethylidene)bis(oxy))pregna-1,4-diene-3,20-dione. Data are referenced to historical controles as described in the methods section. The data showed that Example 1 gave 59±14% protection of the immediate response and 89±2% protection of the peak late response (n=3). 6α-Fluoro-11β,21-dihydroxy-16α, 17α-((1-methylethylidene) bis (oxy))pregna-1, 4-diene-3,20-dione gave 16±21% protection against the immediate response and 83±7% protection against the peak late response (n=3).

Measurement of airway hyperresponsiveness showed the post challenge/prechallenge ratios of PC150 values were 0.53±0.10 (control) and 1.18±0.06 (Example 1) and 0.59±0.06 (control) and 0.98±0.10 (6α-Fluoro-11β, 21-dihydroxy-16α, 17α-((1-methylethylidene) bis (oxy))pregna-1,4-diene-3,20-dione).

The results show that Example 1 provides a better protection against lung function changes due to aerosol challenge of ascaris suum in the conscious sheep.

It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. A β-agonist compound of Formula (II):

II wherein,

E is nitrogen or C—$R_7$;

$R_7$ is hydrogen, halogen, —$CH_2O$—$R_j$, or —O—$R_j$;

$R_j$ is hydrogen, D or M;

D is
(i) hydrogen
(ii) —NO
(iii) —$NO_2$
(iv) —CH($R_d$)—O—C(O)—Y—(C($R_e$)($R_f$))$_p$-T-Q;
(v) —C(O)-$T^1$-(C($R_e$)($R_f$))$_p$-$T^2$-Q; or
(vi) —C(O)-T-(C($R_y$)($R_z$))$_p$;

$R_d$ is hydrogen, lower alkyl, cycloalkyl, aryl, alkylaryl or heteroaryl;

Y is oxygen, sulfur or $NR_i$;

$R_i$ is hydrogen, lower alkyl, lower haloalkyl or heteroaryl;

$R_e$ and $R_f$ are each independently hydrogen, lower alkyl, cycloalkyl, aryl, heteroaryl, arylalkyl, alkylamino, dialkylamino, or carboxy, or $R_e$ and $R_f$ taken together with the carbon atom to which they are attached are carbonyl, cycloalkyl or bridged cycloalkyl;

p is an integer from 1 to 6;

T, $T^1$ and $T^2$ are each independently a covalent bond, oxygen, sulfur or nitrogen;

Q is —NO or —$NO_2$; with the proviso that in "T-Q" and "$T^2$-Q", T and $T^2$ cannot be a covalent bond;

$R_y$ and $R_z$ are each independently -$T^1$-(C($R_e$)($R_f$))$_p$-G-(C($R_e$)($R_f$))$_p$-$T^2$-Q;

G is a covalent bond, -T-C(O)—, —C(O)-T or Y; wherein $R_d$, $R_e$, $R_f$, p, Q, T, $T^1$, $T^2$ and Y are as defined herein;

M is
(i) —C(O)-T-(C($R_e$)($R_f$))$_p$-G-(C($R_e$)($R_f$))$_p$—N(N—($O^-$).N=O)—$R_i$ or
(ii) —CH($R_d$)—O—C(O)-T-(C($R_e$)($R_f$))$_p$-G-(C($R_e$)($R_f$))$_p$—N(N—($O^-$).N=O)—$R_i$;

wherein T, $R_e$, $R_f$, p, G, $R_i$, and $R_d$ are as defined herein;

$R_8$ and $R_9$ are each independently amino, hydrogen, —$CH_2O$—$R_j$, or —O—$R_k$;

$R_k$ is —C(O)—$R_d$ or $R_j$; wherein $R_d$ and $R_j$ are as defined herein;

$S_1$ is:
(1) —$CH_2$—N(Z)—$R_{10}$; wherein Z is hydrogen, —(N($O^-$)N=O), or M; wherein M is as defined herein;

$R_{10}$ is:
(i) lower alkyl
(ii) —($CH_2$)$_p$—O—($CH_2$)$_a$—$C_6H_5$; wherein a is an integer from 1 to 4 and p is defined herein;

(iii)

(2)

wherein Z is as defined herein;

$R_{11}$ is hydrogen, D, or M; with the proviso that $R_{11}$ must be D or M if neither $R_8$ or $R_9$ include D or M and Z is a hydrogen; and with the proviso that the compounds of Formula (II) must contain at least one —NO group or at least one —NO$_2$ group, and wherein the at least one —NO group or the at least one —NO$_2$ group is linked to the compounds of Formula (II) through an oxygen atom, a nitrogen atom or a sulfur atom.

2. The compound of claim 1, wherein the compound of Formula (II) is a nitrosated salmeterol, a nitrosylated salmeterol, a nitrosated and nitrosylated salmeterol, a nitrosated albuterol, a nitrosylated albuterol, a nitrosated and nitrosylated albuterol, a nitrosated metaproternol, a nitrosylated metaproternol, a nitrosated and nitrosylated metaproternol, a nitrosated terbutalin, a nitrosylated terbutalin, a nitrosated and nitrosylated terbutaline, a nitrosated pirbuterol, a nitrosylated pirbuterol, a nitrosated and nitrosylated pirbuterol, a nitrosated rimiterol, a nitrosylated rimiterol, a nitrosated and nitrosylated rimiterol, a nitrosated clenbuterol, a nitrosylated clenbuterol, a nitrosated and nitrosylated clenbuterol, a nitrosated bitolterol, a nitrosylated bitolterol, a nitrosated and nitrosylated bitolterol, a nitrosated reproterol, a nitrosylated reproterol or a nitrosated and nitrosylated reproterol.

3. A composition comprising the compound of claim 1 and a pharmaceutically acceptable carrier or excipient.

4. The composition of claim 3, wherein the composition is in a form that can be administered by oral inhalation, nasal inhalation or intranasal mucosal administration.

5. The composition of claim 3, wherein the composition is in a form that can be administered orally, enterally, topically, vaginally, sublingually, rectally, intramuscularly, intravenously or subcutaneously.

6. The composition of claim 3, wherein the composition is in form that can be administered as an aerosol.

7. A method for treating asthma in an individual comprising administering a therapeutically effective amount of the composition of claim 3.

8. A method for treating a respiratory disorder in an individual comprising administering a therapeutically effective amount of the composition of claim 3.

9. The method of claim 8, wherein the respiratory disorder is acute pulmonary vasoconstriction, pneumonia, traumatic injury, aspiration or inhalation injury, fat embolism in the lung, acidosis, inflammation of the lung, adult respiratory distress syndrome, acute pulmonary edema, acute mountain sickness, asthma, post cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus, hypoxia, chronic pulmonary hypertension, bronchopulmonary dysplasia, chronic pulmonary thromboembolism, idiopathic pulmonary hypertension, primary pulmonary hypertension or chronic hypoxia.

10. A method of treating cystic fibrosis in an individual comprising administering a therapeutically effective amount of the composition of claim 3.

11. The method of claim 7, 8 or 10, comprising administering a therapeutically effective amount of the composition by oral inhalation, by nasal inhalation, or by intranasal mucosal administration.

12. The method of claim 7, 8 or 10, comprising administering a therapeutically effective amount of the composition as an aerosol.

13. The method of claim 7, 8 or 10, comprising administering a therapeutically effective amount of the composition orally, enterally, topically, vaginally, sublingually, rectally, intramuscularly, intravenously, or subcutaneously.

14. A kit comprising the composition of claim 3.

15. A composition comprising a compound of Formula (II) and a compound that donates, transfers or releases nitric oxide, elevates endogenous synthesis levels of nitric oxide or endothelium-derived relaxing factor, or is a substrate for nitric oxide synthase, wherein the compound of Formula (II) is:

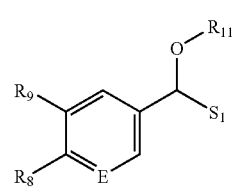

wherein,

E is nitrogen or C—$R_7$;

$R_7$ is hydrogen, halogen, —CH$_2$O—$R_j$, or O—$R_j$;

$R_j$ is hydrogen, D or M;

D is (i) hydrogen
(ii) —NO
(iii) —NO$_2$
(iv) —CH($R_d$)—O—C(O)—Y—(C($R_e$)($R_f$))$_p$-T-Q;
(v) —C(O)-T$^1$-(C($R_e$)($R_f$))$_p$-T$^2$-Q; or
(vi) —C(O)-T-(C($R_y$)($R_z$))$_p$;

$R_d$ is hydrogen, lower alkyl, cycloalkyl, aryl, alkylaryl or heteroaryl;

Y is oxygen, sulfur or NR$_i$;

$R_i$ is hydrogen, lower alkyl, lower haloalkyl or heteroaryl;

$R_e$ and $R_f$ are each independently hydrogen, lower alkyl, cycloalkyl, aryl, heteroaryl, arylalkyl, alkylamino, dialkylamino, or carboxy, or $R_e$ and $R_f$ taken together with the carbon atom to which they are attached are carbonyl, cycloalkyl or bridged cycloalkyl;

p is an integer from 1 to 6;

T, T$^1$ and T$^2$ are each independently a covalent bond, oxygen, sulfur or nitrogen;

Q is —NO or —NO$_2$; with the proviso that in "T-Q" and "T$^2$-Q", T and T$^2$ cannot be a covalent bond;

$R_y$ and $R_z$ are each independently -T$^1$-(C($R_e$)($R_f$))$_p$-G-(C($R_e$)($R_f$))$_p$-T$^2$-Q;

G is a covalent bond, -T-C(O)—, —C(O)-T or Y; wherein $R_d$, $R_e$, $R_f$, p, Q, T, T$^1$, T$^2$ and Y are as defined herein;

M is:

(i) —C(O)-T-(C($R_e$)($R_f$))$_p$-G-(C($R_e$)($R_f$))$_p$—N(N—(O$^-$).N═O)—$R_i$ or
(ii) —CH($R_d$)—O—C(O)-T-(C($R_e$)($R_f$))$_p$-G-(C($R_e$)($R_f$))$_p$—N(N—(O$^-$).N═O)—$R_i$;

wherein T, $R_e$, $R_f$, p, G, $R_i$, and $R_d$ are as defined herein;

$R_8$ and $R_9$ are each independently amino, hydrogen, —CH$_2$O—$R_j$, or —O—$R_k$;

$R_k$ is —C(O)—$R_d$ or $R_j$; wherein $R_d$ and $R_j$ are as defined herein;

$S_1$ is:

(1) —CH$_2$—N(Z)—$R_{10}$; wherein Z is hydrogen, —(N(O$^-$)N═O), or M; wherein M is as defined herein;

$R_{10}$ is:
(i) lower alkyl
(ii) $-(CH_2)_p-O-(CH_2)_a-C_6H_5$; wherein a is an integer from 1 to 4 and p is defined herein;

(iii)

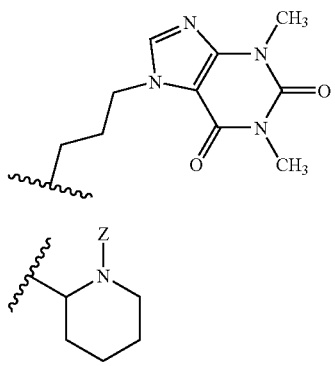

(2)

wherein Z is as defined herein;
$R_{11}$ is hydrogen, D, or M; with the proviso that $R_{11}$ must be D or M if neither $R_8$ or $R_9$ include D or M and Z is a hydrogen; and
with the proviso that the compounds of Formula (II) must contain at least one —NO group or at least one —$NO_2$ group, and wherein the at least one —NO group or the at least one —$NO_2$ group is linked to the compounds of Formula (II) through an oxygen atom, a nitrogen atom or a sulfur atom.

16. The composition of claim 15 further comprising a pharmaceutically acceptable carrier or excipient.

17. The composition of claim 15, wherein the compound that donates, transfers or releases nitric oxide, elevates endogenous synthesis levels of nitric oxide or endothelium-derived relaxing factor, or is a substrate for nitric oxide synthase is an S-nitrosothiol.

18. The composition of claim 17, wherein the S-nitrosothiol is S-nitroso-N-acetylcysteine, S-nitroso-captopril, S-nitroso-homocysteine, S-nitroso-cysteine, or S-nitroso-glutathione.

19. The composition of claim 17, wherein the S-nitrosothiol is
(i) $CH_3(C(R_e)(R_f))_xSNO$;
(ii) $HS(C(R_e)(R_f))_xSNO$;
(iii) $ONS(C(R_e)(R_f))_xB$; or
(iv) $H_2N-CH(CO_2H)-(CH_2)_x-C(O)NH-CH(CH_2SNO)-C(O)NH-CH_2-CO_2H$;
wherein x is 2 to 20; $R_e$ and $R_f$ are each independently hydrogen, lower alkyl, cycloalkyl, aryl, heteroaryl, arylalkyl, alkylamino, dialkylamino, or carboxy, or $R_e$ and $R_f$ taken together with the carbon atom to which they are attached are carbonyl, cycloalkyl or bridged cycloalkyl; and B is fluoro, $C_{1-6}$ alkoxy, cyano, carboxamido, cycloalkyl, arylalkoxy, alkylsulfinyl, arylthio, alkylamino, dialkylamino, hydroxy, carbamoyl, N-alkylcarbamoyl, N,N-dialkylcarbamoyl, amino, carboxyl, hydrogen, nitro or aryl.

20. The composition of claim 15, wherein the compound that donates, transfers or releases nitric oxide, elevates endogenous synthesis levels of nitric oxide or endothelium-derived relaxing factor, or is a substrate for nitric oxide synthase is L-arginine.

21. The composition of claim 15, wherein the compound that donates, transfers or releases nitric oxide, elevates endogenous synthesis levels of nitric oxide or endothelium-derived relaxing factor, or is a substrate for nitric oxide synthase is:
(i) a compound comprising at least one ON—N— or ON—O— group;
(ii) a compound comprising at least one $O_2N$—O—, $O_2N$—N— or $O_2N$—S— group;
(iii) a compound of the structure $(R)_u$-A-M-$(NO)_v$, wherein R is a polypeptide, an amino acid, a sugar, an oligonucleotide, a straight or branched, saturated or unsaturated, aromatic or aliphatic hydrocarbon, or a heterocyclic group; u and v are each independently an integer of 1, 2 or 3; A is sulfur, oxygen or nitrogen, and M is a metal; or
(iv) a compound of the structure $R_{61}R_{62}N$—N(O—$M^+$)—NO, wherein $R_{61}$ and $R_{62}$ are each independently a polypeptide, an amino acid, a sugar, an oligonucleotide, a straight or branched, saturated or unsaturated, aromatic or aliphatic hydrocarbon, or a heterocyclic group; and $M^+$ is a metal cation.

22. The composition of claim 21, wherein the compound comprising at least one ON—N— or ON—O— group is an ON—N-polypeptide, an ON—O-polypeptide, an ON—N-amino acid, an ON—O-amino acid, an ON—N-sugar, an ON—O-sugar, an ON—N-oligonucleotide, an ON—O-oligonucleotide, a straight or branched, saturated or unsaturated, aliphatic or aromatic, substituted or unsubstituted ON—N-hydrocarbon, a straight or branched, saturated or unsaturated, aliphatic or aromatic, substituted or unsubstituted ON—O-hydrocarbon, an ON—N-heterocyclic compound or an ON—O-heterocyclic compound.

23. The composition of claim 21, wherein the compound comprising at least one $O_2N$—O—,$O_2N$—N— or $O_2N$—S— group is an $O_2N$—O—polypeptide, an $O_2N$—N—polypeptide, an $O_2N$—S—polypeptide, an $O_2N$—O—amino acid, an $O_2N$—N—amino acid, an $O_2N$—S—amino acid, an $O_2N$—O— sugar, an $O_2N$—N— sugar, an $O_2N$—S— sugar, an $O_2N$—O-oligonucleotide, an $O_2N$—N—oligonucleotide, an $O_2N$—S—oligonucleotide, a straight or branched, saturated or unsaturated, aliphatic or aromatic, substituted or unsubstituted $O_2N$—O—hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S—hydrocarbon, an $O_2N$—O—heterocyclic compound, an $O_2N$—N—heterocyclic compound or an $O_2N$—S—heterocyclic compound.

24. The composition of claim 15, wherein the composition is in a form that can be administered by oral inhalation, nasal inhalation or intranasal mucosal administration.

25. The composition of claim 15, wherein the composition is in a form that can be administered as an aerosol.

26. The composition of claim 15, wherein the composition is in a form that can be administered orally, enterally, topically, vaginally, sublingually, rectally, intramuscularly, intravenously or subcutaneously.

27. A method for treating asthma in an individual comprising administering a therapeutically effective amount of the composition of claim 15.

28. A method for treating a respiratory disorder in an individual comprising administering a therapeutically effective amount of the composition of claim 15.

29. The method of claim 28, wherein the respiratory disorder is acute pulmonary vasoconstriction, pneumonia, traumatic injury, aspiration or inhalation injury, fat embolism in the lung, acidosis, inflammation of the lung, adult respiratory distress syndrome, acute pulmonary edema, acute mountain sickness, asthma, post cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus, hypoxia, chronic pulmonary hypertension, bronchopulmonary dysplasia, chronic pulmonary thromboembolism, idiopathic pulmonary hypertension, primary pulmonary hypertension or chronic hypoxia.

30. A method of treating cystic fibrosis in an individual comprising administering a therapeutically effective amount of the composition of claim 15.

31. The method of claim 27, 28 or 30, comprising administering a therapeutically effective amount of the composition by oral inhalation, by nasal inhalation, or by intranasal mucosal administration.

32. The method of claim 27, 28 or 30, comprising administering a therapeutically effective amount of the composition as an aerosol.

33. The method of claim 27, 28 or 30, comprising administering a therapeutically effective amount of the composition orally, enterally, topically, vaginally, sublingually, rectally, intramuscularly, intravenously, or subcutaneously.

34. A kit comprising a compound of Formula (II) and a compound that donates, transfers or releases nitric oxide, elevates endogenous synthesis levels of nitric oxide or endothelium-derived relaxing factor, or is a substrate for nitric oxide synthase, wherein the compound of Formula (II) is:

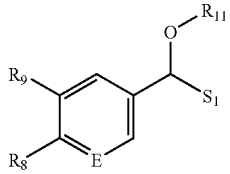

II wherein,

E is nitrogen or C—$R_7$;
$R_7$ is hydrogen, halogen, —$CH_2O$—$R_j$, or —O—$R_j$;
$R_j$ is hydrogen, D or M;
D is
 (i) hydrogen
 (ii) —NO
 (iii) —$NO_2$
 (iv) —$CH(R_d)$—O—C(O)—Y—$(C(R_e)(R_f))_p$-T-Q;
 (v) —C(O)-$T^1$-$(C(R_e)(R_f))_p$-$T^2$-Q; or
 (vi) —C(O)-T-$(C(R_y)(R_z))_p$;
$R_d$ is hydrogen, lower alkyl, cycloalkyl, aryl, alkylaryl or heteroaryl;
Y is oxygen, sulfur or $NR_i$;
$R_i$ is hydrogen, lower alkyl, lower haloalkyl or heteroaryl;
$R_e$ and $R_f$ are each independently hydrogen, lower alkyl, cycloalkyl, aryl, heteroaryl, arylalkyl, alkylamino, dialkylamino, or carboxy, or $R_e$ and $R_f$ taken together with the carbon atom to which they are attached are carbonyl, cycloalkyl or bridged cycloalkyl;
p is an integer from 1 to 6;
T, $T^1$ and $T^2$ are each independently a covalent bond, oxygen, sulfur or nitrogen;

Q is —NO or —$NO_2$; with the proviso that in "T-Q" and "$T^2$-Q", T and $T^2$ cannot be a covalent bond;
$R_y$ and $R_z$ are each independently -$T^1$-$(C(R_e)(R_f))_p$-G-$(C(R_e)(R_f))_p$-$T^2$-Q;
G is a covalent bond, -T-C(O)—, —C(O)-T or Y; wherein $R_d$, $R_e$, $R_f$, p, Q, T, $T^1$, $T^2$ and Y are as defined herein;
M is:
 (i)  —C(O)-T-$(C(R_e)(R_f))_p$-G-$(C(R_e)(R_f))_p$—N(N—($O^-$).N=O)—$R_i$, or
 (ii) —$CH(R_d)$—O—C(O)-T-$(C(R_e)(R_f))_p$-G-$(C(R_e)(R_f))_p$—N(N—($O^-$).N=O)—$R_i$;
wherein T, $R_e$, $R_f$, p, G, $R_i$, and $R_d$ are as defined herein;
$R_8$ and $R_9$ are each independently amino, hydrogen, —$CH_2O$—$R_j$, or —O—$R_k$;
$R_k$ is —C(O)—$R_d$ or $R_j$; wherein $R_d$ and $R_j$ are as defined herein;
$S_1$ is:
 (1) —$CH_2$—N(Z)—$R_{10}$; wherein Z is hydrogen, —(N($O^-$)N=O), or M; wherein M is as defined herein;
$R_{10}$ is:
 (i) lower alkyl
 (ii) —$(CH_2)_p$—O—$(CH_2)_a$—$C_6H_5$; wherein a is an integer from 1 to 4 and p is as defined herein;

(iii)
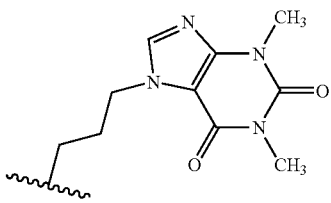

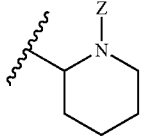
(2)

wherein Z is as defined herein;
$R_{11}$ is hydrogen, D, or M; with the proviso that $R_{11}$ must be D or M if neither $R_8$ or $R_9$ include D or M and Z is a hydrogen; and
with the proviso that the compounds of Formula (II) must contain at least one —NO group or at least one —$NO_2$ group, and wherein the at least one —NO group or the at least one —$NO_2$ group is linked to the compounds of Formula (II) through an oxygen atom, a nitrogen atom or a sulfur atom.

35. The kit of claim 34, wherein the compound of Formula (II) and the a compound that donates, transfers or releases nitric oxide, elevates endogenous synthesis levels of nitric oxide or endothelium-derived relaxing factor, or is a substrate for nitric oxide synthase are separate components in the kit or are in the form of a composition in the kit.

36. A composition comprising a therapeutically effective amount of a β-agonist and a compound that donates, transfers or releases nitric oxide, elevates endogenous synthesis levels of nitric oxide or endothelium-derived relaxing factor, or is a substrate for nitric oxide synthase, wherein the β-agonist is salmeterol, albuterol, metaproternol, terbutaline, pirbuterol, rimiterol, bitolterol or reproterol.

37. The composition of claim 36, further comprising a pharmaceutically acceptable carrier or excipient.

38. The composition of claim 36, wherein the compound that donates, transfers or releases nitric oxide, elevates endogenous synthesis levels of nitric oxide or endothelium-derived relaxing factor, or is a substrate for nitric oxide synthase is an S-nitrosothiol.

39. The composition of claim 38, wherein the S-nitrosothiol is S-nitroso-N-acetylcysteine, S-nitroso-captopril, S-nitroso-homocysteine, S-nitroso-cysteine, or S-nitroso-glutathione.

40. The composition of claim 38, wherein the S-nitrosothiol is
   (i) $CH_3(C(R_e)(R_f))_xSNO$;
   (ii) $HS(C(R_e)(R_f))_xSNO$;
   (iii) $ONS(C(R_e)(R_f))_xB$; or
   (iv) $H_2N-CH(CO_2H)-(CH_2)_x-C(O)NH-CH(CH_2SNO)-C(O)NH-CH_2-CO_2H$;
   wherein x is 2 to 20; $R_e$ and $R_f$ are each independently hydrogen, lower alkyl, cycloalkyl, aryl, heteroaryl, arylalkyl, alkylamino, dialkylamino, or carboxy, or $R_e$ and $R_f$ taken together with the carbon atom to which they are attached are carbonyl, cycloalkyl or bridged cycloalkyl; and B is fluoro, $C_{1-6}$ alkoxy, cyano, carboxamido, cycloalkyl, arylalkoxy, alkylsulfinyl, arylthio, alkylamino, dialkylamino, hydroxy, carbamoyl, N-alkylcarbamoyl, N,N-dialkylcarbamoyl, amino, carboxyl, hydrogen, nitro or aryl.

41. The composition of claim 36, wherein the compound that donates, transfers or releases nitric oxide, elevates endogenous synthesis levels of nitric oxide or endothelium-derived relaxing factor, or is a substrate for nitric oxide synthase is L-arginine.

42. The composition of claim 36, wherein the compound that donates, transfers or releases nitric oxide, elevates endogenous synthesis levels of nitric oxide or endothelium-derived relaxing factor, or is a substrate for nitric oxide synthase:
   (i) a compound comprising at least one ON—N— or ON—O— group;
   (ii) a compound comprising at least one $O_2N$—O—, $O_2N$—N— or $O_2N$—S— group;
   (iii) a compound of the structure $(R)_u$-A-M-$(NO)_v$, wherein R is a polypeptide, an amino acid, a sugar, an oligonucleotide, a straight or branched, saturated or unsaturated, aromatic or aliphatic hydrocarbon, or a heterocyclic group; u and v are each independently an integer of 1, 2 or 3; A is sulfur, oxygen or nitrogen, and M is a metal; or
   (iv) a compound of the structure $R_{61}R_{62}N$—N(O-M$^+$)—NO, wherein $R_{61}$ and $R_{62}$ are each independently a polypeptide, an amino acid, a sugar, an oligonucleotide, a straight or branched, saturated or unsaturated, aromatic or aliphatic hydrocarbon, or a heterocyclic group; and M$^+$ is a metal cation.

43. The composition of claim 42, wherein the compound comprising at least one ON—N— or ON—O— group is an ON—N-polypeptide, an ON—O-polypeptide, an ON—N-amino acid, an ON—O-amino acid, an ON—N-sugar, an ON—O-sugar, an ON—N-oligonucleotide, an ON—O-oligonucleotide, a straight or branched, saturated or unsaturated, aliphatic or aromatic, substituted or unsubstituted ON—N-hydrocarbon, a straight or branched, saturated or unsaturated, aliphatic or aromatic, substituted or unsubstituted ON—O-hydrocarbon, an ON—N-heterocyclic compound or an ON—O-heterocyclic compound.

44. The composition of claim 42, wherein the compound comprising at least one $O_2N$—O—, $O_2N$—N— or $O_2N$—S— group is an $O_2N$—O—polypeptide, an $O_2N$—N-polypeptide, an $O_2N$-Sp polypeptide, an $O_2N$—O—amino acid, an $O_2N$—N—amino acid, an $O_2N$—S—amino acid, an $O_2N$—O— sugar, an $O_2N$—N— sugar, an $O_2N$—S— sugar, an $O_2N$—O-oligonucleotide an $O_2N$—N-oligonucleotide, an $O_2N$—S-oligonucleotide, a straight or branched, saturated or unsaturated, aliphatic or aromatic, substituted or unsubstituted $O_2N$—O—hydrocarbon, a straight or branched, saturated or unsaturated, aliphatic or aromatic, substituted or unsubstituted $O_2N$—N—hydrocarbon, a straight or branched, saturated or unsaturated, aliphatic or aromatic, substituted or unsubstituted $O_2N$—S-hydrocarbon, an $O_2N$—O—heterocyclic compound, an $O_2N$—N-heterocyclic compound or an $O_2N$—S—heterocyclic compound.

45. The composition of claim 36 wherein the composition is in a form that can be administered by oral inhalation, nasal inhalation or intranasal mucosal administration.

46. The composition of claim 36, wherein the composition is in a form that can be administered as an aerosol.

47. The composition of claim 36, wherein the composition is in a form that can be administered orally, enterally, topically, vaginally, sublingually, rectally, intramuscularly, intravenously or subcutaneously.

48. A method for treating asthma in an individual comprising administering a therapeutically effective amount of the composition of claim 36.

49. A method for treating a respiratory disorder in an individual comprising administering a therapeutically effective amount of the composition of claim 36.

50. The method of claim 49, wherein the respiratory disorder is acute pulmonary vasoconstriction, pneumonia, traumatic injury, aspiration or inhalation injury, fat embolism in the lung, acidosis, inflammation of the lung, adult respiratory distress syndrome, acute pulmonary edema, acute mountain sickness, asthma, post cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus, hypoxia, chronic pulmonary hypertension, bronchopulmonary dysplasia, chronic pulmonary thromboembolism, idiopathic pulmonary hypertension, primary pulmonary hypertension or chronic hypoxia.

51. A method of treating cystic fibrosis in an individual comprising administering a therapeutically effective amount of the composition of claim 36.

52. The method of claim 48, 49 or 51, comprising administering a therapeutically effective amount of the composition by oral inhalation, by nasal inhalation, or by intranasal mucosal administration.

53. The method of claim 48, 49 or 51, comprising administering a therapeutically effective amount of the composition as an aerosol.

54. The method of claim 48, 49 or 51, comprising administering a therapeutically effective amount of the composition orally, enterally, topically, vaginally, sublingually, rectally, intramuscularly, intravenously, or subcutaneously.

55. A kit comprising a β-agonist and a compound that donates, transfers or releases nitric oxide, elevates endogenous synthesis levels of nitric oxide or endothelium-derived relaxing factor, or is a substrate for nitric oxidesynthase.

56. The kit of claim 55, wherein the compound of β-agonist and the compound that donates, transfers or releases nitric oxide, elevates endogenous synthesis levels of nitric oxide or endothelium-derived relaxing factor, or is a substrate for nitric oxide synthase are separate components in the kit or are in the form of a composition in the kit.

57. The composition of claim 23, wherein the compound comprising at least one $O_2N$—O—, $O_2N$—N— or $O_2N$—S— group is isosorbide dinitrate and isosorbide mononitrate.

58. The composition of claim 44, wherein the compound comprising at least one $O_2N$—O—, $O_2N$—N— or $O_2N$—S— group is isosorbide dinitrate and isosorbide mononitrate.

* * * * *